(12) United States Patent
Katiraee et al.

(10) Patent No.: US 11,408,029 B2
(45) Date of Patent: Aug. 9, 2022

(54) SPATIAL ANALYSIS OF DNA METHYLATION

(71) Applicant: 10x Genomics, Inc., Pleasanton, CA (US)

(72) Inventors: Layla Katiraee, Pleasanton, CA (US); Michael Schnall-Levin, Pleasanton, CA (US); Christina Galonska, Stockholm (SE); Marlon Stoeckius, Stockholm (SE)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/573,119

(22) Filed: Jan. 11, 2022

(65) Prior Publication Data

US 2022/0127666 A1    Apr. 28, 2022

Related U.S. Application Data

(63) Continuation of application No. PCT/US2021/039103, filed on Jun. 25, 2021.

(60) Provisional application No. 63/044,042, filed on Jun. 25, 2020, provisional application No. 63/128,783, filed on Dec. 21, 2020.

(51) Int. Cl.
*C12Q 1/6837* (2018.01)
*C12Q 1/6806* (2018.01)
*C12Q 1/6876* (2018.01)

(52) U.S. Cl.
CPC ......... *C12Q 1/6837* (2013.01); *C12Q 1/6806* (2013.01); *C12Q 1/6876* (2013.01); *C12Q 2600/154* (2013.01)

(58) Field of Classification Search
None
See application file for complete search history.

(56) References Cited

U.S. PATENT DOCUMENTS

| 4,683,195 | A | 7/1987 | Mullis |
| 4,683,202 | A | 7/1987 | Mullis |
| 4,800,159 | A | 1/1989 | Mullis |
| 4,883,867 | A | 11/1989 | Lee |
| 4,965,188 | A | 10/1990 | Mullis |
| 5,002,882 | A | 3/1991 | Lunnen |
| 5,130,238 | A | 7/1992 | Malek |
| 5,308,751 | A | 5/1994 | Ohkawa |
| 5,321,130 | A | 6/1994 | Yue |

(Continued)

FOREIGN PATENT DOCUMENTS

| CN | 1680604 | 10/2005 |
| CN | 101221182 | 7/2008 |

(Continued)

OTHER PUBLICATIONS

Anacyte.com [online], "CellCover," 2022, retrieved on May 23, 2022, retrieved from URL<https://www.anacyte.com/>, 15 pages.

(Continued)

*Primary Examiner* — Kaijiang Zhang
(74) *Attorney, Agent, or Firm* — Fish & Richardson P.C.

(57) ABSTRACT

Provided herein are methods of identifying a methylation status of an analyte in a biological sample. Also provided herein are methods that combine identifying the methylation status with spatial technology to identify the location of a methylation status in a biological sample.

15 Claims, 24 Drawing Sheets

(56) References Cited

U.S. PATENT DOCUMENTS

| | | |
|---|---|---|
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,136,592 A | 10/2000 | Leighton |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,914,981 B2 | 3/2011 | Barany et al. |
| 7,955,794 B2 | 6/2011 | Shen et al. |
| 7,960,119 B2 | 6/2011 | Chee |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,278,034 B2 | 10/2012 | Muraca |
| 8,288,103 B2 | 10/2012 | Oliphant |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| 8,481,698 B2 | 7/2013 | Lieberman et al. |
| 8,507,204 B2 | 8/2013 | Pierce et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 9,005,891 B2 | 4/2015 | Sinicropi et al. |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,290,808 B2 | 3/2016 | Fodor |

(56) References Cited

U.S. PATENT DOCUMENTS

| | | |
|---|---|---|
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,376,716 B2 | 6/2016 | Van Eijk |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,273,541 B2 | 4/2019 | Hindson et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,633,648 B2 | 4/2020 | Seelig et al. |
| 10,724,078 B2 | 7/2020 | Van Driel et al. |
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbrueggen et al. |
| 10,913,975 B2 | 2/2021 | So et al. |
| 10,914,730 B2 | 2/2021 | Chee et al. |
| 10,927,403 B2 | 2/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,359,228 B2 | 6/2022 | Chee et al. |
| 2001/0055764 A1 | 12/2001 | Empendocles et al. |
| 2002/0040275 A1 | 4/2002 | Cravatt |
| 2002/0055100 A1 | 5/2002 | Kawashima |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |

(56) References Cited

U.S. PATENT DOCUMENTS

| | | |
|---|---|---|
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0258871 A1 | 10/2012 | Kozlov et al. |
| 2012/0289414 A1 | 11/2012 | Mitra et al. |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0333403 A1 | 11/2016 | Chee |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335410 A1 | 11/2017 | Driscoll et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0112261 A1 | 4/2018 | Van Driel et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0312822 A1 | 11/2018 | Lee et al. |
| 2019/0055594 A1 | 2/2019 | Samusik et al. |
| 2019/0085383 A1 | 3/2019 | Church et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0367969 A1 | 12/2019 | Belhocine et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |

(56) References Cited

U.S. PATENT DOCUMENTS

| | | | |
|---|---|---|---|
| 2021/0230681 A1 | 7/2021 | Patterson et al. | |
| 2021/0230692 A1 | 7/2021 | Daugharthy et al. | |
| 2021/0238664 A1 | 8/2021 | Bava et al. | |
| 2021/0238675 A1 | 8/2021 | Bava | |
| 2021/0238680 A1 | 8/2021 | Bava | |
| 2021/0247316 A1 | 8/2021 | Bava | |
| 2021/0255175 A1 | 8/2021 | Chee et al. | |
| 2021/0262018 A1 | 8/2021 | Bava et al. | |
| 2021/0262019 A1 | 8/2021 | Alvarado Martinez et al. | |
| 2021/0269864 A1 | 9/2021 | Chee | |
| 2021/0270822 A1 | 9/2021 | Chee | |
| 2021/0285036 A1 | 9/2021 | Yin et al. | |
| 2021/0285046 A1 | 9/2021 | Chell et al. | |
| 2021/0292748 A1 | 9/2021 | Frisen et al. | |
| 2021/0292822 A1 | 9/2021 | Frisen et al. | |
| 2021/0317510 A1 | 10/2021 | Chee et al. | |
| 2021/0317524 A1 | 10/2021 | Lucero et al. | |
| 2021/0324457 A1 | 10/2021 | Ramachandran Iyer et al. | |
| 2021/0332424 A1 | 10/2021 | Schnall-Levin | |
| 2021/0332425 A1 | 10/2021 | Pfeiffer et al. | |
| 2021/0348221 A1 | 11/2021 | Chell et al. | |
| 2022/0002791 A1 | 1/2022 | Frisen et al. | |
| 2022/0003755 A1 | 1/2022 | Chee | |
| 2022/0010367 A1 | 1/2022 | Ramachandran Iyer et al. | |
| 2022/0017951 A1 | 1/2022 | Ramachandran Iyer et al. | |
| 2022/0025446 A1 | 1/2022 | Shah | |
| 2022/0025447 A1 | 1/2022 | Tentori et al. | |
| 2022/0033888 A1 | 2/2022 | Schnall-Levin et al. | |
| 2022/0049293 A1 | 2/2022 | Frenz et al. | |
| 2022/0049294 A1 | 2/2022 | Uytingco et al. | |
| 2022/0064630 A1 | 3/2022 | Bent et al. | |
| 2022/0081728 A1 | 3/2022 | Williams | |
| 2022/0090058 A1 | 3/2022 | Frisen et al. | |
| 2022/0090175 A1 | 3/2022 | Uytingco et al. | |
| 2022/0090181 A1 | 3/2022 | Gallant et al. | |
| 2022/0098576 A1 | 3/2022 | Dadhwal | |
| 2022/0098661 A1 | 3/2022 | Chew et al. | |
| 2022/0106632 A1 | 4/2022 | Galonska et al. | |
| 2022/0106633 A1 | 4/2022 | Engblom et al. | |
| 2022/0112486 A1 | 4/2022 | Ramachandran Iyer et al. | |
| 2022/0112545 A1 | 4/2022 | Chee | |
| 2022/0119869 A1 | 4/2022 | Ramachandran Iyer et al. | |
| 2022/0127659 A1 | 4/2022 | Frisen et al. | |
| 2022/0127672 A1 | 4/2022 | Stoeckius | |
| 2022/0145361 A1 | 5/2022 | Frenz et al. | |
| 2022/0154255 A1 | 5/2022 | Chee et al. | |
| 2022/0170083 A1 | 6/2022 | Khaled et al. | |

FOREIGN PATENT DOCUMENTS

| | | | |
|---|---|---|---|
| CN | 108949924 | 12/2018 | |
| EP | 1782737 | 5/2007 | |
| EP | 1910562 | 4/2008 | |
| EP | 1923471 | 5/2008 | |
| EP | 2002017 | 12/2008 | |
| EP | 2292788 | 3/2011 | |
| EP | 2302070 | 3/2011 | |
| EP | 2881465 | 6/2015 | |
| EP | 3013984 | 5/2016 | |
| EP | 3511423 | 7/2019 | |
| EP | 3541956 | 9/2019 | |
| JP | 2007-014297 | 1/2007 | |
| JP | 2007-074967 | 3/2007 | |
| JP | 2009-036694 | 2/2009 | |
| WO | WO 1989/010977 | 11/1989 | |
| WO | WO 1991/006678 | 5/1991 | |
| WO | WO 1995/023875 | 9/1995 | |
| WO | WO 1995/025116 | 9/1995 | |
| WO | WO 1995/035505 | 12/1995 | |
| WO | WO 1997/031256 | 8/1997 | |
| WO | WO 1999/044062 | 9/1999 | |
| WO | WO 1999/044063 | 9/1999 | |
| WO | WO 2000/17390 | 3/2000 | |
| WO | WO 2001/06012 | 1/2001 | |
| WO | WO 2001/009363 | 2/2001 | |
| WO | WO 2001/042796 | 6/2001 | |
| WO | WO 2001/090415 | 11/2001 | |
| WO | WO 2001/096608 | 12/2001 | |
| WO | WO 2002/059355 | 8/2002 | |
| WO | WO 2002/059364 | 8/2002 | |
| WO | WO 2002/077283 | 10/2002 | |
| WO | WO 2003/002979 | 1/2003 | |
| WO | WO 2003/008538 | 1/2003 | |
| WO | WO 2003/010176 | 2/2003 | |
| WO | WO 2003/102233 | 12/2003 | |
| WO | WO 2004/015080 | 2/2004 | |
| WO | WO 2004/067759 | 8/2004 | |
| WO | WO 2005/007814 | 1/2005 | |
| WO | WO 2005/010145 | 2/2005 | |
| WO | WO 2005/026387 | 3/2005 | |
| WO | WO 2005/042759 | 5/2005 | |
| WO | WO 2005/113804 | 12/2005 | |
| WO | WO 2006/020515 | 2/2006 | |
| WO | WO 2006/124771 | 11/2006 | |
| WO | WO 2007/041689 | 4/2007 | |
| WO | WO 2007/060599 | 5/2007 | |
| WO | WO 2007/073171 | 6/2007 | |
| WO | WO 2007/076726 | 7/2007 | |
| WO | WO 2007/139766 | 12/2007 | |
| WO | WO 2007/145612 | 12/2007 | |
| WO | WO 2008/069906 | 6/2008 | |
| WO | WO 2009/032167 | 3/2009 | |
| WO | WO 2009/152928 | 12/2009 | |
| WO | WO 2010/019826 | 2/2010 | |
| WO | WO 2010/027870 | 3/2010 | |
| WO | WO 2010/126614 | 11/2010 | |
| WO | WO 2011/008502 | 1/2011 | |
| WO | WO 2011/062933 | 5/2011 | |
| WO | WO 2011/068088 | 6/2011 | |
| WO | WO 2012/049316 | 4/2012 | |
| WO | WO 2012/071428 | 5/2012 | |
| WO | WO 2012/129242 | 9/2012 | |
| WO | WO 2012/159089 | 11/2012 | |
| WO | WO 2013/123442 | 8/2013 | |
| WO | WO 2013/138510 | 9/2013 | |
| WO | WO 2013/142389 | 9/2013 | |
| WO | WO 2013/150083 | 10/2013 | |
| WO | WO 2014/044724 | 3/2014 | |
| WO | WO 2014/144713 | 9/2014 | |
| WO | WO 2014/152397 | 9/2014 | |
| WO | WO 2014/210223 | 12/2014 | |
| WO | WO 2014/210225 | 12/2014 | |
| WO | WO 2015/161173 | 10/2015 | |
| WO | WO 2016/138496 | 9/2016 | |
| WO | WO 2016/138500 | 9/2016 | |
| WO | WO 2016/166128 | 10/2016 | |
| WO | WO 2016/168825 | 10/2016 | |
| WO | WO 2016/172362 | 10/2016 | |
| WO | WO 2017/019456 | 2/2017 | |
| WO | WO 2017/019481 | 2/2017 | |
| WO | WO-2017019456 A2 * | 2/2017 | ........... C12Q 1/6816 |
| WO | WO 2017/075293 | 5/2017 | |
| WO | WO 2017/096158 | 7/2017 | |
| WO | WO 2017/124101 | 7/2017 | |
| WO | WO 2017/156336 | 9/2017 | |
| WO | WO 2017/184984 | 10/2017 | |
| WO | WO 2017/192633 | 11/2017 | |
| WO | WO 2018/023068 | 2/2018 | |
| WO | WO 2018/045181 | 3/2018 | |
| WO | WO 2018/064640 | 4/2018 | |
| WO | WO 2018/085599 | 5/2018 | |
| WO | WO 2018/091676 | 5/2018 | |
| WO | WO 2018/136856 | 7/2018 | |
| WO | WO 2018/144582 | 8/2018 | |
| WO | WO 2018/209398 | 11/2018 | |
| WO | WO 2019/023214 | 1/2019 | |
| WO | WO 2019/032760 | 2/2019 | |
| WO | WO 2019/068880 | 4/2019 | |
| WO | WO 2019/113457 | 6/2019 | |
| WO | WO 2019/126313 | 6/2019 | |
| WO | WO-2019126313 A1 * | 6/2019 | ............... C12Q 1/68 |
| WO | WO 2019/140201 | 7/2019 | |
| WO | WO 2019/165318 | 8/2019 | |
| WO | WO 2019/213254 | 11/2019 | |

(56) References Cited

FOREIGN PATENT DOCUMENTS

| | | |
|---|---|---|
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/112604 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/091611 | 5/2021 |
| WO | WO 2021/092433 | 5/2021 |
| WO | WO 2021/097255 | 5/2021 |
| WO | WO 2021/119320 | 6/2021 |
| WO | WO 2021/133849 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2022/025965 | 2/2022 |
| WO | WO 2022/060798 | 3/2022 |
| WO | WO 2022/060953 | 3/2022 |
| WO | WO 2022/087273 | 4/2022 |
| WO | WO 2022/098810 | 5/2022 |
| WO | WO 2022/099037 | 5/2022 |
| WO | WO 2022/109181 | 5/2022 |

OTHER PUBLICATIONS

Biolegend.com [online], "Microscopy," 2022, retrieved on May 23, 2022, retrieved from URL<https://www.biolegend.com/en-us/microscopy#applications-fivecolorfluorescencemiscroscopy>, 4 pages.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Lou et al., "A review of room temperature storage of biospecimen tissue and nucleic acids for anatomic pathology laboratories and biorepositories," Clin Biochem., Mar. 2014, 47(4-5):267-73.

Lykidis et al., "Novel zinc-based fixative for high quality DNA, RNA and protein analysis," Nucleic Acids Res., Jun. 2007, 35(12):e85, 10 pages.

Madissoon et al., "scRNA-seq assessment of the human lung, spleen, and esophagus tissue stability after cold preservation," Genome Biol., Dec. 2019, 21(1):1, 16 pages.

Nadji et al., "Immunohistochemistry of tissue prepared by a molecular-friendly fixation and processing system," Appl Immunohistochem Mol Morphol., Sep. 2005, 13(3):277-82.

Passow et al., "RNAlater and flash freezing storage methods nonrandomly influence observed gene expression in RNAseq experiments," bioRxiv, Jul. 2018, 28 pages.

Porreca et al., "Polony DNA sequencing," Curr Protoc Mol Biol., Nov. 2006, Chapter 7, Unit 7.8, pp. 7.8.1-7.8.22.

Wohnhaas et al., "DMSO cryopreservation is the method of choice to preserve cells for droplet-based single-cell RNA sequencing," Scientific Reports, Jul. 2019, 9(1):10699, 14 pages.

Al-Ani et al., "Oxygenation in cell culture: Critical parameters for reproducibility are routinely not reported," PLoS One, Oct. 2018, 13(10):e0204269, 13 pages.

Chen et al., "Gray-scale photolithography using microfluidic photomasks," PNAS, Feb. 2003, 100(4):1499-1504.

Dalma-Weiszhausz et al., "The affymetrix GeneChip platform: an overview," Methods Enzymol., 2006, 410:3-28.

Ebihara et al., "Molecular detection of dermatophytes and nondermatophytes in onychomycosis by nested polymerase chain reaction based on 28S ribosomal RNA gene sequences," Br J Dermatol., Nov. 2009, 161(5):1038-44.

Escholarship.org [online], "Methods and devices for fabricating and assembling DNA and protein arrays for high-throughput analyses [electronic resource]," 2010, retrieved on Jun. 8, 2022, retrieved from URL<https://escholarship.org/uc/item/6tf7p46s>, 155 pages.

Fischer et al., "Hematoxylin and eosin staining of tissue and cell sections," CSH Protoc., May 2008, 3(5):1-3.

Jennane et al., "Photolithography of self-assembled monolayers: optimization of protecting groups by an electroanalytical method," Can. J Chem., Dec. 1996, 74(12):2509-2517.

Lahiani et al., "Enabling Histopathological Annotations on Immunofluorescent Images through Virtualization of Hematoxylin and Eosin," J Pathol Inform., Feb. 2018, 9:1, 8 pages.

Miller et al., "Chapter 11—Solid and Suspension Microarrays for Microbial Diagnostics," Methods in Microbiology, 2015, 42:395-431.

Ren et al., "Star Polymers," Chem Rev., Jun. 2016, 116(12):6743-836.

Totet et al., "Immunocompetent infants as a human reservoir for Pneumocystis jirovecii: rapid screening by non-invasive sampling and real-time PCR at the mitochondrial large subunit rRNA gene," J Eukaryot Microbiol., 2003, pp. 668-669.

Vickovic et al., "SM-Omics: An automated Platform for High-Throughput Spatial Multi-Omics," bioRxiv, Oct. 2020, 40 pages.

U.S. Appl. No. 60/416,118, filed Oct. 3, 2002, Fan et al.

U.S. Appl. No. 61/267,363, filed Dec. 7, 2009, Fan et al.

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual," Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

[No Author Listed], "Proseek® Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8fl500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/

(56) References Cited

OTHER PUBLICATIONS

3GGIfH3RWpdlbFVhalpexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 70 pages.

10xGenomics.com, [online],"Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8fl500aba503005a04a56/CG000238_VisiumSpatialTissueOptimizationUserGuide_RevD.pdf>, 42 pages.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Agilent.com [online], "The First Comprehensive Methylation Discovery System," Dec. 2015, retrieved on Jan. 21, 2022, retrieved from URL<https://www.agilent.com/cs/library/datasheets/Public/SureselectXTHumanMethyl-Seq-5990-9856EN.pdf>, 2 pages.

Alam, "Proximity Ligation Assay (PLA)," Curr Protoc Immunol., Nov. 2018, 123(1):e58, 8 pages.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Allawi et al., "Thermodynamics and NMR of Internal GâT Mismatches in DNA," Biochemistry, 1996, 36(34):10581-10594.

Andresen et al., "Helicase-dependent amplification: use in OnChip amplification and potential for point-of-care diagnostics," Expert Rev Mol Diagn., Oct. 2009, 9(7):645-650.

Aran et al., "xCell: digitally portraying the tissue cellular heterogeneity landscape," Genome Biol., Nov. 2017, 18(1):220, 14 pages.

Archer et al., "Selective and flexible depletion of problematic sequences from RNA-seq libraries at the cDNA stage," BMC Genomics, May 2014, 15(1):401, 9 pages.

Armani et al., "2D-PCR: a method of mapping DNA in tissue sections," Lab Chip, 2009, 9(24):3526-34.

Atkinson et al., "An Updated Protocol for High Throughput Plant Tissue Sectioning," Front Plant Sci, 2017, 8:1721, 8 pages.

Atkinson, "Overview of Translation: Lecture Manuscript," U of Texas, 2000, DD, pp. 6.1-6.8.

Bains et al., "A novel method for nucleic acid sequence determination," Journal of Theoretical Biology, 1988, 135(3), 303-7.

Barnes, "PCR amplification of up to 35-kb DNA with high fidelity and high yield from lambda bacteriophage templates," Proc. Natl. Acad. Sci USA, 1994, 91(6):2216-2220.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.

Bartosovic et al., "Single-cell CUT&Tag profiles histone modifications and transcription factors in complex tissues," Nat Biotechnol., Jul. 2021, 39(7):825-835, Abstract.

Baugh et al., "Quantitative analysis of mRNA amplification by in vitro transcription," Nucleic Acids Res., 2001, 29(5):e29, 9 pages.

Beattie et al., "Advances in genosensor research," Clin Chem., May 1995, 41(5):700-6.

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

Bell, "A simple way to treat PCR products prior to sequencing using ExoSAP-IT," Biotechniques, 2008, 44(6):834, 1 page.

Bentley et al., "Accurate whole human genome sequencing using reversible terminator chemistry," Nature, 2008, 456(7218):53-59.

Birney et al., "Identification and analysis of functional elements in 1% of the human genome by the ENCODE pilot project," Nature, 2007, 447(7146):799-816.

Blanchard et al., "High-density oligonucleotide arrays," Biosensors & Bioelectronics, 1996, 11(6-7):687-690.

Blanco et al., "A practical approach to FRET-based PNA fluorescence in situ hybridization," Methods, Dec. 2010, 52(4):343-51.

Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.

Bolognesi et al., "Multiplex Staining by Sequential Immunostaining and Antibody Removal on Routine Tissue Sections," J. Histochem. Cytochem., Aug. 2017, 65(8):431-444.

Brandon et al., "Mitochondrial mutations in cancer," Oncogene, 2006, 25(34):4647-4662.

Brenner et al., "Gene expression analysis by massively parallel signature sequencing (MPSS) on microbead arrays," Nat. Biotech., 2000, 18(6):630-634.

Brenner et al., "In vitro cloning of complex mixtures of DNA on microbeads: physical separation of differentially expressed cDNAs," Proc. Natl. Acad. Sci. USA, 2000, 97(4):1665-1670.

Brow, "35—The Cleavase I enzyme for mutation and polymorphism scanning," PCR Applications Protocols for Functional Genomics, 1999, pp. 537-550.

Brown et al., "Retroviral integration: structure of the initial covalent product and its precursor, and a role for the viral IN protein," Proc Natl Acad Sci USA, Apr. 1989, 86(8):2525-9.

Buenrostro et al., "Transposition of native chromatin for multimodal regulatory analysis and personal epigenomics," Nat Methods, Dec. 2013, 10(12):1213-1218.

Bullard et al., "Direct comparison of nick-joining activity of the nucleic acid ligases from bacteriophage T4," Biochem. J. 2006, 398(1):135-144.

Burgess, "A space for transcriptomics," Nature Reviews Genetics, 2016, 17(8):436-7.

Burgess, "Finding structure in gene expression," Nature Reviews Genetics, 2018, 19(5):249, 1 page.

Burton et al., "Coverslip Mounted-Immersion Cycled in Situ RT-PCR for the Localization of mRNA in Tissue Sections," Biotechniques, 1998, 24(1):92-100.

Carter et al., "Stabilization of an optical microscope to 0.1 nm in three dimensions," Applied Optics, 2007, 46:421-427.

Cha et al., "Specificity, efficiency, and fidelity of PCR," Genome Res., 1993, 3(3):S18-29.

Chandra et al., "Cell-free synthesis-based protein microarrays and their applications," Proteomics, 2009, 5(6):717-30.

Chatterjee et al., "Mitochondrial DNA mutations in human cancer. Oncogene," 2006, 25(34):4663-4674.

Chen et al., "DNA hybridization detection in a microfluidic Channel using two fluorescently labelled nucleic acid probes," Biosensors and Bioelectronics, 2008, 23(12):1878-1882.

Chen et al., "Expansion microscopy," Science, 2015, 347(6221):543-548.

Chen et al., "Nanoscale imaging of RNA with expansion microscopy," Nat Methods, Aug. 2016, 13(8):679-84.

Chen et al., "RNA imaging. Spatially resolved, highly multiplexed RNA profiling in single cells," Science, Apr. 2015, 348(6233):aaa6090, 21 pages.

Chen et al., "Spatial Transcriptomics and In Situ Sequencing to Study Alzheimer's Disease," Cell, Aug. 2020, 182(4):976-991.

Chen et al., "Spatially resolved, highly multiplexed RNA profiling in single cells," Science, 2015, 348(6233):aaa6090, 21 pages.

(56) References Cited

OTHER PUBLICATIONS

Chen et al., "μCB-seq: microfluidic cell barcoding and sequencing for high-resolution imaging and sequencing of single cells," Lab Chip, Nov. 2020, 20(21):3899-3913.
Chen et al., "ATAC-see reveals the accessible genome by transposase-mediated imaging and sequencing," Nature Methods, Dec. 2016, 13(12):1013-1020.
Chrisey et al., "Covalent attachment of synthetic DNA to self-assembled monolayer films," Nucleic Acids Res., Aug. 1996, 24(15):3031-9.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.

Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Galleri.com [online], "Multi-cancer early detection through a simple blood draw," 2022, retrieved on Jan. 21, 2022, retrieved from URL<https://www.galleri.com/hcp/the-galleri-test>, 5 pages.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL<https://web.archive.org/web/20150214084616/http://genearrays.com/services/microarrays/illumina/beadarray-technology/>, [retrieved on Jan. 30, 2020], 3 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hahnke et al., "Striptease on glass: validation of an improved stripping procedure for in situ microarrays," J Biotechnol., Jan. 2007, 128(1):1-13.

(56) References Cited

OTHER PUBLICATIONS

Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hein et al., "Click Chemistry, A Powerful Tool for Pharmaceutical Sciences," Pharm Res, 2008, 25(10): 2216-2230.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Kolb et al., "Click Chemistry: Diverse Chemical Function from a Few Good Reactions," Angew. Chem. Int. Ed., Jun. 2001, 40(11):2004-2021.
Korbel et al., "Paired-end mapping reveals extensive structural variation in the human genome," Science, 2007, 318(5849):420-426.

Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA-protein fusions: covalent protein-gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "Methylation extends the reach of liquid biopsy in cancer detection," Nat Rev Clin Oncol., Nov. 2020, 17(11):655-656.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Locke et al., "DNA Methylation Cancer Biomarkers: Translation to the Clinic," Front Genet., Nov. 2019, 10:1150, 22 pages.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.

(56) References Cited

OTHER PUBLICATIONS

Lundberg et al., "Homogeneous antibody-based proximity extension assays provide sensitive and specific detection of low-abundant proteins in human blood," Nucleic Acids Res., 2011, 39(15):e102, 8 pages.

Lundberg et al., "Multiplexed homogeneous proximity ligation assays for high-throughput protein biomarker research in serological material," Mol Cell Proteomics, 2011, 10(4):M110.004978, 11 pages.

Lundin et al., "Increased throughput by parallelization of library preparation for massive sequencing," PLoS One, Apr. 2010, 5(4):e10029, 7 pages.

Lyck et al., "Immunohistochemical markers for quantitative studies of neurons and glia in human neocortex," J Histochem Cytochem, 2008, 56(3):201-21.

MacBeath et al., "Printing proteins as microarrays for high-throughput function determination," Science, Sep. 2000, 289(5485):1760-1763.

MacIntyre, "Unmasking antigens for immunohistochemistry.," Br J Biomed Sci., 2001, 58(3):190-6.

Marx, "Method of the Year: spatially resolved transcriptomics," Nature Methods, 2021, 18(1):9-14.

May, "Catching cancer extremely early," Science, Mar. 2021, 8 pages.

McCloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miele et al., "Mapping cis- and trans-chromatin interaction networks using chromosome conformation capture (3C)," Methods Mol Biol., 2009, 464:105-21.

Miller et al., "Basic concepts of microarrays and potential applications in clinical microbiology," Clinical Microbiology Reviews, 2009, 22(4):611-633.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Mizusawa et al., "A bacteriophage lambda vector for cloning with BamHI and Sau3A," Gene, 1982, 20(3):317-322.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Mukherjee et al., "Insects as models to study the epigenetic basis of disease," Prog Biophys Mol Biol., Jul. 2015, 118(1-2):69-78.

Nandakumar et al., "How an RNA Ligase Discriminates RNA versus DNA Damage," Molecular Cell, 2004, 16:211-221.

Nassiri et al., "Detection and discrimination of intracranial tumors using plasma cell-free DNA methylomes," Nat Med., Jul. 2020, 26(7):1044-1047.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Nikiforov et al., "The use of 96-well polystyrene plates for DNA hybridization-based assays: an evaluation of different approaches to oligonucleotide immobilization," Anal Biochem, May 1995, 227(1):201-9.

Niklas et al., "Selective permeabilization for the high-throughput measurement of compartmented enzyme activities in mammalian cells," Anal Biochem, Sep. 2011, 416(2):218-27.

Nowak et al., "Entering the Postgenome Era," Science, 1995, 270(5235):368-71.

Nuzzo et al., "Detection of renal cell carcinoma using plasma and urine cell-free DNA methylomes," Nat Med., Jul. 2020, 26(7):1041-1043.

Ohtsubo et al., "Bacterial insertion sequences," Curr Top Microbiol Immunol., 1996, 204:1-26.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger microwells capable of supporting cell spreading and proliferation," Microfluid Nanofluid, 2010, 8:263-268.

PCT International Search Report and Written Opinion in International Appln. No. PCT/US2021/039103, dated Nov. 5, 2021, 14 pages.

Pellestor et al., "The peptide nucleic acids (PNAs), powerful tools for molecular genetics and cytogenetics," Eur J Hum Genet., Sep. 2004, 12(9):694-700.

Pemov et al., "DNA analysis with multiplex microarray-enhanced PCR," Nucl. Acids Res., Jan. 2005, 33(2):e11, 9 pages.

Perler et al., "Intervening sequences in an Archaea DNA polymerase gen," Proc Natl Acad Sci USA, Jun. 1992, 89(12):5577-5581.

Petterson et al., "Generations of sequencing technologies," Genomics, 2009, 93(2):105-111.

Picelli et al., "Tn5 transposase and tagmentation procedures for massively scaled sequencing projects," Genome Res., Dec. 2014, 24(12):2033-40.

Pipenburg et al., "DNA detection using recombination proteins," PLoS Biol., Jul. 2006, 4(7):e204, 7 pages.

Pirici et al., "Antibody elution method for multiple immunohistochemistry on primary antibodies raised in the same species and of the same subtypem," J. Histochem. Cytochem., Jun. 2009, 57(6):567-75.

Plasterk, "The Tc1/mariner transposon family," Curr Top Microbiol Immunol., 1996, 204:125-43.

Plongthongkum et al., "Advances in the profiling of DNA modifications: cytosine methylation and beyond," Nature Reviews Genetics, Aug. 2014, 15(10):647-661.

Polsky-Cynkin et al., "Use of DNA immobilized on plastic and agarose supports to detect DNA by sandwich hybridization," Clin. Chem., 1985, 31(9):1438-1443.

U.S. Appl. No. 61/267,363, filed Dec. 7, 2009, 33 pages.

Raab et al., "Human tRNA genes function as chromatin insulators," EMBO J., Jan. 2012, 31(2):330-50.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Reznikoff, "Tn5 as a model for understanding DNA transposition," Mol Microbiol., Mar. 2003, 47(5):1199-206.

Ristic et al., "Detection of Protein-Protein Interactions and Post-translational Modifications Using the Proximity Ligation Assay: Application to the Study of the SUMO Pathway," Methods Mol. Biol., 2016, 1449:279-90.

Rodriques et al., "Slide-seq: A scalable technology for measuring genome-wide expression at high spatial resolution," Science, 2019, 363(6434):1463-1467.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

(56) References Cited

OTHER PUBLICATIONS

Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schweitzer et al., "Multiplexed protein profiling on microarrays by rolling-circle amplification," Nature Biotechnology, Apr. 2002, 20(4):359-365.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "Tagmentation-based whole-genome bisulfite sequencing," Nature Protocols, Oct. 2013, 8(10):2022-2032.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al, "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.

(56) References Cited

OTHER PUBLICATIONS

Zhang et al., "Archaeal RNA ligase from thermoccocus kodakarensis for template dependent ligation," RNA Biol., Jan. 2017, 14(1):36-44.

Zhang et al., "Assembling DNA through Affinity Binding to Achieve Ultrasensitive Protein Detection," Angew Chem Int Ed Engl., 2013, 52(41):10698-705.

Zhang et al., "Binding-induced DNA assembly and its application to yoctomole detection of proteins," Anal Chem, 2012, 84(2):877-884.

Zhang et al., "Multiplex ligation-dependent probe amplification (MLPA) for ultrasensitive multiplexed microRNA detection using ribonucleotide-modified DNA probes†," Chem. Commun., 2013, 49:10013-10015.

Zheng et al., "Origins of human mitochondrial point mutations as DNA polymerase gamma-mediated errors," Mutat. Res., 2006, 599(1-2):11-20.

Zhou et al., "Genetically encoded short peptide tags for orthogonal protein labeling by Sfp and AcpS phosphopantetheinyl transferases," ACS Chemical Biol., 2007, 2(5):337-346.

Zhu et al., "Reverse transcriptase template switching: a SMART approach for full-length cDNA library construction," Biotechniques, Apr. 2001, 30(4):892-897.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.

Hamaguchi et al., "Direct reverse transcription-PCR on oligo(dT)-immobilized polypropylene microplates after capturing total mRNA from crude cell lysates," Clin Chem., Nov. 1998, 44(11):2256-63.

Ke et al., "In situ sequencing for RNA analysis in preserved tissue and cells," Nat Methods., Sep. 2013, Supplementary Materials, 29 pages.

Miner et al., "Molecular barcodes detect redundancy and contamination in hairpin-bisulfite PCR," Nucleic Acids Res., Sep. 2004, 32(17):e135, 4 pages.

Asp et al., "Spatially Resolved Transcriptomes—Next Generation Tools for Tissue Exploration," Bioessays, Oct. 2020, 42(10):e1900221, 16 pages.

Balakrishnan et al., "Flap endonuclease 1," Annu Rev Biochem., Jun. 2013, 82:119-138.

Bergenstråhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15):2911-2914.

Blair et al., "Microarray temperature optimization using hybridization kinetics," Methods Mol Biol., 2009, 529:171-96.

Bolotin et al., "MiXCR: software for comprehensive adaptive immunity profiling," Nat Methods., May 2015, 12(5):380-1.

Chen et al., "Parallel single nucleotide polymorphism genotyping by surface invasive cleavage with universal detection," Anal Chem., Apr. 2005, 77(8):2400-5.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Ciaccio et al., "Systems analysis of EGF receptor signaling dynamics with microwestern arrays," Nat Methods, Feb. 2010, 7(2):148-55.

Gerard et al., "Excess dNTPs minimize RNA hydrolysis during reverse transcription," Biotechniques, Nov. 2002, 33(5):984, 986, 988, 990.

Hessner et al., "Genotyping of factor V G1691A (Leiden) without the use of PCR by invasive cleavage of oligonucleotide probes," Clin Chem., Aug. 2000, 46(8 Pt 1):1051-6.

Hoffman et al., "Formaldehyde crosslinking: a tool for the study of chromatin complexes," J Biol Chem., Oct. 2015, 290(44):26404-11.

Hughes et al., "Microfluidic Western blotting," PNAS, Dec. 2012, 109(52):21450-21455.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Nilsson et al., "RNA-templated DNA ligation for transcript analysis," Nucleic Acids Res., Jan. 2001, 29(2):578-81.

Olivier, "The Invader assay for SNP genotyping," Mutat. Res., Jun. 2005, 573(1-2):103-110.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Picelli et al., "Full-length RNA-seq from single cells using Smart-seq2," Nat Protoc., Jan. 2014, 9(1):171-81.

Schouten et al., "Relative quantification of 40 nucleic acid sequences by multiplex ligation-dependent probe amplification," Nucleic Acids Res., Jun. 2002, 30(12):e57, 13 pages.

Singh et al., "High-throughput targeted long-read single cell sequencing reveals the clonal and transcriptional landscape of lymphocytes," Nat Commun., Jul. 2019, 10(1):3120, 13 pages.

Sountoulidis et al., "SCRINSHOT, a spatial method for single-cell resolution mapping of cell states in tissue sections," PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

Sutherland et al., "Utility of formaldehyde cross-linking and mass spectrometry in the study of protein-protein interactions," J. Mass Spectrom., Jun. 2008, 43(6):699-715.

Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

Tu et al., "TCR sequencing paired with massively parallel 3' RNA-seq reveals clonotypic T cell signatures," Nature Immunology, Dec. 2019, 20(12):1692-1699.

Vázquez Bernat et al., "High-Quality Library Preparation for NGS-Based Immunoglobulin Germline Gene Inference and Repertoire Expression Analysis," Front Immunol., Apr. 2019, 10:660, 12 pages.

Wu et al., "RollFISH achieves robust quantification of single-molecule RNA biomarkers in paraffin-embedded tumor tissue samples," Commun Biol., Nov. 2018, 1:209, 8 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.

Niedringhaus et al., "Landscape of next-generation sequencing technologies," Anal Chem., Jun. 2011, 83(12):4327-41.

(56) References Cited

OTHER PUBLICATIONS

Qiu et al., "Combination probes with intercalating anchors and proximal fluorophores for DNA and RNA detection," Nucleic Acids Research, Sep. 2016, 44(17):e138, 12 pages.

Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.

Zhao et al., "Isothermal Amplification of Nucleic Acids," Chemical Reviews, Nov. 2015, 115(22):12491-12545.

* cited by examiner

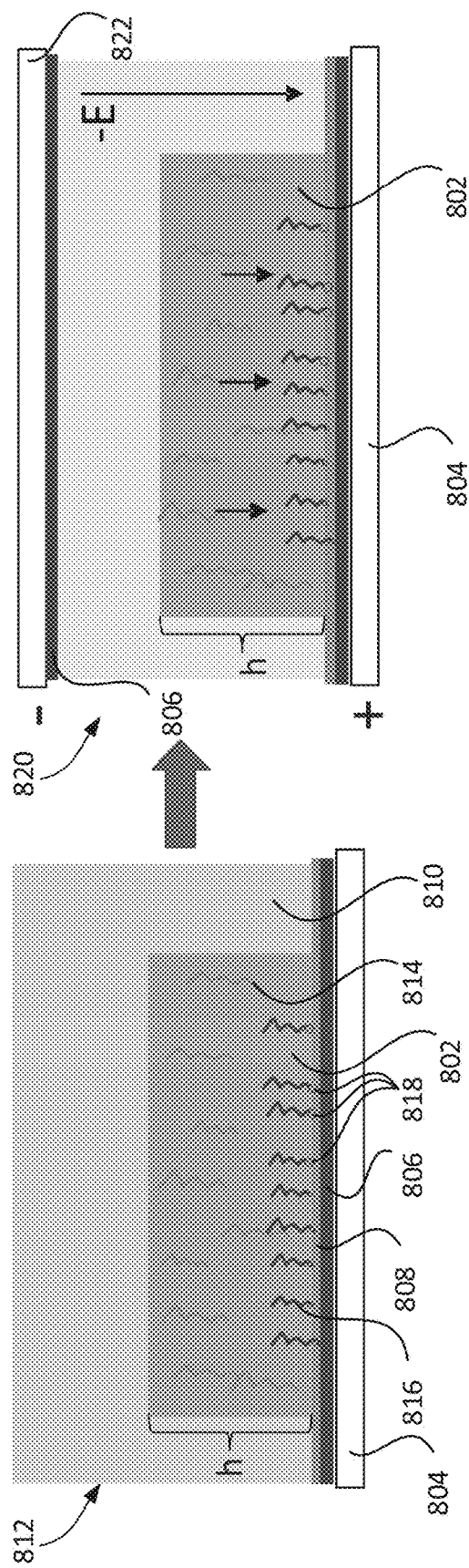
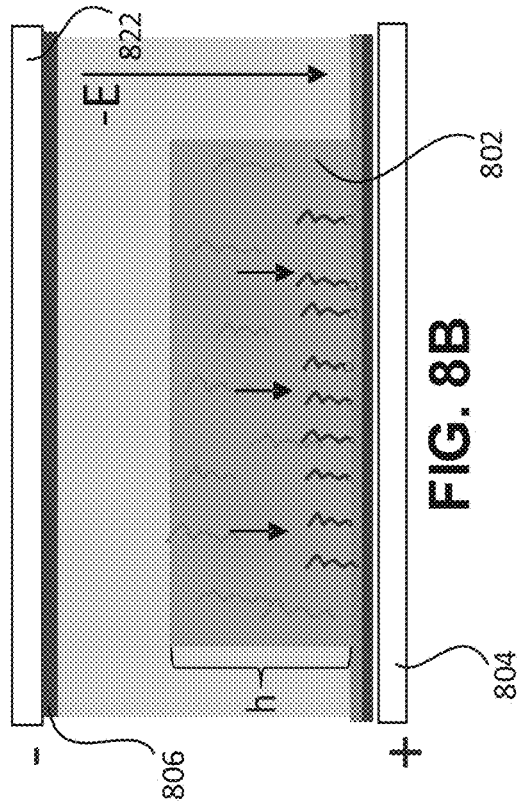
FIG. 8A
FIG. 8B

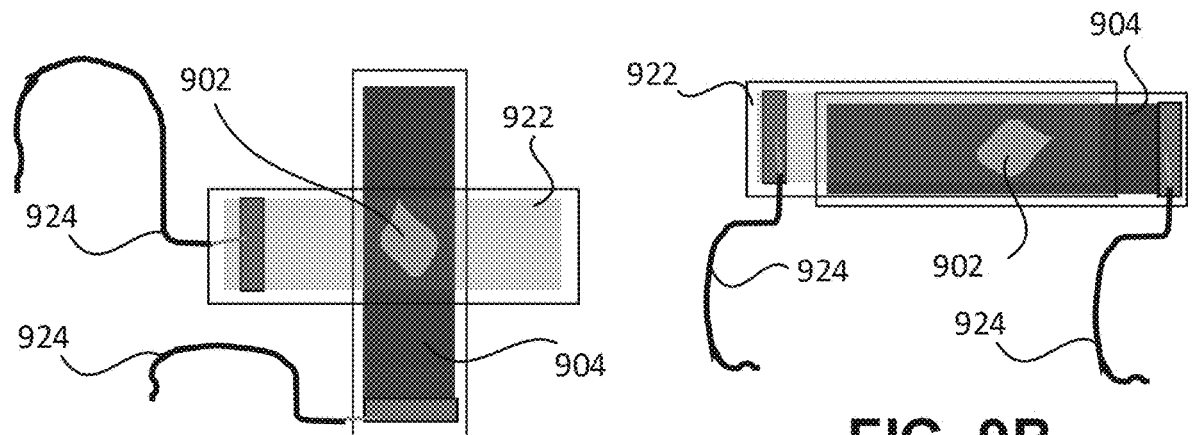
FIG. 9A
FIG. 9B
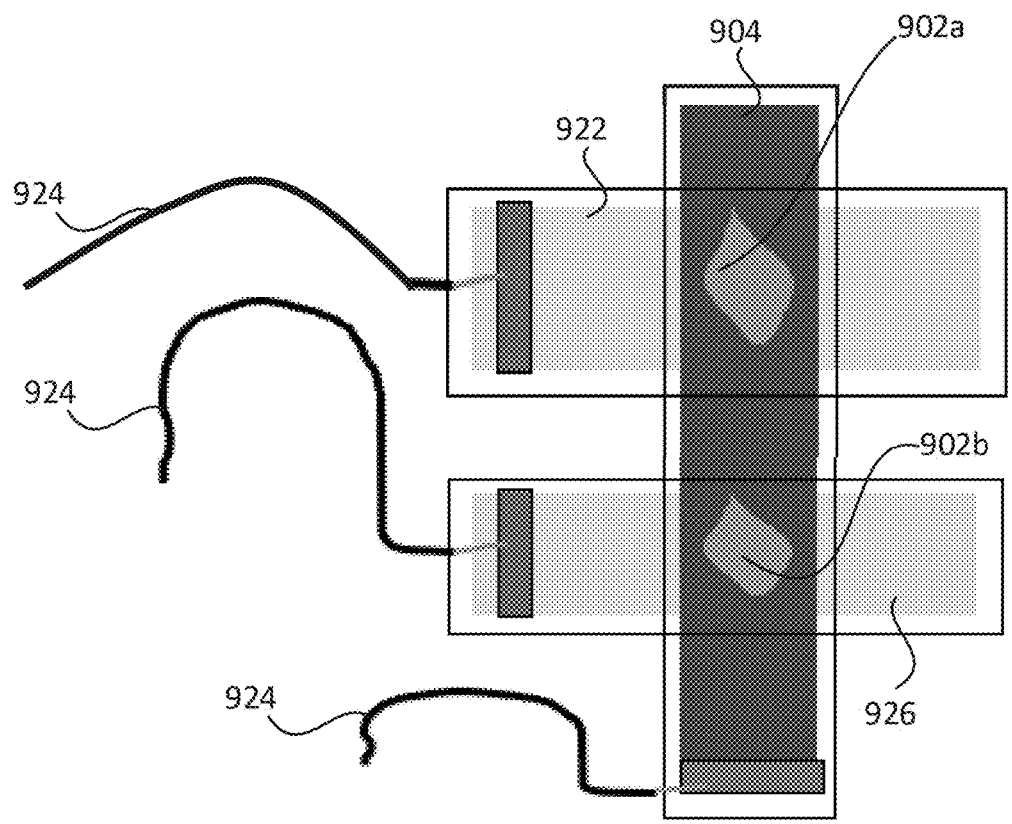
FIG. 9C

| Analysis ID | Sample | Description | Permeabilization time | mm10 Median genes per spot (30k raw reads per spot) | mm10 Median umi counts per spot (30k raw reads per spot) |
|---|---|---|---|---|---|
| 1046321 | Mouse Brain (FF) | Single-slide control | 5 minutes | 5194 | 17660 |
| 1046322 | | | | 4592 | 13083 |
| 1046514 | | Permeabilization in two-slide assembly | 1 minute | 4072 | 14017 |
| 1046515 | | | | 3758 | 13731 |

SPATIAL ANALYSIS OF DNA METHYLATION

CROSS-REFERENCE TO RELATED APPLICATION

Pursuant to 35 U.S.C. § 119(e), this application is a continuation of International Application PCT/US2021/039103, with an international filing date of Jun. 25, 2021, which claims priority to U.S. Provisional Patent Application No. 63/044,042, filed Jun. 25, 2020, and U.S. Provisional Patent Application No. 63/128,783, filed Dec. 21, 2020. The entire contents of the foregoing applications are incorporated herein by reference.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

DNA methylation is a crucial epigenetic modification of the genome that is involved in regulating many cellular processes. These processes include, but are not limited to, embryonic development, transcription, chromosome activation, chromosomal stability and as such DNA methylation, and also aberrant DNA methylation, has been associated with human diseases.

DNA methylation is an epigenetic mark that can be inherited through multiple cell divisions. However, changes in methylation status can also occur in a single cell (e.g., a cancer cell). Thus, in a pathological setting, the methylation state of each DNA molecule can vary, making its analysis challenging and cumbersome. This is further confounded by the fact that methylated-cytosine bases are not distinguishable from unmethylated-cytosine bases in standard DNA sequencing technologies. To study DNA methylation, many researchers rely on the use of bisulfite: a chemical which converts unmethylated cytosines to thymines and leaves methylated cytosines intact. Ideally, bisulfite conversion could be used for single-cell technologies, however, the chemical is harsh, fragments DNA, and is often not compatible with enzymes and reagents required in downstream steps. However, due to the diagnostic and therapeutic implications related to targeting DNA methylation, there remains a need to develop reliable and cost-effective methods to ascertain the methylation status of nucleic acids at spatial locations of a biological sample.

SUMMARY

This disclosure provides methods of spatial analysis with identification of DNA methylation status. The methods provided herein are applicable to normal physiological conditions, development and stem-cell studies, and in pathophysiological settings such as cancer. For example, in one embodiment, the DNA methylation status (and changes of the same) of one or more particular analytes can be examined during therapeutic delivery. And, because the location of the analyte (or complement thereof) can be identified using spatial analysis methods (e.g., RNA-templated ligation) as disclosed herein, the location of the analyte and/or changes to the methylation status can be identified. In some instances, the methods disclosed herein can also be combined with imaging techniques that provide a correlation between a particular location of an image (e.g., location of a tumor in a biological sample) and both gene expression and methylation status at that location. Thus, the disclosure provides powerful methods of identifying the location of methylated DNA in a biological sample.

Accordingly, described herein is a method for identifying methylation status of an analyte in a biological sample, the method comprising: (a) contacting the biological sample with an array comprising a plurality of capture probes, wherein a capture probe in the plurality of capture probes comprises (i) a spatial barcode and (ii) a capture domain comprising at least one methylated cytosine; (b) deaminating the analyte in the biological sample; (c) contacting the analyte with a plurality of probes comprising a first probe and a second probe, wherein the first probe comprises (i) a sequence complementary to at least a first sequence of the analyte and (ii) a sequence complementary to the capture domain; and the second probe comprises a sequence complementary to at least a second sequence of the analyte; (d) ligating the first probe and the second probe, thereby generating a ligation product; (e) hybridizing the ligation product to the capture probe; (f) extending the capture probe using the ligation product as a template; thereby generating an extended capture probe; and (g) determining (i) all or a portion of the sequence of the spatial barcode or the complement thereof, and (ii) all or a portion of the sequence of the extended capture probe, or a complement thereof, and using the determined sequences of (i) and (ii) to identify the methylation status of the analyte in the biological sample.

In some embodiments, the first oligonucleotide and the second oligonucleotide hybridize to the analyte at sequences that are at least about 1, 2, 3, 4, 5, 6, 7, 8, 9, 10, or more nucleotides apart.

In some embodiments, the method described herein further comprises extending the first oligonucleotide and/or the second oligonucleotide after step (c). In some embodiments, the first probe and/or second probe is extended using a polymerase.

In some embodiments, the method described herein further comprises releasing the ligation product from the analyte. In some embodiments, the releasing occurs before hybridizing the ligation product to the capture probe.

In some embodiments, the method further comprises, prior to step (b), contacting the biological sample with a permeabilization reagent.

In some embodiments, the first probe and/or the second probe comprises a sequence that binds to a sequence on the analyte that does not have a CG dinucleotide.

In some embodiments, the method further comprises washing the biological sample between step (b) and step (c).

In another aspect, described herein is a method for identifying a methylation status of DNA in a biological sample, the method comprising: (a) providing one or more transposomes to the biological sample, wherein the transposomes comprise methylated adaptors, under conditions wherein the one or more methylated adaptors is inserted into the DNA, thereby generating tagmented DNA fragments comprising methylated adaptors; (b) contacting the tagmented DNA fragments with an array comprising a plurality of capture probes, wherein a capture probe in the plurality of capture probes comprises a spatial barcode, wherein if the capture probe comprises one or more cytosines, wherein the one or more cytosines are methylated cytosines; (c) ligating the sequence comprising the tagmented DNA fragments and the one or more methylated adaptors to the capture probe, thereby creating a ligation product; (d) deaminating the ligation product; and (e) determining (i) all or a portion of the sequence of the spatial barcode or the complement thereof, and (ii) all or a portion of the sequence of the ligation product, or a complement thereof, and using the determined sequences of (i) and (ii) to identify the methylation status of the DNA, or a portion thereof, in the biological sample.

In some embodiments, the ligating comprises adding a splint oligonucleotide comprises (i) a sequence that binds specifically to a portion of the capture probe; and (ii) a sequence that binds specifically to a portion of the ligation product. In some embodiments, the splint oligonucleotide comprises a sequence that binds specifically to a portion of the one or more methylated adaptors.

In some embodiments, the transposase enzyme is a Tn5 transposase enzyme, or a functional derivative thereof or a Tn7 transposase enzyme, or the functional derivative thereof.

In some embodiments, the one or more methylated adaptors comprises a first methylated adaptor and a second methylated adaptor.

In some embodiments, the method described herein further comprises incubating the ligation product with a terminal transferase and a plurality of deoxycytidine triphosphate (dCTP) molecules, thereby extending the ligation product at the 3' end.

In some embodiments, the method described herein further comprises amplifying the ligation product. In some embodiments, the method described herein further comprises amplifying the ligation product using a primer sequence that is complementary to a poly-cysteine sequence at the 3' end of the ligation product.

In some embodiments, the ligating comprises enzymatic ligation or chemical ligation. In some embodiments, the enzymatic ligation utilizes a ligase. In some embodiments, the ligase is one or more of a splintR ligase, a single stranded DNA ligase, or a T4 DNA ligase.

In some embodiments, the method described herein further comprises a migration step wherein the analyte migrates to the substrate. In some embodiments, the migration step is an active migration step comprising applying an electric field to the genomic DNA. In some embodiments, the migration step is a passive migration step.

In another aspect, described herein is a method of identifying the methylation status of a nucleic acid in a biological sample on a first substrate, comprising: (a) deaminating the nucleic acid; (b) hybridizing a first probe and a second probe to the nucleic acid, wherein: the first probe comprises (i) a sequence complementary to at least a first sequence of the nucleic acid and (ii) a sequence complementary to a capture domain of a capture probe on an array; and the second probe comprises a sequence complementary to at least a second sequence of the nucleic acid; (c) ligating the first probe and the second probe to generate a ligation product; (d) aligning the first substrate with the second substrate comprising the array, such that at least a portion of the biological sample is aligned with at least a portion of the array, wherein the array comprises a plurality of capture probes, wherein a capture probe of the plurality of capture probes comprises: (i) a spatial barcode and (ii) the capture domain; (e) when the biological sample is aligned with at least a portion of the array, (i) releasing the ligation product from the analyte and (ii) migrating the ligation product from the biological sample to the array; and (f) capturing the ligation product with the capture domain.

In some embodiments, the method described herein further comprises determining (i) all or a portion of the sequence of the spatial barcode or the complement thereof and (ii) all or a portion of the sequence of the ligation product, or a complement thereof.

In some embodiments, the method described herein further comprises using the determined sequences of (i) and (ii) to identify the methylation status of the nucleic acid in the biological sample.

In some embodiments, the first probe is at least 75%, at least 80%, at least 90%, at least 95%, at least 96%, at least 97%, at least 98%, at least 99%, or 100% complementary to the nucleic acid. In some embodiments, the first probe is about 15 to about 120 nucleotides in length. In some embodiments, the first sequence is about 10 to about 60 nucleotides in length.

In some embodiments, the second probe is at least 75%, at least 80%, at least 90%, at least 95%, at least 96%, at least 97%, at least 98%, at least 99%, or 100% complementary to the nucleic acid. In some embodiments, the second probe is about 15 to about 120 nucleotides in length. In some embodiments, the second sequence is about 10 to about 60 nucleotides in length.

In some embodiments, the first sequence and the second sequence are adjacent sequences.

In some embodiments, at least one deaminated nucleotide is located between the first sequence and the second sequence. In some embodiments, at least two, at least three, at least four, at least five, or more deaminated nucleotide is located between the first sequence and the second sequence.

In some embodiments, the method described herein further comprises generating an extended first probe and/or an extended second probe using a polymerase, wherein the extended first probe or the extended second probe comprises a sequence complementary to a sequence between the first sequence and the second sequence.

In some embodiments, at least one deaminated nucleotide is located in the first sequence. In some embodiments, the at least one deaminated nucleotide is located in the second sequence.

In some embodiments, the releasing comprises heating the biological sample. In some embodiments, step (e) further comprises contacting the biological sample with a reagent medium comprising a permeabilization reagent, optionally wherein the permeabilization reagent comprises a protease.

In some embodiments, the ligating the first probe and the second probe comprises ligating via a ligase the first probe and the second probe. In some embodiments, the ligating the first probe and the second probe comprises ligating via a ligase: (a) the first probe and the extended second probe; or (b) the extended first probe and the second probe. In some embodiments, the ligase is selected from a splintR ligase, a single stranded DNA ligase, or a T4 DNA ligase.

In some embodiments, the first probe and the second probe are on a contiguous nucleic acid. In some embodiments, the ligating utilizes a splint oligonucleotide. In some embodiments, the splint oligonucleotide comprises a first splint sequence that is substantially complementary to the first probe and a second splint sequence that is substantially complementary to the second probe.

In some embodiments, the capturing the ligation product comprises hybridizing the sequence complementary to a capture domain to the capture domain. In some embodiments, the capturing the ligation product comprises ligating the ligation product to the capture probe.

In some embodiments, the method described herein further comprises extending the capture probe using the ligation product as a template; thereby generating an extended capture probe.

In another aspect, described herein is a method of identifying a methylation status of a nucleic acid in a biological sample on a first substrate, the method comprising: (a) ligating a methylated adaptor to a nucleic acid, generating an adapted nucleic acid fragment; (b) deaminating the adapted nucleic acid fragment; (c) aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain; (d) when the biological sample is aligned with at least a portion of the array, migrating the adapted nucleic acid fragment from the biological sample to the array; and (e) capturing the adapted nucleic acid fragment with the capture domain.

In some embodiments, the method described herein further comprises determining (i) all or a portion of the sequence of the spatial barcode or the complement thereof, and (ii) all or a portion of the sequence of the ligation product, or a complement thereof.

In some embodiments, the method described herein further comprises using the determined sequences of (i) and (ii) to identify the methylation status of the nucleic acid, or a portion thereof, in the biological sample.

In some embodiments, the methylated adaptor is ligated to the nucleic acid by tagmentation. In some embodiments, the methylated adaptor is ligated to the nucleic acid at a 5' end of the nucleic acid. In some embodiments, the methylated adaptor is ligated to the nucleic acid at a 3' end of the nucleic acid.

In some embodiments, the methylated adaptor is at least about 10 nucleotides to about 50 nucleotides long.

In some embodiments, the methylated adaptor comprises at least one, at least two, at least three, at least four, at least five, or more methylated cytosines.

In some embodiments, the spatial barcode comprises at least one, at least two, at least three, at least four, at least five, or more methylated cytosines.

In some embodiments, the ligating the methylated adaptor to the nucleic acid comprises attaching the one or more methylated adaptors to the 5' and/or 3' end of the nucleic acid using a transposase enzyme complexed with a transposon, wherein the transposase enzyme is a Tn5 transposase enzyme, or the functional derivative thereof. In some embodiments, the capturing the adapted nucleic acid fragment comprises hybridizing the adapted nucleic acid fragment with the capture domain. In some embodiments, the capturing the adapted nucleic acid fragment comprises ligating the adapted nucleic acid fragment with the capture domain, wherein the ligating comprises enzymatic ligation or chemical ligation.

In some embodiments, the ligating utilizes a splint oligonucleotide, optionally wherein the splint oligonucleotide comprises a first splint sequence that is substantially complementary to the adapted nucleic acid fragment and a second splint sequence that is substantially complementary to the capture probe.

In some embodiments, the method described herein further comprises extending the capture probe using the adapted nucleic acid fragment as a template; thereby generating an extended capture probe.

In some embodiments, the method described herein further comprises incubating the adapted nucleic acid fragment with a terminal transferase and a plurality of deoxycytidine triphosphate (dCTP) molecules, thereby generating an extended adapted nucleic acid fragment.

In some embodiments, the method described herein further comprises amplifying the extended adapted nucleic acid fragment. In some embodiments, the method described herein further comprises amplifying the extended adapted nucleic acid fragment using a primer sequence that is complementary to a poly-cysteine sequence at the 3' end of the adapted nucleic acid fragment.

In some embodiments, the biological sample is a cancer tissue sample. In some embodiments, the biological sample is from a subject treated with a cancer therapy. In some embodiments, the nucleic acid is DNA. In some embodiments, the DNA is genomic DNA.

In some embodiments, the biological sample is a tissue sample, optionally wherein the tissue sample is a solid tissue sample, optionally wherein the tissue sample is a tissue section. In some embodiments, the biological sample is a fixed sample, a frozen sample, a fresh sample, or a fresh frozen sample. In some embodiments, the biological sample is a formalin fixed paraffin embedded (FFPE) sample.

In some embodiments, the first substrate is a slide. In some embodiments, the first substrate is a glass slide. In some embodiments, the first substrate does not comprise an array of capture probes.

In some embodiments, the deaminating comprises contacting the biological sample with a composition comprising sodium bisulfite. In some embodiments, the deaminating comprises treating the biological sample with an enzyme. In some embodiments, the enzyme is a cytidine deaminase or a demethylase.

In some embodiments, the second substrate is a glass slide. In some embodiments, a 5' end of the capture probe is attached to the second substrate.

In some embodiments, the array is a bead array. In some embodiments, a 5' end of the capture probe is attached to a bead of the bead array.

In some embodiments, the capture probe further comprises a unique molecular identifier (UMI).

In some embodiments, the capture probe further comprises one or more functional domains, a unique molecular identifier, a cleavage domain, and combinations thereof.

In some embodiments, the migrating is active. In some embodiments, the migrating is passive.

In some embodiments, the capture probe is extended using a polymerase.

In some embodiments, the determining comprises sequencing (i) all or a part of the sequence of the nucleic acid, or a complement thereof, and (ii) all or a part of the sequence of the spatial barcode, or a complement thereof.

In some embodiments, the methylation status comprises identifying that about 1% to about 100% of cytosines comprises a methyl group.

In some embodiments, the method described herein further comprises imaging the biological sample. In some embodiments, the imaging occurs prior to deaminating the biological sample.

In another aspect, described herein is a kit comprising parts and instruction for performing any one of the methods described herein.

In some embodiments, the kit comprises a substrate comprising a plurality of capture probes, wherein a capture probe of the plurality of first capture probes comprises (i) a spatial barcode and (ii) a capture domain.

In some embodiments, the kit comprises one or more enzyme. In some embodiments, the one or more enzyme is selected from the group consisting of a transposase, a ligase, a polymerase; a reverse transcriptase, a cytidine deaminase and a demethylase.

In some embodiments, the kit further comprises a transposome complex comprising a transposase, a transposon sequence, and/or an adaptor sequence.

In another aspect, described herein is a composition comprising reagents for performing any one of the methods described herein.

In some embodiments, the composition comprises a substrate comprising a plurality of capture probes, wherein a capture probe of the plurality of first capture probes comprises (i) a spatial barcode and (ii) a capture domain.

In some embodiments, the composition comprises one or more enzyme. In some embodiments, the one or more enzyme is selected from the group consisting of a transposase, a ligase, a polymerase; a reverse transcriptase, a cytidine deaminase and a demethylase.

In some embodiments, the composition further comprises a transposome complex comprising a transposase, a transposon sequence, and/or an adaptor sequence.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 8A shows a schematic of an example analytical workflow in which electrophoretic migration of analytes is performed after permeabilization.

FIG. 8B shows a schematic of an example analytical workflow in which electrophoretic migration of analytes and permeabilization are performed simultaneously.

FIG. 9A shows an example perpendicular, single slide configuration for use during electrophoresis.

FIG. 9B shows an example parallel, single slide configuration for use during electrophoresis.

FIG. 9C shows an example multi-slide configuration for use during electrophoresis.

DETAILED DESCRIPTION

Figure 1:
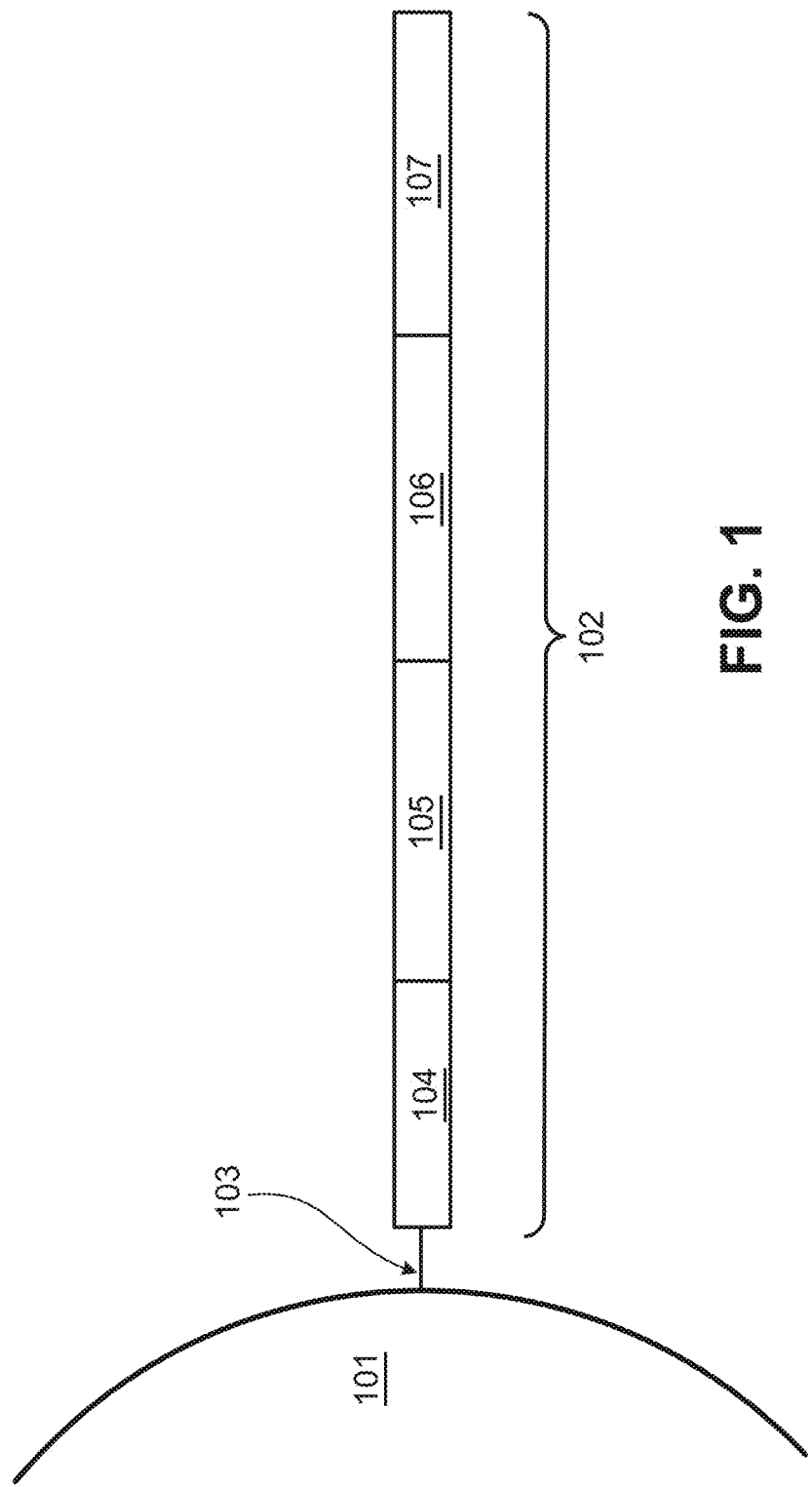
FIG. 1 is a schematic diagram showing an example of a barcoded capture probe, as described herein.

The Applicant has identified a need in the scientific community to determine, spatially, the methylation status of a biological sample. In particular, due to heterogenous cell distribution in a biological sample, it is possible that the distribution of methylated nucleotides (e.g., methylated DNA) among cells in a biological sample can vary. Methylation of DNA is an important epigenetic modification. The methylation status of each DNA molecule is variable and DNA methylation status in different cells is variable. This makes the analysis of DNA methylation challenging and cumbersome. This is further confounded by the fact that methylated-cytosine bases are not distinguishable from unmethylated-cytosine bases in standard DNA sequencing technologies (e.g., sequencing-by synthesis or Sanger sequencing).

DNA methylation is a biological process by which methyl groups are added to the DNA molecule, thereby changing gene activity without changing the underlying DNA sequence. In mammals, epigenetic modifications such as DNA methylation occur at primarily cytosine/guanine (CG) dinucleotides. DNA methylation is typically found in promoter regions (known as CpG islands) and are associated with transcriptional repression. For example, a gene can be activated (e.g., "turned on") in the presence of open chromatin and acetylated histones. In this instance, nucleotides generally remain unmethylated. However, in the presence of a methylated nucleotide (e.g., a methylated cytosine), a chromosome can be condensed, resulting in de-activation of gene expression (e.g., expression is "turned off"). Thus, when located in a gene promoter, DNA methylation typically acts to repress gene transcription. Two DNA bases, cytosine and adenine, can be methylated. Cytosine methylation is widespread in both eukaryotes and prokaryotes. Methylation of cytosine to form 5-methylcytosine occurs at the same 5' position on the pyrimidine ring where the DNA base thymine's methyl group is located; the same position distinguishes thymine from the analogous RNA base uracil, which has no methyl group. Spontaneous deamination of 5-methylcytosine converts it to thymine. This results in a T:G mismatch that can be identified through sequencing techniques.

In recent decades, DNA methylation has been a subject of intense study, including how it occurs and where it occurs, and it has been discovered that methylation is an important component in numerous cellular processes, including embryonic development, genomic imprinting, X-chromosome inactivation, and preservation of chromosome stability. DNA methylation is used as a differentiating marker in various settings, including cancer, neurology, some genetic diseases, development, cellular differentiation, model organism understanding, and during therapy (e.g., drug treatment).

Given the many processes in which methylation plays a part, errors in methylation are also linked to a variety of devastating consequences, including several human diseases.

To study DNA methylation, many researchers rely on the use of a deaminating reagent, bisulfite: a chemical can be used in a process which converts unmethylated cytosines to thymines and leaves methylated cytosines intact. However, the bisulfite is used under harsh conditions that fragment DNA, and are often not compatible with enzymes and reagents required for various applications. Herein are cost-effective and efficient techniques for determining a methylation status of a biological sample. The methods and compositions disclosed herein combine spatial analysis, multiple substrates, and methylation identification techniques.

Methods and Compositions for Spatial Analysis

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. The capture domain can have a sequence complementary to a sequence of a nucleic acid analyte. The capture domain can have a sequence complementary to a ligation product described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence complementary to a sequence of a nucleic acid analyte, a portion of a ligation product described herein, a capture handle sequence described herein, and/or a methylated adaptor described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
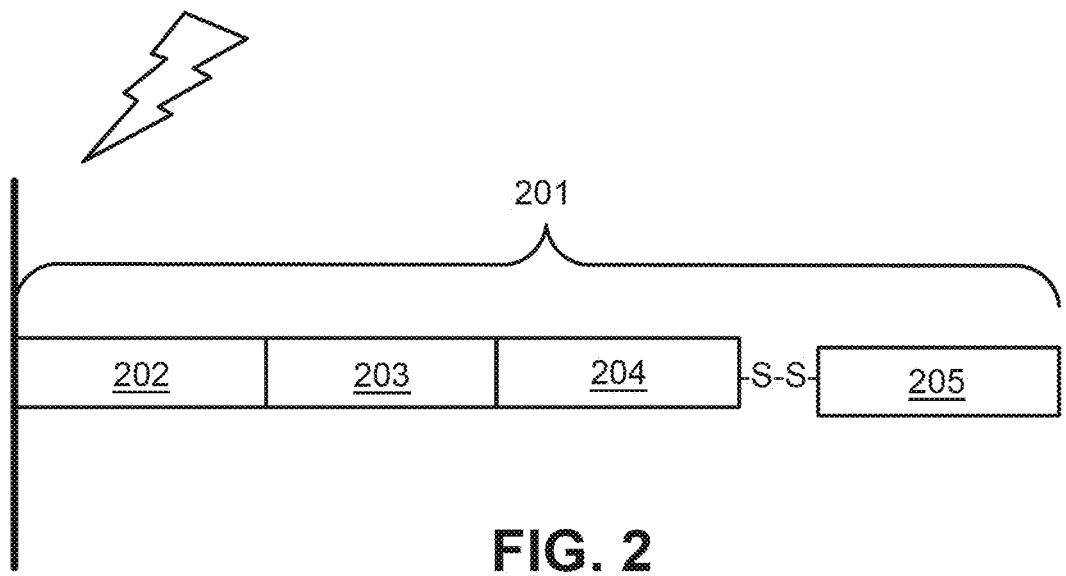
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain. Cleavable capture probe are further described in WO 2020/176788 and/or U.S. Patent Application Publication No. 2020/0277663, each of which is incorporated by reference in its entirety.

For multiple capture probes that are attached to a common array feature, the one or more spatial barcode sequences of the multiple capture probes can include sequences that are the same for all capture probes coupled to the feature, and/or sequences that are different across all capture probes coupled to the feature.

Figure 3:
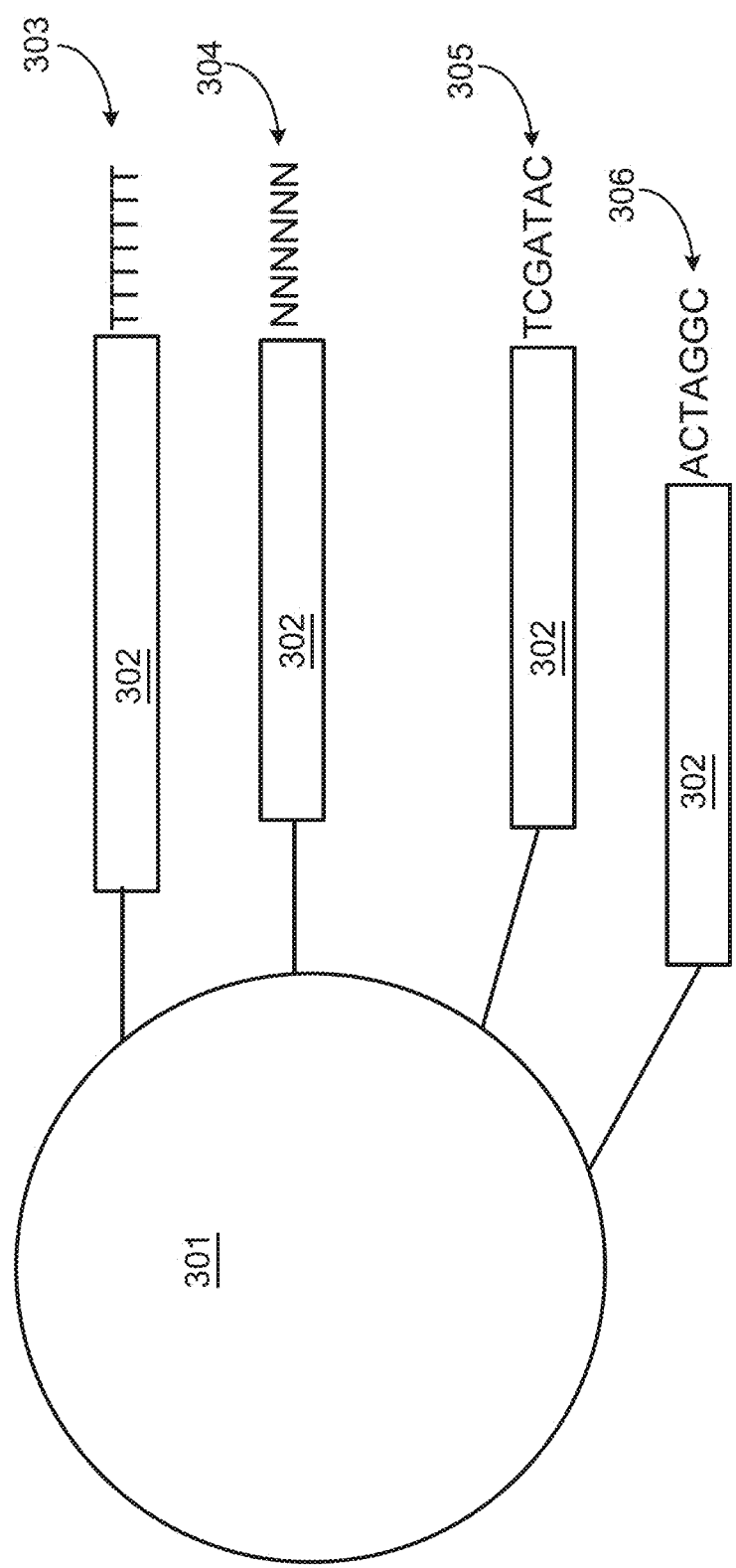
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence or capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

In some cases, capture probes may be configured to prime, replicate, and consequently yield optionally barcoded extension products from a template (e.g., a DNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/ 0277663.

Figure 4:
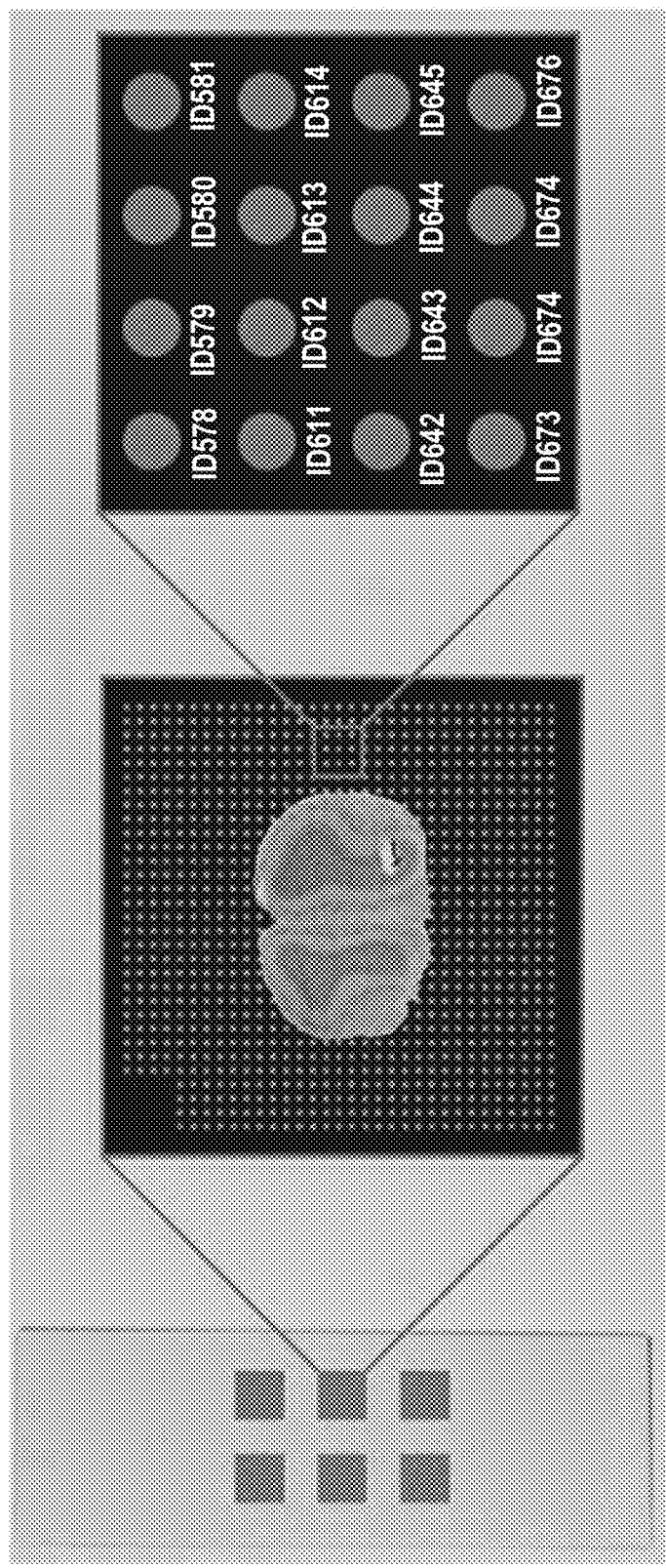
FIG. 4 is a schematic showing the arrangement of barcoded features within an array.

FIG. 4 depicts an exemplary arrangement of barcoded features within an array. From left to right, FIG. 4 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

Figure 5:
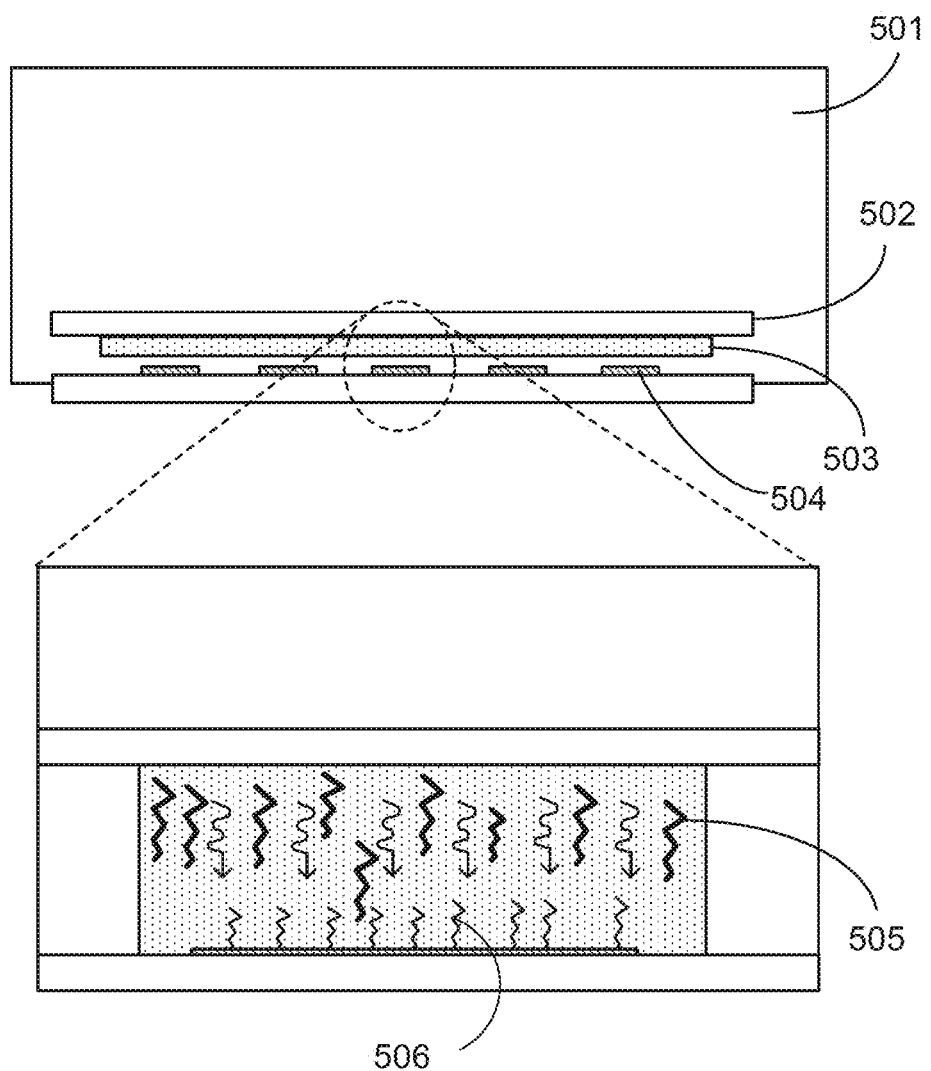
FIG. 5 is a schematic illustrating a side view of a diffusion-resistant medium, e.g., a lid.
Figure 6A:
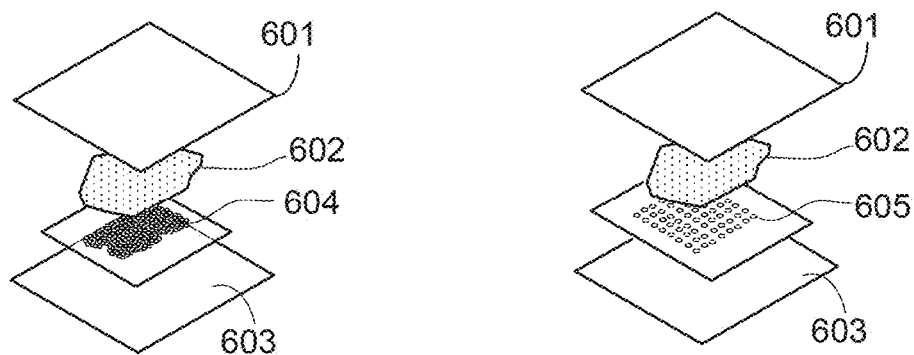
FIGS. 6A and 6B are schematics illustrating expanded FIG. 6A and side views FIG. 6B of an electrophoretic transfer system configured to direct transcript analytes toward a spatially-barcoded capture probe array.
Figure 6B:
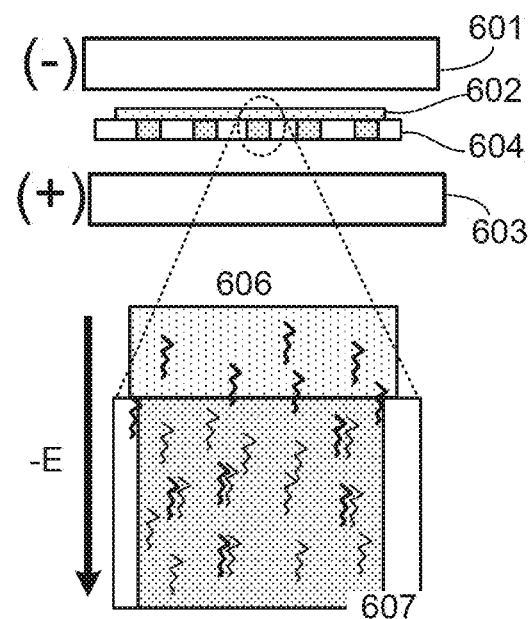
Figure 7:
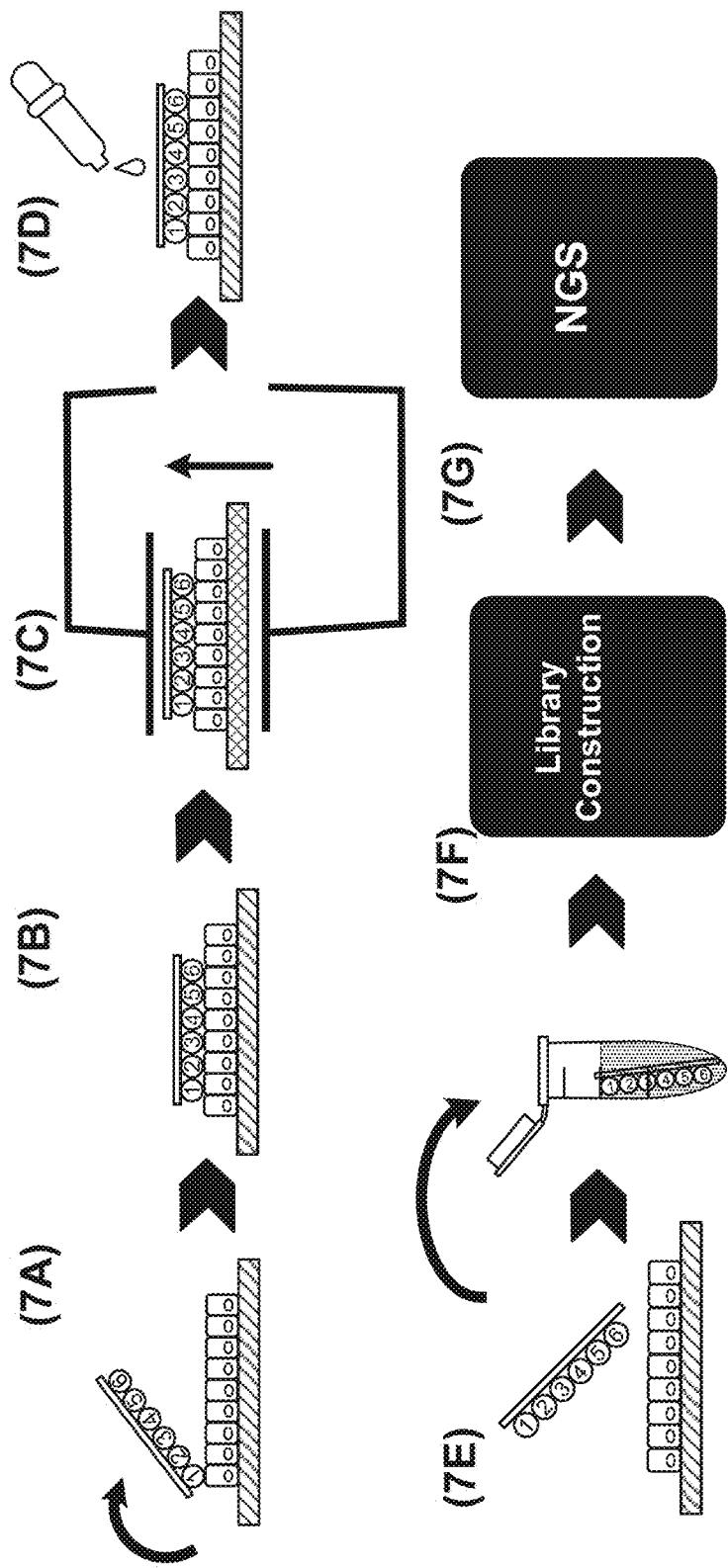
FIG. 7 is a schematic illustrating an exemplary workflow protocol utilizing an electrophoretic transfer system.

FIG. 5 is an illustration of an exemplary use of a diffusion-resistant medium. A diffusion-resistant medium/lid 502 can be contacted with a sample 503. In FIG. 5, a glass slide 504 is populated with spatially-barcoded capture probes 506, and the sample 503, 505 is contacted with the array 504, 506. A diffusion-resistant medium/lid 502 can be applied to the sample 503, wherein the sample 503 is disposed between a diffusion-resistant medium 502 and a capture probe coated slide 504. When a permeabilization solution 501 is applied to the sample, the diffusion-resistant medium/lid 502 directs the migration of the analytes 505 toward proximal capture probes 506 by reducing diffusion of the analytes out into the medium. Alternatively, the diffusion resistant medium/lid may contain permeabilization reagents.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., Nucleic Acids Res. 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distance.

Determination of Methylation Status in a Nucleic Acid

Disclosed herein are methods and compositions for determining the methylation status of a biological sample. Methylation status can be determined using methods known in the art (e.g., deamination of a nucleic acid). The methods disclosed herein combine methylation status with spatial analysis to determine the location of a methylated nucleic acid (e.g., a DNA molecule) at a spatial location in a sample. Furthermore, the methods disclosed herein allow spatial profiling of methylation status of a biological sample placed on a standard histological substrate, e.g., a standard slide.

In exemplary methods disclosed herein, a biological sample is provided on a first substrate, which can be any slide (e.g., a glass slide), and a deamination step can be performed in situ on the glass slide. Probes (e.g., a first probe, a second probe, or a methylated adaptor) interact with a nucleic acid of the biological sample. The biological sample is permeabilized and a probe-containing nucleic acid migrates to a second substrate, which includes an array having a plurality of capture probes. The sequence and location of the probe-containing nucleic acid can be determined, and based on the sequence, the methylation status at a particular location can be determined.

Methods for Identifying Methylation Status of an Analyte in a Biological Sample

Provided herein are methods for identifying a methylation status of an analyte in a biological sample. "Methylation status" as used herein refers to identifying the presence or absence of one or more methyl groups in an analyte. In some instances, the one or more methyl groups is on one or more cytosines. In some instances, the disclosure features a method for identifying a methylation status of an analyte in a biological sample, the method comprising: (a) contacting the biological sample with an array comprising a plurality of capture probes, wherein a capture probe in the plurality of capture probes comprises (i) a spatial barcode and (ii) a capture domain comprising at least one methylated cytosine; (b) deaminating the analyte; (c) contacting the analyte with a plurality of probes comprising a first probe and a second probe, wherein the first probe comprises (i) a sequence complementary to at least a first sequence of the analyte and (ii) a sequence complementary to the capture domain; and the second probe comprises a sequence complementary to at least a second sequence of the analyte; (d) ligating the first probe and the second probe, thereby generating a ligation product; (e) hybridizing the ligation product to the capture probe; (f) extending the capture probe using the ligation product as a template; thereby generating an extended capture probe; (g) amplifying the extended capture probe to produce a plurality of nucleic acids; and (h) determining (i) all or a portion of the sequence of the spatial barcode or the complement thereof, and (ii) all or a portion of the sequence of the analyte, or a complement thereof, and using the determined sequences of (i) and (ii) to identify the methylation status of the analyte in the biological sample.

In another feature, disclosed herein is a method comprising: (a) contacting the biological sample with an array, wherein the array comprises a plurality of capture probes, wherein a capture probe in the plurality of capture probes comprises (i) a spatial barcode and (ii) a capture domain; (b) deaminating the analyte; (c) contacting the analyte with a plurality of probes, wherein a probe in the plurality of probes comprises (i) a binding moiety that binds specifically to at least a portion of the analyte and (ii) an overhang sequence; (d) extending the probe using the analyte as a template, thereby generating an extended probe; (e) hybridizing the extended probe to the capture probe; (f) extending the capture probe using the extended probe as a template, thereby generating an extended capture probe; (g) amplifying the extended capture probe to produce a plurality of nucleic acids; and (h) determining (i) all or a portion of the sequence of the spatial barcode or the complement thereof, and (ii) all or a portion of the sequence of the analyte, or a complement thereof, and using the determined sequences of (i) and (ii) to identify the methylation status of the analyte in the biological sample.

Also provided herein are methods for identifying a methylation status of an analyte in a biological sample, the method comprising: (a) contacting the biological sample with an array, wherein the array comprises a plurality of capture probes, wherein a capture probe in the plurality of capture probes comprises (i) a spatial barcode and (ii) a capture domain; wherein the capture domain comprises at least one methylated cytosine; (b) deaminating the analyte; (c) contacting the analyte with a plurality of probes comprising a first probe and a second probe, wherein the first probe comprises (i) a first binding moiety that binds specifically to at least a portion of the analyte and (ii) a first overhang sequence; and the second probe comprises (i) a second binding moiety that binds specifically to at least a portion of the analyte that is adjacent to the portion of the analyte that is bound to the first binding moiety and (ii) a second overhang sequence; and (d) extending the first probe using the analyte as a template; (e) ligating the first probe and the second probe, thereby generating an extended probe; (f) hybridizing the extended probe to the capture probe; (g) extending the capture probe using the extended probe as a template; thereby generating an extended capture probe; (h) amplifying the extended capture probe to produce a plurality of nucleic acids; and (i) determining (i) all or a portion of the sequence of the spatial barcode or the complement thereof, and (ii) all or a portion of the sequence of the analyte, or a complement thereof, and using the determined sequences of (i) and (ii) to identify the methylation status of the analyte in the biological sample. In some embodiments, ligating comprises enzymatic ligation or chemical ligation. In some embodiments, the enzymatic ligation utilizes a ligase.

Also provided herein are methods for identifying a methylation status of an analyte, e.g., a nucleic acid, in a biological sample. "Methylation status" as used herein refers to identifying the presence or absence of one or more methyl groups in an analyte (e.g., on a cytosine). In some instances, methylation status can be an absolute number of methylated cytosines or non-methylated cytosines in a nucleic acid. In some instances, methylation status can be a percentage of cytosines that are either methylated or non-methylated in a nucleic acid.

In some instances, the disclosure features a method for identifying a methylation status of a nucleic acid in a biological sample. In some instances, the biological sample is placed on a substrate that does not include capture probes. In this way, all steps of deamination are carried out on this substrate. The methods provided herein allows the deamination steps to be separated from the spatial analysis of the analyte, e.g., nucleic acid. In an exemplary embodiment, the biological sample is placed on a regular slide, e.g., a glass slide that does not have capture probes. Because the deamination is separated from the capturing of molecules on the spatial array, the capture probes of the spatial array is not affected by the deamination reagents.

In some exemplary methods, provided herein are methods of identifying the methylation status of a nucleic acid in a biological sample on a first substrate. In some instances, the methods include (a) deaminating the nucleic acid; (b) hybridizing a first probe and a second probe to the nucleic acid, wherein: the first probe comprises (i) a sequence complementary to at least a first sequence of the nucleic acid and (ii) a sequence complementary to a capture domain of a capture probe on an array; and the second probe comprises a sequence complementary to at least a second sequence of the nucleic acid; (c) ligating the first probe and the second probe to generate a ligation product; (d) aligning the first substrate with the second substrate comprising the array, such that at least a portion of the biological sample is aligned with at least a portion of the array, wherein the array comprises a plurality of capture probes, wherein a capture probe of the plurality of capture probes comprises: (i) a spatial barcode and (ii) the capture domain; (e) when the biological sample is aligned with at least a portion of the array, (i) releasing the ligation product from the analyte and (ii) migrating the ligation product from the biological sample to the array; and (f) capturing the ligation product with the capture domain.

In other exemplary methods, provided herein are methods of identifying a methylation status of a nucleic acid in a biological sample on a first substrate. In some instances, the methods include (a) ligating a methylated adaptor to a nucleic acid, generating an adapted (e.g., tagmented) nucleic acid fragment; (b) deaminating the adapted (e.g., tagmented) nucleic acid fragment; (c) aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain; (d) when the biological sample is aligned with at least a portion of the array, migrating the adapted (e.g., tagmented) nucleic acid fragment from the biological sample to the array; and (e) capturing the adapted (e.g., tagmented) nucleic acid fragment with the capture domain.

Preparation of the Biological Sample

Biological Samples and Analytes

The biological sample as used herein can be any suitable biological sample described herein or known in the art. In some embodiments, the biological sample is a tissue. In some embodiments, the biological sample is a tissue section. In some embodiments, the tissue is flash-frozen and sectioned. Any suitable methods described herein or known in the art can be used to flash-freeze and section the tissue sample. In some embodiments, the biological sample, e.g., the tissue, is flash-frozen using liquid nitrogen before sectioning. In some embodiments, the sectioning is performed using cryosectioning. In some embodiments, the methods further comprises a thawing step, after the cryosectioning. In some embodiments, the biological sample, e.g., the tissue sample is fixed, for example in methanol, acetone, PFA or is formalin-fixed and paraffin-embedded (FFPE).

The biological sample, e.g., tissue sample, can be stained, and imaged prior, during, and/or after each step of the methods described herein. Any of the methods described herein or known in the art can be used to stain and/or image the biological sample. In some embodiments, the imaging occurs prior to deaminating the sample. In some embodiments, the biological sample is stained using an H&E staining method. In some embodiments, the tissue sample is stained and imaged for about 10 minutes to about 2 hours (or any of the subranges of this range described herein). Additional time may be needed for staining and imaging of different types of biological samples.

The tissue sample can be obtained from any suitable location in a tissue or organ of a subject, e.g., a human subject. In some embodiments, the tissue sample is obtained from a location where the DNA is differentially methylated compared to a reference location. The location where the DNA is differentially methylated can be, for example, a diseased cell, tissue or organ, an infected cell, tissue or organ, a damaged cell, tissue or organ, a cancerous cell, tissue or organ (e.g., a tumor cell, tissue, or organ), or a differentiating cell, tissue, or organ (e.g., a stem cell or a tissue or organ that comprises one or more stem cells). In some embodiments, the location wherein the DNA is differentially methylated is a cell, tissue, or organ that has been administered one or more drug(s), e.g., therapeutic drugs. Other locations that include differentially methylated DNA are known in the art.

In some embodiments, the biological sample is a tumor cell, tissue, or organ. Non-limiting examples of cancers referred to in any one the methods described herein include: sarcomas, carcinomas, adrenocortical carcinoma, AIDS-related cancers, anal cancer, appendix cancer, astrocytomas, atypical teratoid/rhabdoid tumor, basal cell carcinoma, bladder cancer, brain stem glioma, brain tumors (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors, and pineoblastoma), breast cancer, bronchial tumors, cancer of unknown primary site, carcinoid tumor, carcinoma of unknown primary site, central nervous system atypical teratoid/rhabdoid tumor, central nervous system embryonal tumors, cervical cancer, childhood cancers, chordoma, colon cancer, colorectal cancer, craniopharyngioma, endocrine pancreas islet cell tumors, endometrial cancer, ependymoblastoma, ependymoma, esophageal cancer, esthesioneuroblastoma, Ewing sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal cell tumor, gastrointestinal stromal tumor (GIST), gestational trophoblastic tumor, glioma, head and neck cancer, heart cancer, hypopharyngeal cancer, intraocular melanoma, islet cell tumors, Kaposi's sarcoma, kidney cancer, Langerhans cell histiocytosis, laryngeal cancer, lip cancer, liver cancer, lung cancer, malignant fibrous histiocytoma bone cancer, medulloblastoma, medulloepithelioma, melanoma, Merkel cell carcinoma, Merkel cell skin carcinoma, mesothelioma, metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, non-melanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pineal parenchymal tumors of intermediate differentiation, pineoblastoma, pituitary tumor, pleuropulmonary blastoma, primary hepatocellular liver cancer, prostate cancer, rectal cancer, renal cancer, renal cell (kidney) cancer, renal cell cancer, respiratory tract cancer, retinoblastoma, rhabdomyosarcoma, salivary gland cancer, Sezary syndrome, small cell lung cancer, small intestine cancer, soft tissue sarcoma, squamous cell carcinoma, squamous neck cancer, stomach (gastric) cancer, supratentorial primitive neuroectodermal tumors, testicular cancer, throat cancer, thymic carcinoma, thymoma, thyroid cancer, transitional cell cancer, transitional cell cancer of the renal pelvis and ureter, trophoblastic tumor, ureter cancer, urethral cancer, uterine cancer, uterine sarcoma, vaginal cancer, vulvar cancer, Waldenström macroglobulinemia, and Wilm's tumor.

In some embodiments, the biological sample is a cancer sample. In some embodiments, the cancer can be treated using an epigenetic therapy (e.g., a hypomethylating agent).

In some embodiments, the cancer is a non-small-cell lung cancer (NSCLC), a microsatellite-stable colorectal cancer (CRC), a head and neck cancer, a head and neck squamous cell carcinoma (HNSCC), a melanoma, an acute myeloid leukemia (AML), a myelodysplastic syndromes (MDS), a pancreatic ductal adenocarcinoma (PDAC), an ovarian cancer, a primary peritoneal or fallopian tube cancer, a peripheral T-Cell lymphoma (PTCL), an ovarian cancer type II or oestrogen receptor-positive and HER2-negative breast cancer, a diffuse large B-cell lymphoma (DLBCL), a central nervous system (CNS) solid tumor, a lung cancer, a renal cancer, a hepatocellular carcinoma, a pancreatic adenocarcinoma, a cholangiocarcinoma, or a chronic myelomonocytic leukemia (CMML).

Methylation of key markers are used for cancer diagnosis. These key markers are described, e.g., in Locke W J et al., DNA Methylation Cancer Biomarkers: Translation to the Clinic. *Front. Genet.* 10:1150, 2019; Nassiri, F. et al., Detection and discrimination of intracranial tumors using plasma cell-free DNA methylomes. *Nat Med* 26, 1044-1047, 2020; and Nuzzo, P. V. et al., Detection of renal cell carcinoma using plasma and urine cell-free DNA methylomes. *Nat Med* 26, 1041-1043 (2020), the entire contents of which are incorporated herein by reference.

Suitable agents such as hypomethylating agents can be used as epigenetic therapies for the treatment of cancer. 5-Azacitidine (5-Aza), 5-aza-2'-deoxycytidine (decitabine) and SGI-110 (guadecitabine) are analogues of the nucleoside cytidine that irreversibly sequester DNMT proteins to DNA, leading to global DNA hypomethylation.

In some embodiments, the cancer sample is from a subject treated with a cancer therapy. In some embodiments, the cancer therapy is therapy with nucleoside cytidine analogue. In some embodiments, the cancer therapy is a therapy with 5-Azacitidine (5-Aza), 5-aza-2'-deoxycytidine (decitabine), or SGI-110 (guadecitabine).

The analyte can be any suitable analyte described herein. In some embodiments, the analyte is a nucleic acid. In some embodiments, the analyte is a DNA. In some embodiments, the analyte is a genomic DNA. In some embodiments, the analyte is a non-genomic DNA. In some embodiments, the DNA is within a coding region of a gene. In some embodiments, the DNA is within a promoter region of a gene. In some embodiments, the DNA is outside of the coding region of a gene. In some embodiments, the DNA spans a coding region and a non-coding region of a gene. In some embodiments, the DNA spans the coding region and/or the non-coding region of more than one genes.

In some embodiments, the DNA is a methylated DNA, e.g., a DNA comprising one or more methylated cytosines. In some embodiments, the DNA is an unmethylated DNA, e.g., a DNA that does not comprise any methylated cytosine. In some embodiments, the DNA is a DNA that is differentially methylated in a location compared to a reference location.

The size of the analyte, e.g., DNA, can be any suitable size of a nucleic acid molecule in a biological sample. In some embodiments, the size of the target nucleic acid is about 50 nucleotides to about 100,000 nucleotides (e.g., about 50 nucleotides to about 200 nucleotides, about 200 nucleotides to about 500 nucleotides, about 500 nucleotides to about 1,000 nucleotides, about 1,000 nucleotides to about 2,000 nucleotides, about 2,000 nucleotides to about 4,000 nucleotides, about 4,000 nucleotides to about 6,000 nucleotides, about 6,000 nucleotides to about 8,000 nucleotides, about 8,000 nucleotides to about 10,000 nucleotides, about 10,000 nucleotides to about 20,000 nucleotides, about 20,000 nucleotides to about 30,000 nucleotides, about 30,000 nucleotides to about 40,000 nucleotides, about 40,000 nucleotides to about 50,000 nucleotides, about 50,000 nucleotides to about 60,000 nucleotides, about 60,000 nucleotides to about 70,000 nucleotides, about 70,000 nucleotides to about 80,000 nucleotides, about 80,000 nucleotides to about 90,000 nucleotides, or about 90,000 nucleotides to about 100,000 nucleotides).

In some embodiments, the DNA includes at least a portion of a tumor biomarker gene. In some embodiments, the tumor biomarker is a tumor antigen. Exemplary tumor antigens include, but are not limited to, melanoma-associated antigen (MAGE) series of antigens (e.g., MAGE-C1 (cancer/testis antigen CT7), MAGE-B1 antigen (MAGE-XP antigen, DAM10), MAGE-B2 antigen (DAME), MAGE-2 antigen, MAGE-4a antigen, and MAGE-4b antigen), tyrosinase, glycoprotein 100 (gp100), disialoganglioside GD-2, disialoganglioside 0-acetylated GD-3, ganglioside GM-2, epidermal growth factor receptor (EGFR), vascular endothelial growth factor receptor (VEGFR), mutant B-Raf antigen associated with melanoma and colon cancer, human epidermal growth factor receptor-2 (HER-2/neu) antigen, melanoma-associated antigen recognized by T cells (MART-1) (e.g., MART-1 26-35 peptide or MART-1 27-35 peptide), protein kinase C-binding protein, reverse transcriptase protein, A-kinase-anchoring protein (AKAP protein), vaccinia-related kinase Serine/Threonine Kinase 1 (VRK1), fucosyltransferase (T6-7), zinc finger protein 258 (T11-6), p53-binding protein (T1-52), T5-15 (KIAA1735), T5-13 (Sosl), T11-5 (hypothetical protein MGC4170), T11-9 (hypothetical protein AF225417), T11-3 (trap ankyrin repeat), T7-1 (KIAA1288), a mutant or wild type RAS peptide, *Homo sapiens* telomerase ferment (hTRT), cytokeratin-19 (CYFRA21-1), squamous cell carcinoma antigen 1 (SCCA-1), protein T4-A, squamous cell carcinoma antigen 2 (SCCA-2), ovarian carcinoma antigen CA125 (1A1-3B) (KIAA0049), cell surface-associated MUCIN 1 (e.g., tumor-associated MUCIN, carcinoma-associated MUCIN, polymorphic epithelial MUCIN peanut-reactive urinary MUCIN, polymorphic epithelial mucin (PEM), PEMT, episialin, tumor-associated epithelial membrane antigen, epithelial membrane antigen (EMA), H23 antigen (H23AG), PUM, and breast carcinoma-associated antigen DF3), CTCL tumor antigen sel-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, prostate-specific membrane antigen, 5T4 oncofetal trophoblast glycoprotein, Orf73 Kaposi's sarcoma-associated herpesvirus, colon cancer antigen NY-CO-45, lung cancer antigen NY-LU-12 variant A, cancer associated surface antigen, adenocarcinoma antigen ART1, paraneoplastic associated brain-testis-cancer antigen (onconeuronal antigen MA2; paraneoplastic neuronal antigen), neuro-oncological ventral antigen 2 (NOVA2), hepatocellular carcinoma antigen gene 520, tumor-associated antigen CO-029, tumor-associated antigen MAGE-X2, synovial sarcoma antigen, X breakpoint 2, squamous cell carcinoma antigen recognized by T cell, serologically defined colon cancer antigen 1, serologically defined breast cancer antigen NY-BR-15, serologically defined breast cancer antigen NY-BR-16, chromogranin A, parathyroid secretory protein 1, pancreatic cancer-associated antigen (DUPAN-2), carbohydrate antigen CA 19-9, carbohydrate antigen CA 72-4, carbohydrate antigen CA 195, and carcinoembryonic antigen (CEA).

In some embodiments, the tumor antigen is BRCA1, CDKN2A (p16$^{INK4}$a), CDKN2B (p15$^{INK4b}$) GSTP1, MGMT, RASSF1A, or SFRP2.

Exemplary First and Second Substrates

In some instances, the biological sample is placed (e.g., mounted or otherwise immobilized) on a first substrate. The first substrate can be any solid or semi-solid support upon which a biological sample can be mounted. In some instances, the first substrate is a slide. In some instances, the slide is a glass slide. In some embodiments, the substrate is made of glass, silicon, paper, hydrogel, polymer monoliths, or other material known in the art. In some embodiments, the first substrate is comprised of an inert material or matrix (e.g., glass slides) that has been functionalized by, for example, treating the substrate with a material comprising reactive groups which facilitate mounting of the biological sample.

In some embodiments, the first substrate does not comprise a plurality (e.g., array) of capture probes, each comprising a spatial barcode.

A substrate, e.g., a first substrate and/or a second substrate, can generally have any suitable form or format. For example, a substrate can be flat, curved, e.g., convexly or concavely curved. For example, a first substrate can be curved towards the area where the interaction between a biological sample, e.g., tissue sample, and a first substrate takes place. In some embodiments, a substrate is flat, e.g., planar, chip, or slide. A substrate can contain one or more patterned surfaces within the first substrate (e.g., channels, wells, projections, ridges, divots, etc.).

A substrate, e.g., a first substrate and/or second substrate, can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments wherein a substrate structure is flat, the substrate structure can be any appropriate type of support having a flat surface (e.g., a chip or a slide such as a microscope slide).

First and/or second substrates can optionally include various structures such as, but not limited to, projections, ridges, and channels. A substrate can be micropatterned to limit lateral diffusion of analytes (e.g., to improve resolution of the spatial analysis). A substrate modified with such structures can be modified to allow association of analytes, features (e.g., beads), or probes at individual sites. For example, the sites where a substrate is modified with various structures can be contiguous or non-contiguous with other sites.

In some embodiments, the surface of a first and/or second substrate is modified to contain one or more wells, using techniques such as (but not limited to) stamping, microetching, or molding techniques. In some embodiments in which a first and/or second substrate includes one or more wells, the first substrate can be a concavity slide or cavity slide. For example, wells can be formed by one or more shallow depressions on the surface of the first and/or second substrate. In some embodiments, where a first and/or second substrate includes one or more wells, the wells can be formed by attaching a cassette (e.g., a cassette containing one or more chambers) to a surface of the first substrate structure.

In some embodiments where the first and/or second substrate is modified to contain one or more structures, including but not limited to, wells, projections, ridges, features, or markings, the structures can include physically altered sites. For example, a first and/or second substrate modified with various structures can include physical properties, including, but not limited to, physical configurations, magnetic or compressive forces, chemically functionalized sites, chemically altered sites, and/or electrostatically altered sites. In some embodiments where the first substrate is modified to contain various structures, including but not limited to wells, projections, ridges, features, or markings, the structures are applied in a pattern. Alternatively, the structures can be randomly distributed.

In some embodiments, a first substrate includes one or more markings on its surface, e.g., to provide guidance for aligning at least a portion of the biological sample with a plurality of capture probes on the second substrate during a sandwich type process disclosed herein. For example, the first substrate can include a sample area indicator identifying the sample area. In some embodiments, the sample area indicator on the first substrate is aligned with an area of the second substrate comprising a plurality of capture probes. In some embodiments, the first and/or second substrate can include a fiducial mark. In some embodiments, the first and/or second substrate does not comprise a fiducial mark. In some embodiments, the first substrate does not comprise a fiducial mark and the second substrate comprises a fiducial mark. Such markings can be made using techniques including, but not limited to, printing, sand-blasting, and depositing on the surface.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., Applied Optics 46:421-427, 2007), the entire contents of which are incorporated herein by reference. In some embodiments, a fiducial marker can be a physical particle (e.g., a nanoparticle, a microsphere, a nanosphere, a bead, a post, or any of the other exemplary physical particles described herein or known in the art).

In some embodiments, a fiducial marker can be present on a first substrate to provide orientation of the biological sample. In some embodiments, a microsphere can be coupled to a first substrate to aid in orientation of the biological sample. In some examples, a microsphere coupled to a first substrate can produce an optical signal (e.g., fluorescence). In some embodiments, a quantum dot can be coupled to the first substrate to aid in the orientation of the biological sample. In some examples, a quantum dot coupled to a first substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Although not required, it can be advantageous to use a marker that can be detected using the same conditions (e.g., imaging conditions) used to detect a labelled cDNA.

In some embodiments, a fiducial marker can be randomly placed in the field of view. For example, an oligonucleotide containing a fluorophore can be randomly printed, stamped, synthesized, or attached to a first substrate (e.g., a glass slide) at a random position on the first substrate. A tissue section can be contacted with the first substrate such that the oligonucleotide containing the fluorophore contacts, or is in proximity to, a cell from the tissue section or a component of the cell (e.g., an mRNA or DNA molecule). An image of the first substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a first substrate). In this instance, a fiducial marker can be stamped, attached, or synthesized on the first substrate and contacted with a biological sample. Typically, an image of the sample and the fiducial marker is taken, and the position of the fiducial marker on the first substrate can be confirmed by viewing the image.

In some embodiments, a fiducial marker can be an immobilized molecule (e.g., a physical particle) attached to the first substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold).

A wide variety of different first substrates can be used for the foregoing purposes. In general, a first substrate can be any suitable support material. Exemplary first substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene polycarbonate, or combinations thereof.

Among the examples of first substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In another example, a first substrate can be a flow cell. Flow cells can be formed of any of the foregoing materials, and can include channels that permit reagents, solvents, features, and analytes to pass through the flow cell. In some embodiments, a hydrogel embedded biological sample is assembled in a flow cell (e.g., the flow cell is utilized to introduce the hydrogel to the biological sample). In some embodiments, a hydrogel embedded biological sample is not assembled in a flow cell. In some embodiments, the hydrogel embedded biological sample can then be prepared and/or isometrically expanded as described herein.

Exemplary substrates similar to the first substrate (e.g., a substrate having no capture probes) and/or the second substrate are described in WO 2020/123320, which is hereby incorporated by reference in its entirety.

Staining and Imaging the Biological Sample

After placement of the biological sample onto the first substrate, biological samples can be stained using a wide variety of stains and staining techniques. In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the methods disclosed herein include imaging the biological sample. In some instances, imaging the sample occurs prior to deaminating the biological sample.

The sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some instances, the stain is an H&E stain.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or discoloring a biological sample are known in the art, and generally depend on the nature of the stain(s) applied to the sample. For example, H&E staining can be destained by washing the sample in HCl, or any other acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in an acid (e.g., HCl). In some embodiments, destaining can include adding HCl to a downstream solution (e.g., permeabilization solution). In some embodiments, destaining can include dissolving an enzyme used in the disclosed methods (e.g., pepsin) in an acid (e.g., HCl) solution. In some embodiments, after destaining hematoxylin with an acid, other reagents can be added to the destaining solution to raise the pH for use in other applications. For example, SDS can be added to an acid destaining solution in order to raise the pH as compared to the acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65(8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/µl RNAse inhibitor for 10 min at 4° C.) before being stained with fluorescent primary antibodies (1:100 in 3×SSC, 2% BSA, 0.1% Triton X, 1 U/µl RNAse inhibitor for 30 min at 4° C.). The biological sample can be washed, coverslipped (in glycerol+1 U/µl RNAse inhibitor), imaged (e.g., using a confocal microscope or other apparatus capable of fluorescent detection), washed, and processed according to analyte capture or spatial workflows described herein.

As used herein, an antigen retrieval buffer can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases unspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

Deamination of Nucleic Acids in the Biological Sample

In some embodiments, the methods described herein include deaminating the analyte. In some embodiments, either before or after deamination, the methods described herein include a step of permeabilizing the biological sample. In some instances, the permeabilization step occurs prior to deaminating the analyte in the sample. In some instances, permeabilizing includes contacting the biological sample with a permeabilization reagent. Any suitable permeabilization reagent described herein can be used. In some embodiments, the permeabilization reagent is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin.

In some embodiments, the deaminating of the analyte is achieved by contacting the analyte with one or more enzymatic or chemical deaminating agent(s). In some instances, the deaminating agent fragments the analyte (e.g., DNA). Any suitable deaminating agents can be used in the methods described herein. In some embodiments, the analyte, e.g., DNA, is denatured into a single-stranded molecule prior to the treatment of the deaminating agent(s). In some embodiments, the deaminating step includes contacting the sample with a composition comprising bisulfite. In some embodiments, the bisulfite is sodium bisulfite.

In some instances, the deaminating step is performed prior to the hybridization of one or more probes to the analytes (e.g., nucleic acid molecules) and the capture of the ligated (e.g., ligation) probes on a spatial array. For example, the biological sample is placed on a regular slide (different from a spatial array) without capture probes, and the nucleic acid molecules in the biological sample are deaminated as described herein.

In some embodiments, the deaminating comprises treating the sample enzymatically. In some embodiments, the sample is treated with a deaminase. Any suitable enzymes known in the art can be used in the methods described herein. In some embodiments, the enzyme is a eukaryotic DNA methyltransferases (CG). In some embodiments, the enzyme is a prokaryotic DNA (cytosine-5)methyltransferase. In some embodiments, the enzyme is apolipoprotein B mRNA editing enzyme, catalytic polypeptide-like (APOBEC, cytidine deaminase). In some embodiments, the enzyme is an enzyme of the ten-eleven translocation (TET) family demethylase.

In some embodiments, unmethylated cytosines, if present in the analyte in the sample, are deaminated into uracils. After the binding of the probe with the deaminated analyte, the probe is extended wherein each uracil, if present in the analyte, is base-paired with an adenine. In some embodiments, the extended probe comprises an adenine in each position corresponding to the unmethylated cytosines in the analyte in the sample. In some embodiments, all of the unmethylated cytosines in the analyte are converted to uracils by the deaminating step. In some instances, cytosines that are methylated are not converted to uracil. Instead, methylated cytosines remain as cytosines.

In some instances, prior to addition of the probes described in the next section, the sample is treated with a permeabilization agent. In some instances, the permeabilization agent is a diluted permeabilization agent. In some instances, the diluted permeabilization agent includes, but is not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroyl-sarcosine sodium salt solution). Exemplary permeabilization reagents are described in in PCT Patent Application Publication No. WO 2020/123320, which is incorporated by reference in its entirety. In some instances, dilution of the permeabilization agent is by about 10-fold, about 50-fold, about 100-fold, about 200-fold, about 300-fold, about 400-fold, about 500-fold, or higher.

In some embodiments, the method further comprises washing the biological sample. In some instances, a wash step occurs between the deamination step and the step where the probes are added. In some embodiments, the washing step is conducted to remove all or a part of the deaminating agent. In some embodiments, the washing step does not remove the analyte in the biological sample. In some embodiments, the washing step removes an insignificant amount of the analyte in the biological sample. In some instances, a wash step occurs after hybridizing the oligonucleotides. In some instances, this wash step removes any unbound oligonucleotides and can be performed using any technique or solution disclosed herein or known in the art. In some embodiments, multiple wash steps are performed to remove unbound oligonucleotides.

Addition of Probes to Biological Sample

Addition of First and Second Probes

After deamination, in some instances, one or more probes are added to the biological sample. In some instances, the one or more probes (e.g., a first probe; a second probe) is at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99. 100, at least about 105, at least about 110, at least about 115, at least about 120, at least about 125, at least about 135, at least about 140, or more nucleotides in length. In some embodiments, the probe includes sequences that are complementary or substantially complementary to an analyte, e.g., a nucleic acid. By substantially complementary, it is meant that the probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in an analyte. In some instances, the first probe and the second probe hybridize to adjacent sequences on an analyte.

In some instances, the probes hybridize to a sequence that is from 5 to 140 nucleotides in length (e.g., is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 nucleotides in length). In some instances, the probes hybridize to a sequence that is from 15 to 120 nucleotides in length.

In some instances, the probes are DNA probes. In some instances, a first probe includes at least two ribonucleic acid bases at the 3' end and a second probe includes a phosphorylated nucleotide at the 5' end.

Probes (e.g., a first probe and a second probe) can be designed using methods known in the art. In addition, probes can be designed so that (1) one or both probes hybridize directly to a potential region of methylation or (2) the probes flank a potential region of methylation.

In some instances, the probes used herein are designed to hybridize to sequences that are mutated (e.g., from cytosine to thymine) as a result of the deamination step (i.e., deaminated nucleic acid). In some instances, the probes used herein are designed to hybridize to sequences that are not mutated (e.g., cytosines that are methylated are not mutated during the deamination step) as a result of the deamination step. In some instances, the probes used herein are designed to hybridize to sequences that include at least one nucleotide that is mutated as a result of the deamination step. In some instances, the probes used herein are designed to hybridize to sequences that include more than one (e.g., 2, 3, 4, 5, or more) nucleotide that is mutated as a result of the deamination step.

In some instances, probes are designed to flank (i.e., surround) sequences that are sites of methylation investigation. In some instances, the sequence between the two regions of an analyte where the probes hybridize (i.e., the intervening sequence) include one or more nucleotides that is mutated (e.g., from cytosine to thymine) during the deamination step. In some instances, the intervening sequence includes at least 2, 3, 4, 5, 6, 7, 8, 9, 10, or more nucleotides that have been mutated during the deamination step described herein. For example, in some instances, a first probe can be designed to hybridize to a site 5' to a site of methylation investigation, and a second probe can be designed to hybridize to a site 5' to a site of methylation investigation (or vice versa). One hybridized, the sequence in between the two sites of hybridization can be determined, providing insight on whether a particular nucleotide (e.g., a cytosine) has been methylated. In some instances, the probes hybridize to sequences that are at least about 1, 2, 3, 4, 5, 6, 7, 8, 9, 10, or more nucleotides apart. In some embodiments, at least one (e.g., 1, 2, 3, 4, 5, 6, 7, 8, 9, 10 or more) deaminated nucleotide is located in the sequence between the hybridized probes.

In some instances, more than one (e.g., 2, 3, 4, 5, or more) probes hybridize to a target DNA molecule. In some instances, two probes hybridize to sequences that are adjacent to one another. In some instances, the probes are coupled. In some instances, the probes are coupled via ligation. In some instances, because the probes hybridize to adjacent sequences, ligation can occur between the adjacent probes after hybridization (i.e., no extension step as described herein is required). In some instances, two probes hybridize to sequences of an analyte that are separated by at least 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, about 150, about 175, about 200, about 250, about 300, about 350, about 400, about 450, about 500, about 600, about 700, about 800, about 900, or about 1000 nucleotides. In some instances, the probes hybridize to a sequence that has been modified (e.g. includes a mutation) after deamination. In some instances, the mutation is a cytosine to a thymine. In some instances, the analyte includes more than one mutation as a result of the deamination step. In some instances, there are 1, 2, 3, 4, 5, 6, 7, 8, 9, 10 or more cytosines that are mutated to a thymine (i.e., the cytosines are not methylated). In some instances, there are 1, 2, 3, 4, 5, 6, 7, 8, 9, 10 or more cytosines that are not mutated to a thymine (i.e., the cytosines are methylated). In some instances, the probe is designed to detect one or more deamination mutations.

The one or more probes include a sequence that specifically binds to a sequence on the target analyte. In some embodiments, the binding moiety comprises a sequence that specifically binds to a region that does not have a CG dinucleotide. In some instances, the binding moiety comprises a sequence that specifically binds to a region that includes AA, AT, AC, AG, CA, CT, CC, GA, GC, GT, GG, TA, TC, TG, or TT dinucleotides. In some embodiments, the binding of the binding moiety to the target analyte does not affect the identification of the methylation status of the target analyte.

In some instances, the one or more probes (e.g., a first probe; a second probe) further includes a sequence that can hybridize to a capture probe sequence (e.g., on an array, as described herein). In some instances, the sequence that hybridizes to the capture probe is a poly-adenylation (poly (A)) sequence. In some instances, the sequence that hybridizes to the capture probe is a degenerate (e.g., random) sequence. In some instances, the sequence that hybridizes to the capture probe is designed to be a specific sequence, for example a sequence that is complementary to a specific target sequence in a DNA or RNA molecule.

In some embodiments, at least one of the probes is extended using a polymerase. In some instances, the methods disclosed herein include generating an extended first probe. In some instances, the methods disclosed herein include generating an extended second probe. In some instances, the extended first probe or the extended second probe includes a sequence complementary to a sequence between the first sequence and the second sequence. In some instances, one of the probes is extended to fill in the gap between the two hybridized probes. In some embodiments, the capture probe is extended using a polymerase. In some embodiments, the polymerase is a DNA polymerase. In some embodiments, the DNA polymerase is a thermostable DNA polymerase including, but are not limited to, DNA polymerase such as Phusion, Hot Start Taq DNA Polymerase, and EpiMark® Hot Start Taq DNA Polymerase.

In some instances, the probes (e.g., the first probe and the second probe) are ligated together. In instances of ligation, any suitable ligase can be used in the methods described herein. In some instances, the probes may be subjected to an enzymatic ligation reaction, using a ligase (e.g., T4 RNA ligase 2, a splintR ligase, a single stranded DNA ligase). In some instances, the ligase is T4 DNA ligase. In some instances, the ligase is T4 RNA ligase 2, also known as Rn12, which ligates the 3' hydroxyl end of a RNA to the 5' phosphate of DNA in a double stranded structure. T4 DNA ligase is an enzyme belonging to the DNA ligase family of enzymes that catalyzes the formation of a covalent phosphodiester bond from a free 3' hydroxyl group on one DNA molecule and a free 5' phosphate group of a second, separate DNA molecule, thus covalently linking the two DNA strands together to form a single DNA strand. In some instances, the ligase is splintR ligase. SplintR Ligase, also known as PBCV-1 DNA Ligase or Chorella virus DNA Ligase, efficiently catalyzes the coupling (e.g., ligation) of adjacent, single-stranded DNA oligonucleotides splinted by a complementary RNA strand. In some instances, the ligase is a single-stranded DNA ligase. In some embodiments, the ligase is a pre-activated T4 DNA ligase. Methods of utilizing a pre-activated T4 DNA ligase are further disclosed in U.S. Publication No. 2010-0184618-A1, which is incorporated by reference in its entirety.

In some embodiments, adenosine triphosphate (ATP) is added during the ligation reaction. DNA ligase-catalyzed sealing of nicked DNA substrates is first activated through ATP hydrolysis, resulting in covalent addition of an AMP group to the enzyme. After binding to a nicked site in a DNA duplex, the ligase transfers this AMP to the phosphorylated 5'-end at the nick, forming a 5'-5' pyrophosphate bond. Finally, the ligase catalyzes an attack on this pyrophosphate bond by the OH group at the 3'-end of the nick, thereby sealing it, whereafter ligase and AMP are released. If the ligase detaches from the substrate before the 3' attack, e.g. because of premature AMP reloading of the enzyme, then the 5' AMP is left at the 5'-end, blocking further coupling (e.g., ligation) attempts. In some instances, ATP is added at a concentration of about 1 µM, about 10 µM, about 100 µM, about 1000 µM, or about 10000 µM during the coupling (e.g., ligation) reaction.

In some instances, cofactors that aid in ligating of the probes are added during the ligation process. In some instances, the cofactors include magnesium ions ($Mg^{2+}$). In some instances, the cofactors include manganese ions ($Mn^{2+}$). In some instances, $Mg^{2+}$ is added in the form of $MgCl_2$. In some instances, $Mn^{2+}$ is added in the form of $MnCl_2$. In some instances, the concentration of $MgCl_2$ is at about 1 mM, at about 10 mM, at about 100 mM, or at about 1000 mM. In some instances, the concentration of $MnCl_2$ is at about 1 mM, at about 10 mM, at about 100 mM, or at about 1000 mM.

In some instances, the ligation reaction occurs at a pH in the range of about 6.5 to 9.0, of about 6.5 to 8.0, of about 7.5 to 8.0, of about 7.5, or of about 8.0.

In some instances, a single probe having multiple sequences that hybridize to a nucleic acid is used. For example, in some instances, the first probe and the second probe are on a contiguous nucleic acid. In some instances, the first probe is on the 3' end of the contiguous nucleic acid and the second probe is on the 5' end of the contiguous nucleic acid (or vice versa). As described above, in some instances, the two sequences of hybridization can be adjacent to one another, or they can hybridize to sequences that have a gap sequence between the two sites of hybridization. In some instances, a circular nucleic acid can be formed and amplified (e.g., using rolling circle amplification). In some instances, the circularized sequence can be digested (e.g., using an endonuclease), creating a linear nucleic acid that can be captured and identified using two slide methods disclosed herein. Thus, in some instances, the single probe includes one or more restriction sites that is designed to be unique to the probe and is not found in an analyte of interest. Any endonuclease known in the art can be used so long as it meets these criteria.

In some embodiments, methods are provided herein for amplifying the contiguous nucleic acid, where amplification of the contiguous nucleic acid increases the number of copies of the contiguous nucleic acid. In some embodiments where a contiguous nucleic acid is amplified, the amplification is performed by rolling circle amplification. In some embodiments, the contiguous nucleic acid to be amplified includes sequences (e.g., docking sequences, functional sequences, and/or primer sequences) that enable rolling circle amplification. In one example, the contiguous nucleic acid can include a functional sequence that is capable of binding to a primer used for amplification. In another example, the contiguous nucleic acid can include one or more docking sequences (e.g., a first docking sequence and a second docking sequence) that can hybridize to one or more oligonucleotides (e.g., a padlock probe(s)) used for rolling circle amplification.

As used herein, a "padlock probe" refers to an oligonucleotide that has, at its 5' and 3' ends, sequences that are complementary to adjacent or nearby target sequences (e.g., docking sequences) on a target nucleic acid sequence. Upon hybridization to the target sequences (e.g., docking sequences), the two ends of the padlock probe are either brought into contact or an end is extended until the two ends are brought into contact, allowing circularization of the padlock probe by ligation (e.g., ligation using any of the methods described herein). In some embodiments, after circularization of the oligonucleotide, rolling circle amplification can be used to amplify the ligation product, which includes the contiguous nucleic acid.

In some instances, probes (e.g., a first probe and a second probe) are ligated with the aid of a splint oligonucleotide. In some instances, the splint oligonucleotide includes a first splint sequence that is substantially complementary to the first probe or a portion thereof and a second splint sequence that is substantially complementary to the second probe or a portion thereof. The splint oligonucleotide can be between 10 and 100 (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100) nucleotides in length. In some instances, the splint oligonucleotide aids in ligation of the first probe and the second probe. Methods including a splint oligonucleotide have been described in U.S. Patent Pub. No. 2019/0055594A1, which is herein incorporated by reference in its entirety.

In some embodiments, after the step of hybridizing the probes to the nucleic acid, a wash step is performed to remove unbound probes. The wash step can be performed using any of the wash methods and solutions described herein. In some embodiments, after the washing step, the first and second probes are bound to (e.g., hybridized to) the analyte, and the splint oligonucleotide is bound to (e.g., hybridized to) the first and second oligonucleotides (e.g., at portions of the first and second probes that are not bound to the analyte). In some embodiments, the first probe, the second probe, and/or the splint oligonucleotide are added to the biological sample at the same time. In some embodiments, the first probe and the second probe are added at a first time point, and the splint oligonucleotide is added to the biological sample at a second time point.

Addition of Methylated Adaptors

Provided herein are methods for identifying a methylation status of DNA in a biological sample, the method comprising: (a) providing one or more methylated adaptors and a transposase enzyme to the biological sample under conditions wherein the one or more methylated adaptors is inserted into the DNA; (b) contacting the sequence comprising the analyte and the one or more methylated adaptors with an array comprising a plurality of capture probes, wherein a capture probe in the plurality of capture probes comprises a spatial barcode, wherein if the capture probe comprises one or more cytosines, then the one or more cytosines are methylated cytosines; (c) ligating the sequence comprising the analyte and the one or more methylated adaptors to the capture probe, thereby creating a ligation product; (d) deaminating the ligation product; (e) determining (i) all or a portion of the sequence of the spatial barcode or the complement thereof, and (ii) all or a portion of the sequence of the ligation product, or a complement thereof, and using the determined sequences of (i) and (ii) to identify the methylation status of the analyte in the biological sample.

In some embodiments, the method further comprises allowing the transposase enzyme to fragment the DNA and insert the methylated adaptors, thereby generating a sequence comprising an analyte and the one or more methylated adaptors, prior to step (b).

Also provided herein are methods for identifying a methylation status of a nucleic acid in a biological sample on a spatial array, the method comprising: (a) ligating methylated adaptors onto the 5' and/or 3' ends of fragmented nucleic acids, thereby generating an adapted nucleic acid fragment; (b) deaminating the adapted nucleic acid fragment; (c) capturing the adapted nucleic acid fragment onto a spatial array comprising a plurality of capture probes, wherein a capture probes comprise a spatial barcode; (d) determining (i) all or a portion of the sequence of the spatial barcode or the complement thereof, and (ii) all or a portion of the sequence of the methylated adaptor/nucleic acid, or a complement thereof, and using the determined sequences of (i) and (ii) to identify the methylation status of the analyte, or a portion thereof, in the biological sample.

In some instances, a methylated adaptor is ligated to a nucleic acid at a 5' end of the nucleic acid. In some instances, a methylated adaptor is ligated to a nucleic acid at a 3' end of the nucleic acid. In some instances, methylated adaptors are ligated to a nucleic acid at the 5' end and the 3' end of the nucleic acid. In some embodiments, the methylated adaptor is a methylated capture handle.

In some instances, a methylated adaptor is from 10 to 75 (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75) nucleotides in length. In some instances, the methylated adaptor is single-stranded. In some instances, the methylated adaptor is double-stranded. In some instances, the methylated adaptor is a DNA molecule.

In some instances, the methylated adaptor includes one or more methylated cytosine, which is protected from mutation caused during deamination. For instances, in some embodiments, the methylated adaptor includes at least 2, 3, 4, 5, 6, 7, 8, 9, 10, or more methylated cytosines.

In some instances, the methylated adaptor is ligated to nucleic acids by tagmentation.

In some embodiments, step (a) further comprises allowing a transposase enzyme to fragment the analytes, e.g., nucleic acids, and insert the methylated adaptors, thereby generating one or more sequences, each comprising a nucleic acid analyte and the one or more methylated adaptors (i.e., an adapted (e.g., tagmented) nucleic acid fragment).

A method for spatial transcriptome analysis using a transposase enzyme is described in U.S. Patent Publication No. WO 2020/047002, which is incorporated herein by reference in its entirety.

As used herein, "tagmentation" refers to a process of transposase-mediated fragmentation and tagging of DNA. Tagmentation typically involves the modification of DNA by a transposome complex and results in the formation of "tagments", or tagged DNA fragments.

As used herein, a "transposome" or "transposome complex" is a complex of a transposase enzyme and DNA which comprises transposon end sequences (also known as "transposase recognition sequences" or "mosaic ends" (ME)).

A "transposase" is an enzyme that binds to the end of a transposon and catalyzes its movement to another part of the genome by a cut and paste mechanism or a replicative transposition mechanism.

The DNA that forms a complex with a transposase enzyme (i.e. the transposon or ME sequences) contains a partially double stranded (e.g. DNA) oligonucleotide, wherein each strand contains a transposase specific sequence which forms the double stranded part of the oligonucleotide. The single-stranded portion of the oligonucleotide is at the 5' end of the oligonucleotide (i.e. forms a 5' overhang) and may comprise a functional sequence (e.g. a capture probe binding site, an adaptor sequence, etc.). Thus, the partially double stranded oligonucleotides in the transposome may be viewed as adaptors that can be ligated to the fragmented DNA. A transposome comprises a transposase enzyme complexed with one or more adaptors comprising transposon end sequences (or mosaic ends) and tagmentation results in the simultaneous fragmentation of DNA and ligation (e.g., tagging) of the adapters to the 5' ends of both ends of DNA duplex fragments. In some embodiments, an adaptor is methylated (e.g., comprising one or more methylated cytosines).

It will be evident that tagmentation can be used to provide fragmented DNA with a domain capable of hybridizing and/or ligating to the capture domain of the capture probes of the invention. Moreover, the domain may be provided directly or indirectly.

For example, in some embodiments, the adaptors of the transposome comprise a functional domain or sequence that may be configured to hybridize to all or a portion of a capture domain. The functional domain or sequence may be a domain capable of hybridizing to the capture domain of the capture probes of the invention (e.g. a homopolymeric sequence, e.g. poly-A sequence). In other words, the single-stranded portion of an adaptor comprises a domain capable of hybridizing to the capture domain of the capture probes of the invention. Accordingly, tagmentation results in the fragmentation of DNA of the biological specimen and ligation of the domain capable of hybridizing to the capture domain of the capture probes of the invention to the DNA of the biological specimen, i.e. providing the DNA of the biological specimen with a domain complementary to the capture probe capture domain directly.

In one embodiment, the functional domain or sequence is configured to attach to a portion of the capture domain through click chemistry. As used herein, the term "click chemistry," generally refers to reactions that are modular, wide in scope, give high yields, generate only inoffensive byproducts, such as those that can be removed by nonchromatographic methods, and are stereospecific (but not necessarily enantioselective). See, e.g., Angew. Chem. Int. Ed., 2001, 40(11):2004-2021, which is incorporated herein by reference in its entirety. In some cases, click chemistry can describe pairs of functional groups that can selectively react with each other in mild, aqueous conditions.

In some embodiments, an adaptor of a transposome comprises (i) a domain capable of (i.e. suitable for) facilitating the introduction of a click chemistry moiety(ies) configured to interact with another click chemistry moiety (ies) which can be associated with the capture domain of the capture probes of the invention.

An example of a click chemistry reaction can be the Huisgen 1,3-dipolar cycloaddition of an azide and an alkyne, i.e., Copper-catalyzed reaction of an azide with an alkyne to form a 5-membered heteroatom ring called 1,2,3-triazole. The reaction can also be known as a Cu(I)-Catalyzed Azide-Alkyne Cycloaddition (CuAAC), a Cu(I) click chemistry or a Cu+ click chemistry. Catalyst for the click chemistry can be Cu(I) salts, or Cu(I) salts made in situ by reducing Cu(II) reagent to Cu(I) reagent with a reducing reagent (Pharm Res. 2008, 25(10): 2216-2230). Known Cu(II) reagents for the click chemistry can include, but are not limited to, Cu(II)-(TBTA) complex and Cu(II) (THPTA) complex. TBTA, which is tris-[(1-benzyl-1H-1,2,3-triazol- 4-yl)methyl]amine, also known as tris-(benzyltriazolylmethyl)amine, can be a stabilizing ligand for Cu(I) salts. THPTA, which is tris-(hydroxypropyltriazolylmethyl)amine, can be another example of stabilizing agent for Cu(I). Other conditions can also be accomplished to construct the 1,2,3-triazole ring from an azide and an alkyne using copper-free click chemistry, such as by the Strain-promoted Azide-Alkyne Click chemistry reaction (SPAAC, see, e.g., Chem. Commun., 2011, 47:6257-6259 and Nature, 2015, 519 (7544):486-90), each of which is incorporated herein by reference in its entirety.

In another embodiment, an adaptor of a transposome may comprise a nucleotide sequence that templates the ligation of a universal adaptor to the tagmented DNA. The universal adaptor comprises a domain capable of hybridizing to the capture domain of the capture probes of the invention. Thus, in some embodiments, tagmentation provides the DNA of the biological specimen with a domain capable of hybridizing with the capture domain of a capture probe indirectly.

In another embodiment, an adaptor of a transposome may comprise a nucleotide sequence that is a substrate in a ligation reaction that introduces a universal adaptor to the tagmented DNA, e.g. a domain to which a universal adaptor may bind. For instance, the universal adaptor may be a partially double-stranded oligonucleotide having a first strand comprising a single-stranded portion containing domain that binds to the adaptor sequence ligated to the fragmented (i.e. tagmented) DNA and a second strand comprising a domain that binds to the first strand and a domain capable of binding (hybridizing) to the capture domain of the capture probes of the invention. Ligation of the universal adaptor to the fragmented (i.e. tagmented) DNA provides the tagmented DNA with a domain that binds to the capture domain of the capture probes of the invention. Thus, in some embodiments, tagmentation provides the DNA of the biological specimen with a binding domain indirectly.

As tagmentation results in DNA that comprises gaps between the 3' ends of the DNA of the biological specimen and the 5' ends at the double stranded portion of the adaptors (i.e. the 5' ends of the adaptors containing the MEs are not ligated to the 3' ends of the fragmented DNA of the biological specimen), providing the tagmented DNA with a binding domain capable of binding (hybridizing) to the capture domain of the capture probes of the invention may require a step of "gap filling" the tagmented DNA.

Gap filling may be achieved using a suitable polymerase enzyme, i.e. a DNA polymerase (e.g. selected from the list below). In this respect, the 3' ends of the tagmented DNA are extended using the complementary strands of the tagmented DNA as templates. Once the gaps have been filled, the 3' ends of the tagmented DNA are joined to the 5' ends of the adaptors by a ligation step, using a suitable ligase enzyme.

It will be understood in this regard that the 5' end of adaptors containing the ME is phosphorylated to enable ligation to take place. The transposome may comprise an adaptor in which one or both 5' ends are phosphorylated. In embodiments where the transposome comprises an adaptor in which the 5' end of adaptor containing the ME is not phosphorylated, the gap filling process may comprise a further step of phosphorylating the 5' end of the adaptor, e.g. using a kinase enzyme, such as T4 polynucleotide kinase.

In some embodiments, the 3' ends of the tagmented DNA may be extended using a DNA polymerase with strand displacement activity using the complementary strands of the tagmented DNA as templates. This results in the displacement of the strands of the adaptors that are not ligated to the fragmented DNA and the generation of fully double stranded DNA molecules. These molecules may be provided with a domain capable of binding to the capture domain of the capture probes by any suitable means, e.g. ligation of adaptors, "tailing" with a terminal transferase enzyme etc.

Thus, in some embodiments, the method comprises a step of extending the 3' ends of the fragmented (i.e. tagmented) DNA using a polymerase with strand displacement activity to produce fully double stranded DNA molecules.

In some embodiments, the fully double stranded DNA molecules may be provided with a binding domain capable of binding to the capture domain of the capture probes on a spatial array. In some embodiments, a binding domain may be provided by ligation of adaptors to the double stranded DNA molecules or via the use of a terminal transferase active enzyme to incorporate a polynucleotide tail, e.g. homopolymeric sequence (e.g. a poly-A tail), at the 3' ends of the double stranded DNA molecules.

Transposase Tn5 is a member of the RNase superfamily of proteins. The Tn5 transposon is a composite transposon in which two near-identical insertion sequences (IS50L and IS50R) flank three antibiotic resistance genes. Each IS50 contains two inverted 19-bp end sequences (ESs), an outside end (OE) and an inside end (IE).

A hyperactive variant of the Tn5 transposase is capable of mediating the fragmentation of double-stranded DNA and ligation of synthetic oligonucleotides (adaptors) at both 5' ends of the DNA in a reaction that takes about 5 minutes. However, as wild-type end sequences have a relatively low activity, they are preferably replaced in vitro by hyperactive mosaic end (ME) sequences. A complex of the Tn5 transposase with 19-bp ME is thus all that is necessary for transposition to occur, provided that the intervening DNA is long enough to bring two of these sequences close together to form an active Tn5 transposase homodimer.

Methods, compositions, and kits for treating nucleic acid, and in particular, methods and compositions for fragmenting and tagging DNA using transposon compositions are described in detail in US2010/0120098 and US2011/0287435, which are hereby incorporated by reference in their entireties.

Thus, any transposase enzyme with tagmentation activity, i.e. capable of fragmenting DNA and ligating oligonucleotides to the ends of the fragmented DNA, may be used in the methods of the present invention. In some embodiments, the transposase is a Tn5, Tn7, or Mu transposase or a functional variant or derivative thereof.

The tagmentation of the nucleic acid in the biological sample can be performed before or after the deamination of the nucleic acid. In some embodiments, the nucleic acid is deaminated prior to the tagmentation. In some embodiments, the nucleic acid is deaminated after the tagmentation.

In some embodiments, the method further comprises washing the biological sample. In some instances, a wash step occurs before or after the deamination step. In some embodiments, the washing step is conducted to remove all or a part of the deaminating agent. In some embodiments, the washing step does not remove the analyte in the biological sample. In some embodiments, the washing step removes an insignificant amount of the analyte in the biological sample. In some instances, a wash step occurs after hybridizing the oligonucleotides. In some instances, this wash step removes any unbound oligonucleotides and can be performed using any technique or solution disclosed herein or known in the art. In some embodiments, multiple wash steps are performed to remove unbound oligonucleotides.

Two-Slide Method Processes

In some embodiments, the alignment of the first substrate and the second substrate is facilitated by a sandwiching process. Accordingly, described herein are methods of positioning together the first substrate as described herein with a second substrate having an array with capture probes.

Figure 12:
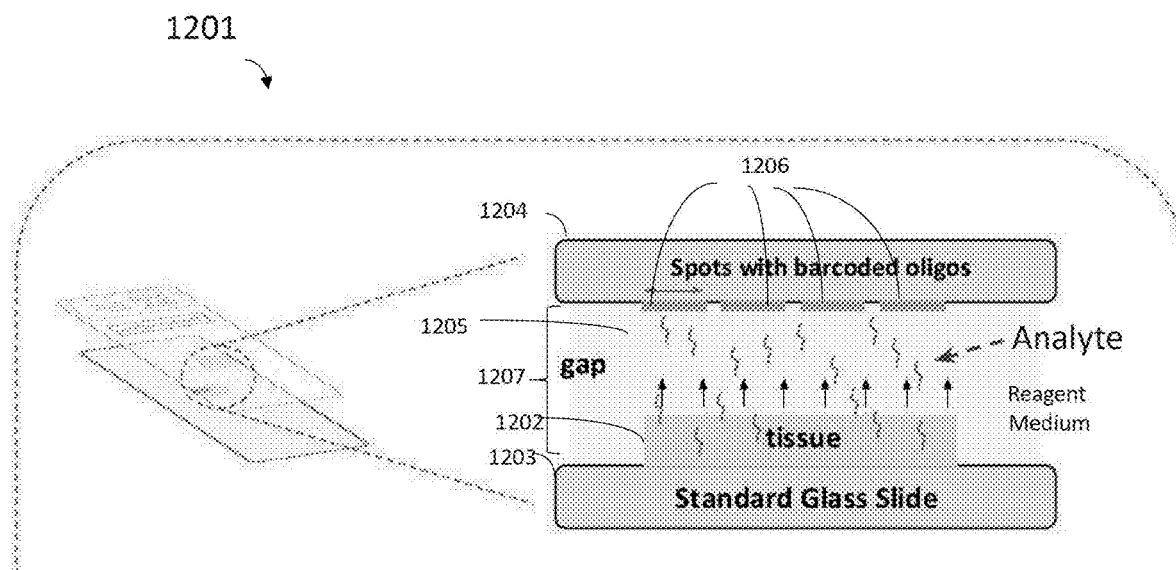
FIG. 12 shows a schematic diagram depicting an exemplary two slide spatial array embodiment.

FIG. 12 is a schematic diagram depicting an exemplary sandwiching process 1201 between a first substrate comprising a biological sample (e.g., a tissue section 1202 on a pathology slide 1203) and a second substrate comprising a spatially barcoded array, e.g., a slide 1204 that is populated with spatially-barcoded capture probes 1206. During the exemplary sandwiching process, the first substrate is aligned with the second substrate, such that at least a portion of the biological sample is aligned with at least a portion of the array (e.g., aligned with the array area superior or inferior to the biological sample). As shown, the arrayed slide 1204 is in a superior position to the pathology slide 1203. In some embodiments, the pathology slide 1203 may be positioned superior to the arrayed slide 1204. In some embodiments, the first and second substrates are aligned to maintain a gap or separation distance 1207 between the two substrates. When the first and second substrates are aligned, one or more analytes are released from the biological sample and actively or passively migrated to the array for capture. In some embodiments, the migration occurs while the aligned portions of the biological sample and the array are contacted with a reagent medium 1205. The released one or more analytes may actively or passively migrate across the gap 1207 via the reagent medium 1205 toward the capture probes 1206, and be captured by the capture probes 1206.

In some embodiments, the separation distance in the gap 1207 between first and second substrates is maintained between 2 microns and 1 mm (e.g., between 2 microns and 800 microns, between 2 microns and 700 microns, between 2 microns and 600 microns, between 2 microns and 500 microns, between 2 microns and 400 microns, between 2 microns and 300 microns, between 2 microns and 200 microns, between 2 microns and 100 microns, between 2 microns and 25 microns, between 2 microns and 10 microns), measured in a direction orthogonal to the surface of first substrate that supports sample. In some instances, the distance is 2 microns. In some instances, the distance is 2.5 microns. In some instances, the distance is about 2, 3, 4, 5, 6, 7, 8, 9, 10, 11, 12, 13, 14, 15, 16, 17, 18, 19, 20, 21, 22, 23, 24, or 25 microns. In some embodiments, second substrate is placed in direct contact with the sample on the first substrate ensuring no diffusive spatial resolution losses. In some embodiments, the separation distance is measured in a direction orthogonal to a surface of the first substrate that supports the biological sample.

In some embodiments, the first and second substrates are placed in a substrate holder (e.g., an array alignment device) configured to align the biological sample and the array. In some embodiments, the device comprises a sample holder. In some embodiments, the sample holder includes a first and second member that receive a first and second substrate, respectively. The device can include an alignment mechanism that is connected to at least one of the members and aligns the first and second members. Thus, the devices of the disclosure can advantageously align the first substrate and the second substrate and any samples, barcoded probes, or permeabilization reagents that may be on the surface of the first and second substrates. Exemplary devices and exemplary sample holders are described in PCT Patent Application Publication No. WO 2020/123320, which is incorporated by reference in its entirety.

In some embodiments, the reagent medium comprises a permeabilization agent. Suitable agents for this purpose include, but are not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). Exemplary permeabilization reagents are described in in PCT Patent Application Publication No. WO 2020/123320, which is incorporated by reference in its entirety.

In some embodiments, the reagent medium comprises a lysis reagent. Lysis solutions can include ionic surfactants such as, for example, sarkosyl and sodium dodecyl sulfate (SDS). More generally, chemical lysis agents can include, without limitation, organic solvents, chelating agents, detergents, surfactants, and chaotropic agents. Exemplary lysis reagents are described in PCT Patent Application Publication No. WO 2020/123320, which is incorporated by reference in its entirety.

In some embodiments, the reagent medium comprises a protease. Exemplary proteases include, e.g., pepsin, trypsin, pepsin, elastase, and proteinase K. Exemplary proteases are described in PCT Patent Application Publication No. WO 2020/123320, which is incorporated by reference in its entirety.

In some embodiments, the reagent medium comprises a detergent. Exemplary detergents include sodium dodecyl sulfate (SDS), sarkosyl, saponin, Triton X-100', and Tween-20™. Exemplary detergents are described in PCT Patent Application Publication No. WO 2020/123320, which is incorporated by reference in its entirety.

In some embodiments, the reagent medium comprises a nuclease. In some embodiments, the nuclease comprises an RNase. In some embodiments, the RNase is selected from RNase A, RNase C, RNase H, and RNase I. In some embodiments, the reagent medium comprises one or more of sodium dodecyl sulfate (SDS), proteinase K, pepsin, N-lauroylsarcosine, RNAse, and a sodium salt thereof.

The sample holder is compatible with a variety of different schemes for contacting the aligned portions of the biological sample and array with the reagent medium to promote analyte capture. In some embodiments, the reagent medium is deposited directly on the second substrate (e.g., forming a reagent medium that includes the permeabilization reagent and the feature array), and/or directly on the first substrate. In some embodiments, the reagent medium is deposited on the first and/or second substrate, and then the first and second substrates aligned in the disclosed configuration such that the reagent medium contacts the aligned portions of the biological sample and array. In some embodiments, the reagent medium is introduced into the gap 1207 while the first and second substrates are aligned in the disclosed configuration.

In certain embodiments a dried permeabilization reagent is applied or formed as a layer on the first substrate or the second substrate or both prior to contacting the sample and the feature array. For example, a reagent can be deposited in solution on the first substrate or the second substrate or both and then dried. Drying methods include, but are not limited to spin coating a thin solution of the reagent and then evaporating a solvent included in the reagent or the reagent itself. Alternatively, in other embodiments, the reagent can be applied in dried form directly onto the first substrate or the second substrate or both. In some embodiments, the coating process can be done in advance of the analytical workflow and the first substrate and the second substrate can be stored pre-coated. Alternatively, the coating process can be done as part of the analytical workflow. In some embodiments, the reagent is a permeabilization reagent. In some embodiments, the reagent is a permeabilization enzyme, a buffer, a detergent, or any combination thereof. In some embodiments, the permeabilization enzyme is pepsin. In some embodiments, the reagent is a dried reagent (e.g., a reagent free from moisture or liquid). In some instances, the substrate that includes the sample (e.g., a histological tissue section) is hydrated. The sample can be hydrated by contacting the sample with a reagent medium, e.g., a buffer that does not include a permeabilization reagent. In some embodiments, the hydration is performed while the first and second substrates are aligned in a sandwich style configuration.

In some instances, the aligned portions of the biological sample and the array are in contact with the reagent medium 1205 in the gap 1207 for about 1 minute. In some instances, the aligned portions of the biological sample and the array are in contact with the reagent medium 1205 for about 5 minutes. In some instances, the aligned portions of the biological sample and the array are in contact with the reagent medium 1205 in the gap 1207 for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the aligned portions of the biological sample and the array are in contact with the reagent medium 1205 for about 1-60 minutes. In some instances, the aligned portions of the biological sample and the array are in contact with the reagent medium 1205 for about 30 minutes.

In some embodiments, following initial contact between a sample and a permeabilization agent, the permeabilization agent can be removed from contact with the sample (e.g., by opening the sample holder) before complete permeabilization of the sample. For example, in some embodiments, only a portion of the sample is permeabilized, and only a portion of the analytes in the sample may be captured by the feature array. In some instances, the reduced amount of analyte captured and available for detection can be offset by the reduction in lateral diffusion that results from incomplete permeabilization of the sample. In general, the spatial resolution of the assay is determined by the extent of analyte diffusion in the transverse direction (i.e., orthogonal to the normal direction to the surface of the sample). The larger the distance between the sample on the first substrate and the feature array on the second substrate, the greater the extent of diffusion in the transverse direction, and the concomitant loss of resolution. Analytes liberated from a portion of the sample closest to the feature array have a shorter diffusion path, and therefore do not diffuse as far laterally as analytes from portions of the sample farthest from the feature array. As a result, in some instances, incomplete permeabilization of the sample (by reducing the contact interval between the permeabilization agent and the sample) can be used to maintain adequate spatial resolution in the assay.

In some instances, the device is configured to control a temperature of the first and second substrates. In some embodiments, the temperature of the first and second members is lowered to a first temperature that is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower). In some embodiments, the device includes a temperature control system (e.g., heating and cooling conducting coils) to control the temperature of the sample holder. Alternatively, in other embodiments, the temperature of the sample holder is controlled externally (e.g., via refrigeration or a hotplate). In a first step, the second member, set to or at the first temperature, contacts the first substrate, and the first member, set to or at the first temperature, contacts the second substrate, thereby lowering the temperature of the first substrate and the second substrate to a second temperature. In some embodiments, the second temperature is equivalent to the first temperature. In some embodiments, the first temperature is lower than room temperature (e.g., 25 degrees Celsius). In some embodiments, the second temperature ranges from about −10 degrees Celsius to about 4 degrees Celsius. In some embodiments, the second temperature is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower).

In an exemplary embodiment, the second substrate is contacted with the permeabilization reagent. In some embodiments, the permeabilization reagent is dried. In some embodiments, the permeabilization reagent is a gel or a liquid. Also in the exemplary embodiments, the biological sample is contacted with buffer. Both the first and second substrates are placed at lower temperature to slow down diffusion and permeabilization efficiency. Alternatively, in some embodiments, the sample can be contacted directly with a liquid permeabilization reagent without inducing an unwanted initiation of permeabilization due to the substrates being at the second temperature. In some embodiments, the low temperature slows down or prevents the initiation of permeabilization. In a second step, keeping the sample holder and substrates at a cold temperature (e.g., at the first or second temperatures) continues to slow down or prevent the permeabilization of the sample. In a third step, the sample holder (and consequently the first and second substrates) is heated up to initiate permeabilization. In some embodiments, the sample holder is heated up to a third temperature. In some embodiments, the third temperature is above room temperature (e.g., 25 degrees Celsius) (e.g., 30 degrees Celsius or higher, 35 degrees Celsius or higher, 40 degrees Celsius or higher, 50 degrees Celsius or higher, 60 degrees Celsius or higher). In some embodiments, analytes that are released from the permeabilized tissue of the sample diffuse to the surface of the second substrate and are captured on the array (e.g., barcoded probes) of the second substrate. In a fourth step, the first substrate and the second substrate are separated (e.g., pulled apart) and temperature control is stopped.

In some embodiments, where either the first substrate or second substrate (or both) includes wells, a permeabilization solution can be introduced into some or all of the wells, and the sample and the feature array can be contacted by closing the sample holder to permeabilize the sample. In certain embodiments, a permeabilization solution can be soaked into a hydrogel film that is applied directly to the sample, and/or soaked into features (e.g., beads) of the array. When the first and second substrates are aligned in the sandwich type configuration, the permeabilization solution promotes migration of analytes from the sample to the array.

In certain embodiments, different permeabilization agents or different concentrations of permeabilization agents can be infused into array features (e.g., beads) or into a hydrogel layer as described above. By locally varying the nature of the permeabilization reagent(s), the process of analyte capture from the sample can be spatially adjusted.

In some instances, migration of the analyte from the biological sample to the second substrate is passive (e.g., via diffusion). Alternatively, in certain embodiments, migration of the analyte from the biological sample is performed actively (e.g., electrophoretic, by applying an electric field to promote migration). In some instances, first and second substrates can include a conductive epoxy. Electrical wires from a power supply can connect to the conductive epoxy, thereby allowing a user to apply a current and generate an electric field between the first and second substrates. In some embodiments, electrophoretic migration results in higher analyte capture efficiency and better spatial fidelity of captured analytes (e.g., on a feature array) than random diffusion onto matched substrates without the application of an electric field (e.g., via manual alignment of the two substrates). Exemplary methods of electrophoretic migration, including those illustrated in FIGS. 6-9, are described in WO 2020/176788, including at FIGS. 14A-14B, 15, 24A-24B, and 25A-25C, which is hereby incorporated by reference in its entirety.

Loss of spatial resolution can occur when analytes migrate from the sample to the feature array and a component of diffusive migration occurs in the transverse (e.g., lateral) direction, approximately parallel to the surface of the first substrate on which the sample is mounted. To address this loss of resolution, in some embodiments, a permeabilization agent deposited on or infused into a material with anisotropic diffusion can be applied to the sample or to the feature array. The first and second substrates are aligned by the sample holder and brought into contact. A permeabilization layer that includes a permeabilization solution infused into an anisotropic material is positioned on the second substrate.

In some embodiments, the feature array can be constructed atop a hydrogel layer infused with a permeabilization agent. The hydrogel layer can be mounted on the second substrate, or alternatively, the hydrogel layer itself may function as the second substrate. When the first and second substrates are aligned, the permeabilization agent diffuses out of the hydrogel layer and through or around the feature array to reach the sample. Analytes from the sample migrate to the feature array. Direct contact between the feature array and the sample helps to reduce lateral diffusion of the analytes, mitigating spatial resolution loss that would occur if the diffusive path of the analytes was longer.

Spatial analysis workflows can include a sandwiching type process described herein, e.g., a process as described in FIG. 12. In some embodiments, the workflow includes provision of the first substrate comprising the biological sample. In some embodiments, the workflow includes, mounting the biological sample onto the first substrate. In some embodiments wherein the biological sample is a tissue sample, the workflow includes sectioning of the tissue sample (e.g., cryostat sectioning). In some embodiments, the workflow includes a fixation step. In some instances, the fixation step can include fixation with methanol. In some instances, the fixation step includes formalin (e.g., 2% formalin).

In some embodiments, the biological sample on the first substrate is stained using any of the methods described herein. In some instances, the biological sample is imaged, capturing the stain pattern created during the stain step. In some instances, the biological sample then is destained prior to the two slide process 1201.

The biological sample can be stained using known staining techniques, including, without limitation, Can-Grunwald, Giemsa, hematoxylin and eosin (H&E), hematoxylin, Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes biological staining using hematoxylin. In some embodiments, staining includes identifying analytes using fluorescently-conjugated antibodies, e.g., by immunofluorescence. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample. In some instances, a biological sample on the first substrate is stained.

In some instances, methods for immunofluorescence include a blocking step. The blocking step can include the use of blocking probes to decrease nonspecific binding of the antibodies. The blocking step can optionally further include contacting the biological sample with a detergent. In some instances, the detergent can include Triton X-100™. The method can further include an antibody incubation step. In some embodiments, the antibody incubation step effects selective binding of the antibody to antigens of interest in the biological sample. In some embodiments, the antibody is conjugated to an oligonucleotide (e.g., an oligonucleotide-antibody conjugate as described herein). In some embodiments, the antibody is not conjugated to an oligonucleotide. In some embodiments, the method further comprises an antibody staining step. The antibody staining step can include a direct method of immunostaining in which a labelled antibody binds directly to the analyte being stained for. Alternatively, the antibody staining step can include an indirect method of immunostaining in which a first antibody binds to the analyte being stained for, and a second, labelled antibody binds to the first antibody. In some embodiments, the antibody staining step is performed prior to the two-slide spatial array assembly. In some embodiments wherein an oligonucleotide-antibody conjugate is used in the antibody incubation step, the method does not comprise an antibody staining step.

In some instances, the methods include imaging the biological sample. In some instances, imaging occurs prior to a two-slide assembly. In some instances, imaging occurs while the two-slide configuration is assembled. In some instances, imaging occurs during permeabilization of the biological sample. In some instances, image are captured using high resolution techniques (e.g., having 300 dots per square inch (dpi) or greater). For example, images can be captured using brightfield imaging (e.g., in the setting of hematoxylin or H&E stain), or using fluorescence microscopy to detect adhered labels. In some instances, high resolution images are captured temporally using e.g., confocal microscopy. In some instances, a low resolution image is captured. A low resolution image (e.g., images that are about 72 dpi and normally have an RGB color setting) can be captured at any point of the workflow, including but not limited to staining, destaining, permeabilization, two-slide assembly, and migration of the analytes. In some instances, a low resolution image is taken during permeabilization of the biological sample.

In some embodiments, the location of the one or more analytes in a biological sample are determined by immunofluorescence. In some embodiments, one or more detectable labels (e.g., fluorophore-labeled antibodies) bind to the one or more analytes that are captured (hybridized to) by a probe on the first slide and the location of the one or more analytes is determined by detecting the labels under suitable conditions. In some embodiments, one or more fluorophore-labeled antibodies are used to conjugate to a moiety that associates with a probe on the first slide or the analyte that is hybridized to the probe on the first slide. In some instances, the location(s) of the one or more analytes is determined by imaging the fluorophore-labeled antibodies when the fluorophores are excited by a light of a suitable wavelength. In some embodiments, the location of the one or more analytes in the biological sample is determined by correlating the immunofluorescence data to an image of the biological sample. In some instances, the tissue is imaged throughout the permeabilization step.

In some instances, the biological samples can be destained. In some instances, destaining occurs prior to permeabilization of the biological sample. By way of example only, H&E staining can be destained by washing the sample in HCl. In some instances, the hematoxylin of the H&E stain is destained by washing the sample in HCl. In some embodiments, destaining can include 1, 2, 3, or more washes in HCl. In some embodiments, destaining can include adding HCl to a downstream solution (e.g., permeabilization solution).

Between any of the methods disclosed herein, the methods can include a wash step (e.g., with SSC (e.g., 0.1×SSC)). Wash steps can be performed once or multiple times (e.g., 1×, 2×, 3×, between steps disclosed herein). In some instances, wash steps are performed for about 10 seconds, about 15 seconds, about 20 seconds, about 30 seconds, or about a minute. In some instances, three washes occur for 20 seconds each. In some instances, the wash step occurs before staining the sample, after destaining the sample, before permeabilization the sample, after permeabilization the sample, or any combination thereof.

In some instances, after the sandwiching type process 1201 the first substrate and the second substrate are separated (e.g., such that they are no longer aligned in a sandwich type configuration). In some embodiments, subsequent analysis (e.g., cDNA synthesis, library preparation, and sequences) can be performed on the captured analytes after the first substrate and the second substrate are separated.

In some embodiments, the process of transferring the ligation product or methylated-adaptor-containing nucleic acid from the first substrate to the second substrate is referred to interchangeably herein as a "sandwich type or sandwich style process," or "two-slide process". The two-slide process is further described in PCT Patent Application Publication No. WO 2020/123320, which is incorporated by reference in its entirety.

Release of Deaminated Nucleic Acid, Capture on an Array, and Determination of Methylation Status In some embodiments, the methods described herein further comprise releasing the ligation product from the analyte, e.g., nucleic acid, on the first substrate and is captured on a second substrate using the sandwich type methods described herein. In some embodiments, the releasing occurs before capturing of the ligation product to the capture probe on the spatial array.

In some instances, the ligation product is dehybridized from the analyte by heating the sample. In some instances, the ligation product is dehybridized at about 50° C., about 55° C., about 60° C., about 65° C., about 70° C., or about 75° C. In some instances, the ligation product is dehybridized from the analyte electrochemically. In some instances, the ligation product is dehybridized using a solution comprising a base. In some instances, the base is potassium hydroxide (KOH). In some instances, the base is sodium hydroxide (NaOH). In some instances, to restore neutral pH after this step, an acid (e.g., a weak acid) having a pH below 7 (e.g., pH of 5, 5.5, 6, 6.5) can be added.

As described above, after release of the ligation product, it can migrate (actively or passively) to the second substrate and can be captured on the array on the second substrate.

In some instances, the second substrate comprises an array. In some instances, the array includes a plurality of capture probes, each of which includes a capture domain and a spatial barcode. In some embodiments, the capture probe is affixed to the substrate at a 5' end. In some embodiments, the plurality of capture probes are uniformly distributed on a surface of the substrate. In some embodiments, the plurality of capture probes are located on a surface of the substrate but are not distributed on the substrate according to a pattern. In some embodiments, the substrate (e.g., a second substrate) includes a plurality of capture probes, where a capture probe of the plurality of capture probes includes a capture domain and a spatial barcode.

In some embodiments, the capture domain includes a sequence that is at least partially complementary to the analyte or the analyte derived molecule. In some embodiments, the capture domain of the capture probe includes a poly(T) sequence. In some embodiments, the capture domain includes a functional domain. In some embodiments, the functional domain includes a primer sequence. In some embodiments, the capture probe includes a cleavage domain. In some embodiments, the cleavage domain includes a cleavable linker from the group consisting of a photocleavable linker, a UV-cleavable linker, an enzyme-cleavable linker, or a pH-sensitive cleavable linker.

The array can be any suitable array described herein. In some embodiments, the array comprises a slide. In some embodiments, the array includes a plurality of capture probes. In some embodiments, a 5' end of a capture probe in the plurality is attached to the slide. In some embodiments, the array is a bead array. In some embodiments, a 5' end of the capture probe is attached to a bead of the bead array. In some embodiments, the capture probe further comprises a unique molecular identifier (UMI). The UMI can be any suitable UMI described herein. In some embodiments, the UMI is positioned 5' relative to the capture domain in the capture probe. In some embodiments, the capture probe further comprises a functional sequence. In some embodiments, the functional sequence is a primer sequence. In some embodiments, the primer sequence is used to extend the capture probe.

In some embodiments, the capture domain of the capture probe comprises a sequence that specifically binds to the overhang sequence of one or more probes. The spatial barcode can be any suitable spatial barcodes described herein.

In some embodiments, methods provided herein include contacting a biological sample with a substrate, wherein the capture probe is affixed to the substrate (e.g., immobilized to the substrate, directly or indirectly). In some embodiments, the capture probe includes a spatial barcode and a capture domain. In some embodiments, the capture probe binding domain of the ligation product specifically binds to the capture domain. After hybridization of the ligation product to the capture probe, the ligation product is extended at the 3' end to make a copy of the additional components (e.g., the spatial barcode) of the capture probe. In some embodiments, methods of ligation product capture as provided herein include permeabilization of the biological sample such that the capture probe can more easily hybridize to the ligation product (i.e., compared to no permeabilization).

In some instances, after the ligation product hybridizes to the capture probe, the method disclosed herein includes extending the capture probe using the ligation product as a template; thereby generating an extended capture probe. In some instances, the capture probe is extended wherein each adenine, if present in the extended probe, is base-paired with a thymine. In some embodiments, the extended capture probe comprises a thymine in each position corresponding to the unmethylated cytosines in the analyte in the biological sample. In some embodiments, the methylated cytosines, e.g., 5-methylcytosine or 5-hydroxymethylcytosine, if present in the analyte in the sample, remain unchanged.

In some embodiments, amplification reagents can be added to second substrate. Incubation with the amplification reagents can produce spatially-barcoded DNA sequences. Second strand reagents (e.g., second strand primers, enzymes) can be added to the biological sample on the slide to initiate second strand DNA synthesis.

The resulting DNA can be denatured from the capture probe template and transferred (e.g., to a clean tube) for amplification, and/or library construction as described herein. The spatially-barcoded, full-length DNA can be amplified via PCR prior to library construction. The DNA can then be enzymatically fragmented and size-selected in order to optimize the DNA amplicon size. Sequencing specific nucleic acid sequences such as P5, P7, sample indices such as i7, and i5 and sequencing primer sequences such as TruSeq Read 2 (exemplary sequences that are used in Illumina NGS sequencing workflows) can be added via End Repair, A-tailing, Adaptor Ligation, and PCR. The cDNA fragments can then be sequenced using paired-end sequencing using TruSeq Read 1 and TruSeq Read 2 as sequencing primer sites. In some instances, the DNA library is sequenced using any method described herein.

In some embodiments, the capture probe, ligation product or a complement thereof, and/or analyte/methylated adaptor can be sequenced. In some instances, this is performed using a determining step. In some instances, the determining step comprises sequencing (i) all or a part of the sequence of the analyte, or a complement thereof, and (ii) all or a part of the sequence of the spatial barcode, or a complement thereof. The sequencing can be performed using any suitable methods described herein. In some embodiments, the sequencing is high throughput sequencing. In some embodiments, the sequencing is sequencing by hybridization. In some embodiments, the sequencing is sequencing by synthesis. In some embodiments, the sequencing is sequencing by ligation. In some embodiments, the sequencing is nanopore type sequencing.

In some embodiments, the methods described herein further comprises transferring an analyte to a spatial array (e.g., a spatial array on a substrate). In some embodiments, the methods further comprise a migration step wherein the analyte migrates to the substrate. In some embodiments, the migration is an active migration step. For example, the migration is through a microfluidic system or a concentration gradient of a reagent. In some embodiments, active migration is effected by electrophoretic means. In some embodiments, the migration is a passive migration step. For example, the migration follows gravity. In some embodiments, the analyte is a ligation product (e.g., a ligated probe). In some embodiments, the analyte is an adapted (e.g., tagmented) nucleic acid fragment. In some embodiments, the adapted (e.g., tagmented) nucleic acid fragment is deaminated.

In some embodiments, identification of the methylated cytosines is indicative of the methylation status of the analyte, e.g., nucleic acid. In some embodiments, the methylation status of the analyte is indicated by the percentage of methylated cytosines over all cytosines in the analyte. In some embodiments, the methods described herein further comprise comparing the determined sequence of the analyte with a reference sequence of the analyte, e.g., the sequence of the analyte without deamination. In some embodiments, the comparison comprises identifying thymines in the determined sequence of the analyte and comparing with the nucleotides in the corresponding positions in the reference sequence of the analyte, and determining that one or more thymines in the determined sequence using the methods described herein are unmethylated cytosines. In some embodiments, one or more cytosines in the analyte, e.g., DNA, can be methylated cytosines. In some embodiments, the determined sequence of the analyte comprises one or more cytosines, wherein the one or more cytosines are methylated cytosines. In some embodiments, about 0.0001% to about 50% (e.g., about 0.0001% to about 0.001%, about 0.001% to about 0.01%, about 0.01 to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.8% to about 0.9%, about 0.9% to about 1%, about 1% to about 2%, about 2% to about 3%, about 3% to about 4%, about 4% to about 5%, about 5% to about 6%, about 6% to about 7%, about 7% to about 8%, about 8% to about 9%, about 9% to about 10%, about 10% to about 15%, about 15% to about 20%, about 20% to about 25%, about 25% to about 30%, about 30% to about 35%, about 35% to about 40%, about 40% to about 45%, or about 45% to about 50%) of the cytosines in an analyte are methylated. In some embodiments, no cytosine in an analyte is methylated.

Figure 11A:
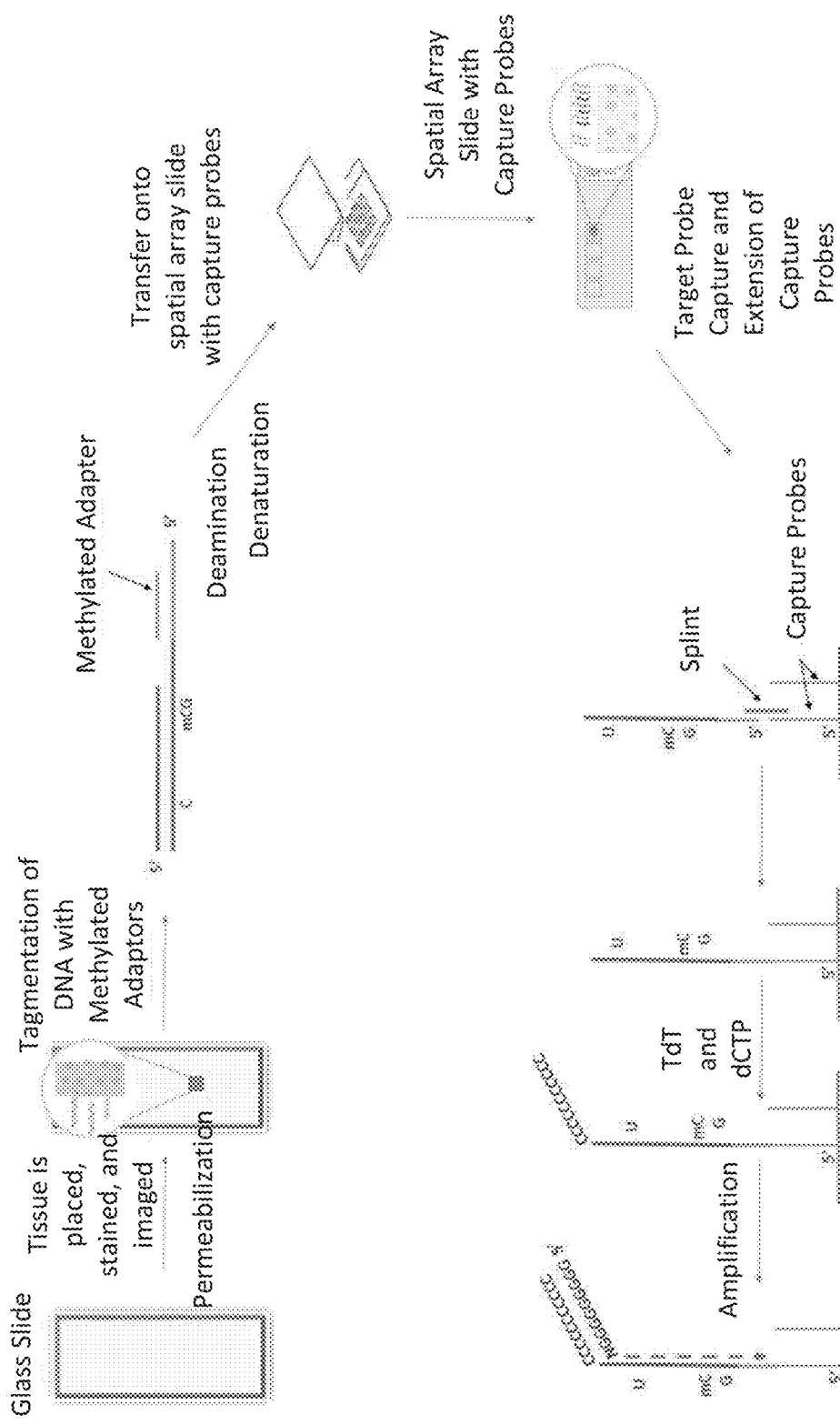
FIG. 11A shows a schematic of an example analytical workflow of generating a deaminated nucleic acid in a biological sample
Figure 11B:
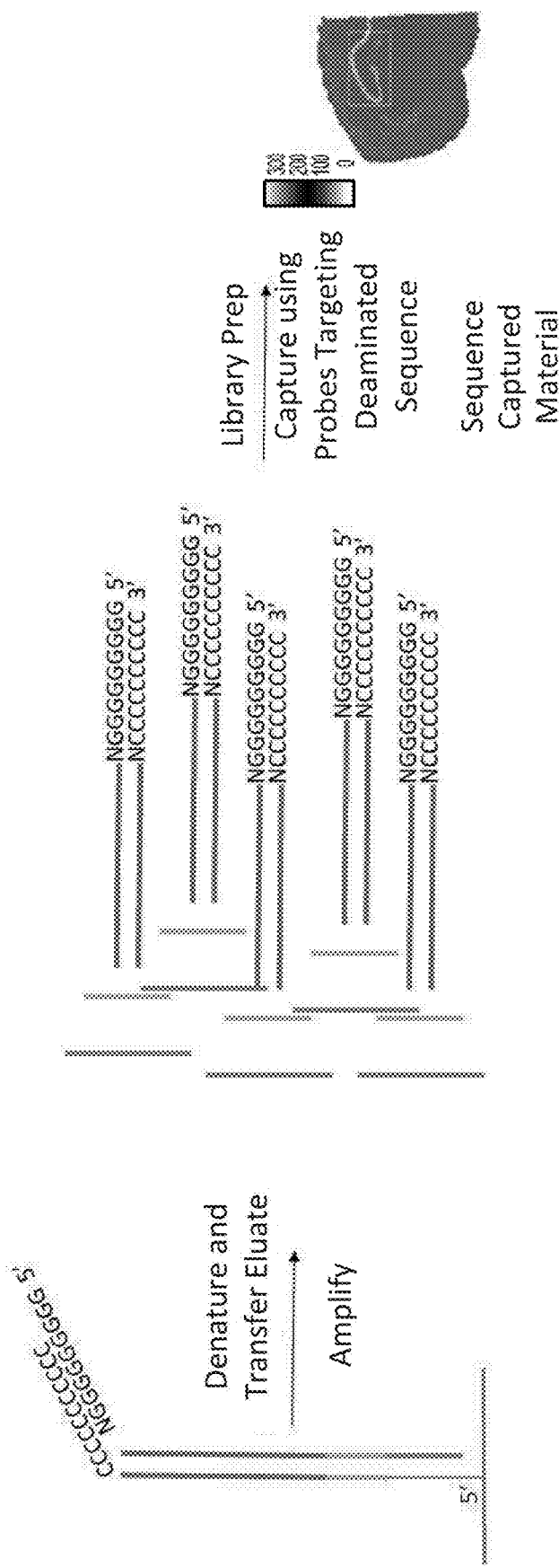
FIG. 11B shows a schematic of an example analytical workflow of identifying a methylation status of a deaminated nucleic acid in a biological sample.

In some instances, the percentage or abundance of methylated nucleotides can be determined and converted into an image, such as a heat map as shown in FIG. 11B. In some instances, the map is generated based on the percentage of methylated nucleotides (e.g., cytosines) or abundance of methylated nucleotides (e.g., cytosines) by determining the location of the methylated nucleotides (e.g., cytosines) using the location of the spatial barcode in the capture probe as provided by sequencing results.

In some embodiments, the methods provided herein comprise comparing the methylation status of the analyte at a location in the tissue sample to the DNA methylation status of a reference location in a reference tissue sample. In some embodiments, the reference location is a location in a healthy tissue, e.g., a healthy tissue corresponding to the tissue where the tissue sample is obtained. In some embodiments, the reference location is a location in a non-cancerous tissue. In some embodiments, the reference location is in a non-tumor tissue. In some embodiments, the reference location is a location in a tissue sample with no abnormalities such as tumor, cancer, or disease. In some embodiments, the reference location is in a sample identified as having cancer. In some instances, the reference location is a location that includes a tumor.

In some embodiments, the methylation status of the analyte in the tissue sample is different from the methylation status of an analyte in a reference location in a reference tissue sample. In some embodiments, the methylation of the analyte in the tissue sample is higher than the methylation of an analyte in a reference location. In some embodiments, the methylation of the analyte in the tissue sample is lower than the methylation of an analyte in a reference location. In some instances, the methylation status of a particular cytosine of an analyte is different from a cytosine in an analyte at a reference location. In some instances, a methyl group is located at a particular cytosine compared to a corresponding cytosine in the reference location. In some instances, a methyl group is not present at a particular cytosine compared to a methyl group present on a cytosine in the reference location. In some instances, the methylation status of the analyte includes at least 2, at least 3, at least 4, at least 5, at least 6, at least 7, at least 8, at least 9, at least 10, at least 20, at least 30, at least 40, at least 50, or more methyl groups compared to the corresponding cytosines in the reference location. In some instances, the methylation status of the analyte does not include at least 2, at least 3, at least 4, at least 5, at least 6, at least 7, at least 8, at least 9, at least 10, at least 20, at least 30, at least 40, at least 50, or more methyl groups compared to the corresponding cytosines in the reference location of a reference tissue sample.

Kits and Compositions

In some embodiments, also provided herein are kits and compositions that include one or more reagents to detect the methylation status of a nucleic acid in a biological sample.

In some instances, the kit or composition includes a first substrate as described herein. In some instances, the kit or composition includes a second substrate as described herein. In some instances, the kit or composition include means for releasing one or more nucleic acids and/or probes from a biological sample and allowing the one or more nucleic acids and/or probes to migrate to the second substrate. In some embodiments, the kit or composition includes a substrate comprising a plurality of capture probes, wherein a capture probe of the plurality of first capture probes comprises (i) a spatial barcode and (ii) a capture domain.

In some instances, the kit or composition includes one or more mixtures, reagents, or solutions for deaminating a nucleotide or nucleic acid. In some instances, the one or more mixtures, reagents, or solutions is sodium bisulfite.

In some embodiments, reagents can include one or more antibodies (and/or antigen-binding antibody fragments), labeled hybridization probes, and primers. For example, in some embodiments, an antibody (and/or antigen-binding antibody fragment) can be used for visualizing one or more features of a tissue sample (e.g., by using immunofluorescence or immunohistochemistry). In some embodiments, an antibody (and/or antigen-binding antibody fragment) can be an analyte binding moiety, for example, as part of an analyte capture agent. For example, in some embodiments, a kit can include an anti-PMCH antibody, such as Product No. HPA046055 (Atlas Antibodies), Cat. Nos. PA5-25442, PA5-84521, PA5-83802 (ThermoFisher Scientific), or Product No. AV13054 (MilliporeSigma). Other useful commercially available antibodies will be apparent to one skilled in the art.

In some embodiments, labeled hybridization probes can be used for in situ sequencing of one or more biomarkers and/or candidate biomarkers. In some embodiments, primers can be used for amplification (e.g., clonal amplification) of a captured oligonucleotide analyte.

In some embodiments, a kit or composition can include enzyme systems for performing DNA tagmentation on a target analyte. Enzyme systems can include one or more transposases, transposon sequences, adaptor sequences, either separately or combined into transposome complexes. In some embodiments, the enzyme is selected from the group consisting of a transposase, a ligase, a polymerase; a reverse transcriptase, a cytidine deaminase and a demethylase.

In some embodiments, a kit or composition can further include instructions for performing any of the methods or steps provided herein. In some embodiments, a kit or composition can include a substrate with one or more capture probes comprising a spatial barcode and a capture domain that captures a nucleic acid. In some instances, the methods includes means for sequencing the nucleic acid. In some instances, the kit includes reagents to detect and sequence the analyte. In some embodiments, the kit or composition further includes but is not limited to one or more antibodies (and/or antigen-binding antibody fragments), labeled hybridization probes, primers, or any combination thereof for visualizing one or more features of a tissue sample.

EXAMPLES

Example 1: Efficient Analyte Capture from Slide-Mounted Fresh Frozen Mouse Brain Sections onto Spatial Array Slides Analyte capture onto spatially barcoded arrays and subsequent sequencing was demonstrated under two-slide and control (not two-slide) conditions. For the two-slide condition, archived tissue-mounted on standard glass slides containing hematoxylin/eosin stained fresh frozen mouse brain sections were used. For the control condition, gene expression array slides with hematoxylin/eosin stained fresh frozen mouse brain sections mounted directly onto the array area were used. Under both conditions, tissue sections were subjected to a hematoxylin destaining step. Slides processed according to the two-slide condition were briefly dried at 37° C., then mounted in an instrument along with a gene expression slide and a permeabilization buffer comprising sarkosyl and proteinase K. Upon instrument closure (e.g., two-slides were positioned together in a sandwich type of configuration), the tissue sections were permeabilized for 1 minute. For the tissue-mounted gene expression slides processed according to the control condition, sections were permeabilized for 5 minutes using the same permeabilization buffer. For both conditions, following permeabilization, captured polyA-containing mRNA transcripts on the gene expression slides were reverse transcribed into cDNA, followed by standard sequencing library preparation and sequencing.

Figures 13, 14:
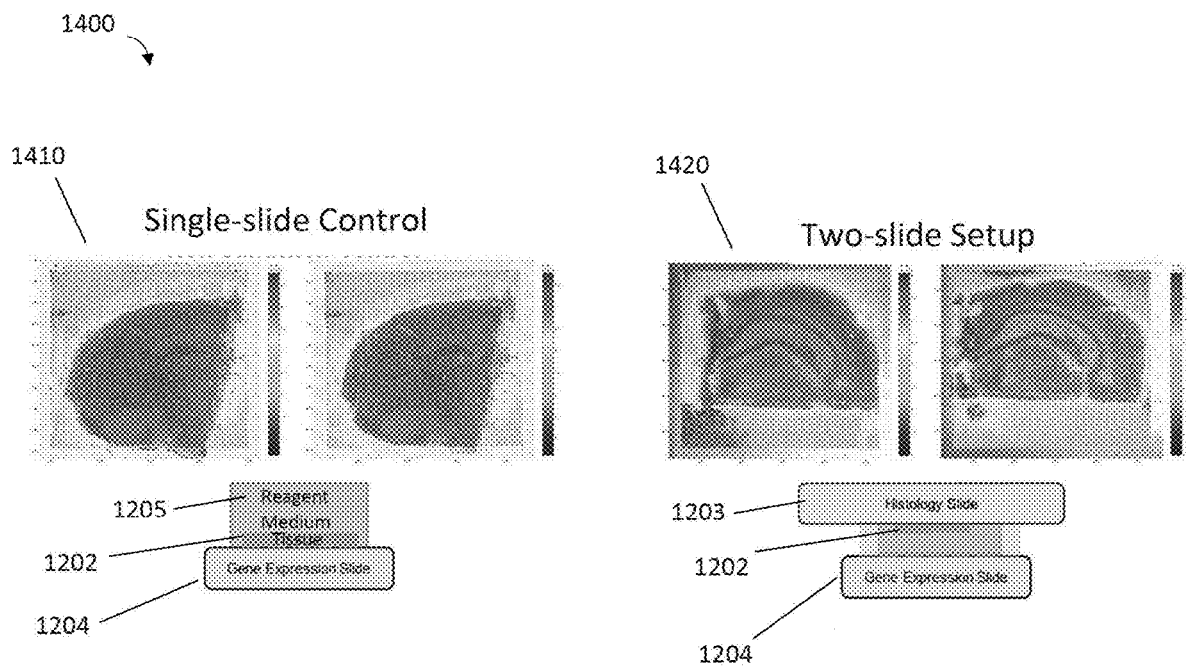
FIG. 13 shows a table providing median genes per spot and median unique molecular identifier (UMI) counts per spot in a formalin-fixed mouse brain sample.
FIG. 14 shows visual heat map results showing $Log_{10}$ UMI counts in a control single slide and a two slide spatial set up embodiments.

Results depicting median genes per spot and median UMI counts per spot are shown in FIG. 13.

Visual heat map results showing Log 10 UMIs are shown in FIG. 14. Spatial patterns of the Log 10 UMI counts were similar across the two-slide and control conditions.

Figure 15:
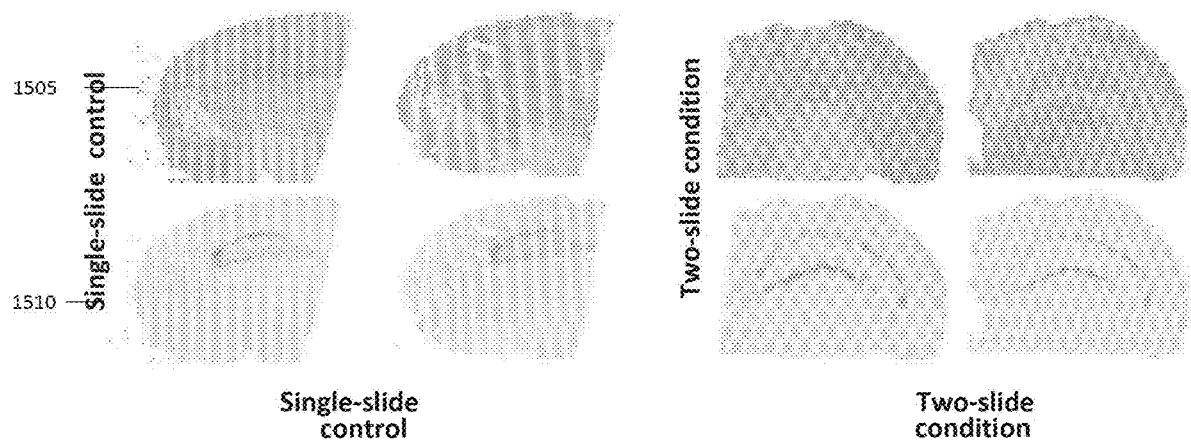
FIG. 15 shows spatial clustering analysis images in control and two-slide spatial array embodiments.

Spatial clustering analysis (top row 1505) and analysis of hippocampal transcript Hpca (bottom row 1510) are depicted in FIG. 15. Spatial patterns were comparable across the two-slide and control conditions.

Example 2: Method of Identifying Methylation Status of an Analyte

Figure 10:
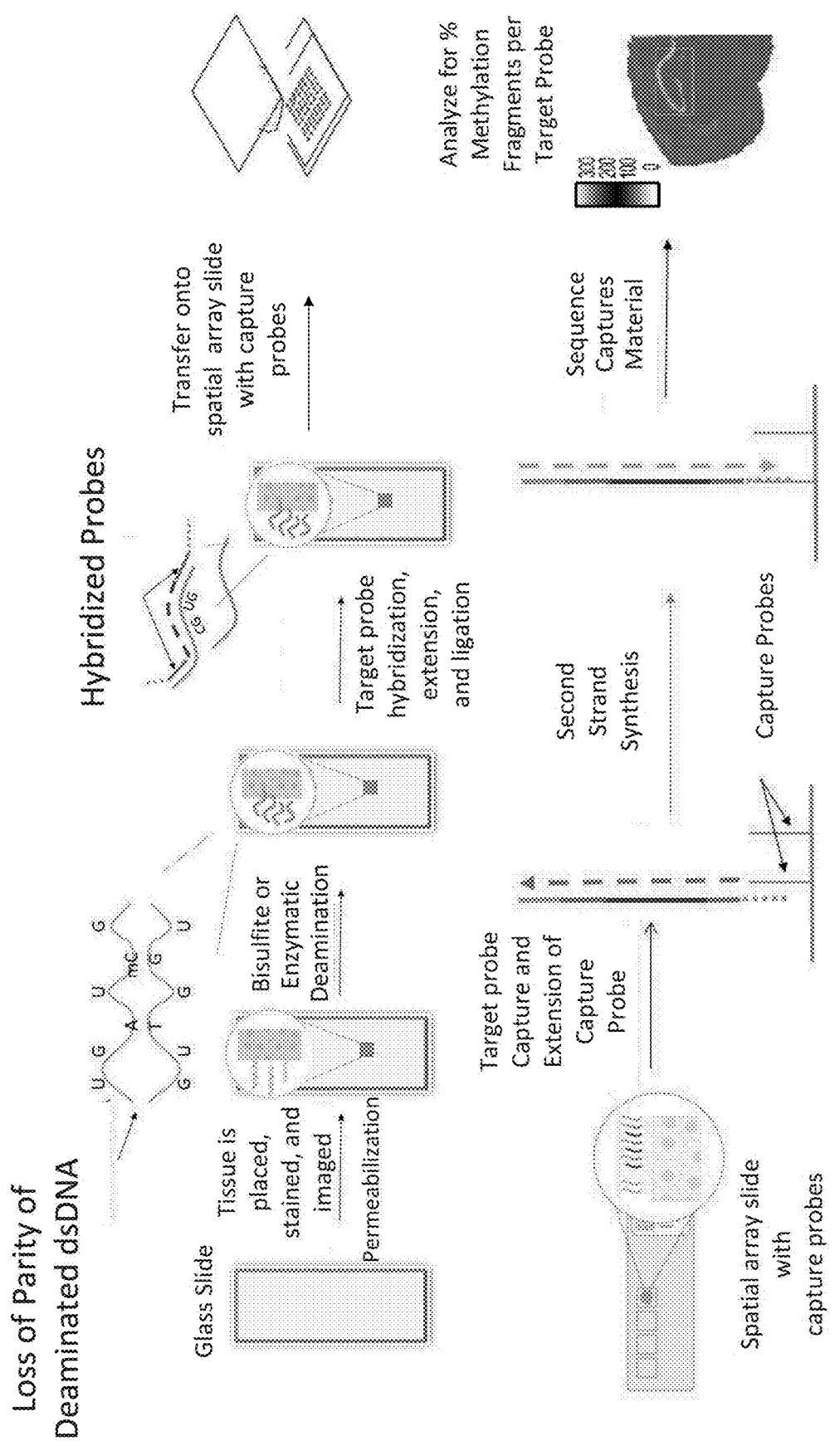
FIG. 10 shows a schematic of an example analytical workflow of generating a deaminated nucleic acid in a biological sample and identifying a methylation status of a deaminated nucleic acid in a biological sample.

FIG. 10 is an exemplary workflow of the methods described herein for identifying methylation status of a biological sample.

Specifically, a regular slide (e.g., a glass slide) is provided. The biological sample (e.g., a tissue) is placed on the slide, stained and imaged. The tissue is permeabilized, and a bisulfite reagent or a deaminating enzyme is applied to the tissue. During the deamination, the double-stranded DNA fragments become single-stranded due to loss of parity when methylated cytosines are converted to uracils. After the bisulfite or deaminating reagent is washed away, one or more probes targeting regions of interest (such as CpG islands) on the analytes in the tissue are hybridized to the analytes in the biological sample and are extended. The probes are designed to target (e.g., hybridize to) regions that do not have CG dinucleotides. They are also designed to include overhangs that specifically hybridize to the capture domain of the capture probes on a spatial array. After hybridization of the probes to the analyte, in this example one of the probes is extended using a polymerase, creating an oligonucleotide that is complementary to the regions between the hybridized probes. The probes are ligated, creating a ligation product that includes a sequence complementary to the deaminated analyte of interest. The ligation product (through one of the probes) includes a sequence (e.g., an overhang sequence) complementary to a capture probe on a spatial array.

As shown in the lower panel of FIG. 10, a spatial array on a slide comprising a plurality of capture probes with location UMIs is provided. The ligation product is transferred onto the spatial array slide using a suitable method described herein. Using the overhang of the ligation product, the ligation product hybridizes to the capture probes on the spatial array slide surface. The capture probes are extended using the ligation product as a template. The ligation product is denatured, and using a primer sequence from the capture probe, a plurality of nucleic acids are synthesized that include the sequence of the UMI and spatial barcode, or a complement thereof, and the sequence of the region of interest on the analyte, or a complement thereof.

The plurality of nucleic acids is subsequently sequenced, and the sequence of all or a part of the UMI and spatial barcode, as well as the sequence of all or a part of the region of interest on the analyte is determined and analysis carried out to determine the % of methylated fragments per target probe in a region of interest (HPCA gene methylation in this example).

Example 3: Method of Identifying Methylation Status in an Analyte Using Tagmented Samples FIGS. 11A-11B is an exemplary workflow of the methods described herein.

As shown in FIG. 11A, the biological sample (e.g., a tissue section) is placed on a regular slide without capture probes (the tissue is optionally stained and imaged in this example). The tissue is permeabilized, and the analytes (e.g., DNA) are tagmented by a transposase (Tn5) complexed with transposons that include methylated adaptors, extended and ligated to create tagmented dsDNA. The tagmented double-stranded DNA is deaminated using a bisulfite reagent or a deamination enzyme and denatured to form a single-stranded tagmented DNA. The single-stranded tagmented DNA is then transferred to a spatial array on a slide comprising a plurality of capture probes with locational barcodes and UMIs. The transferred single-stranded tagmented DNA is ligated to the capture probes on the slide using a splint oligonucleotide to bring the ends of the tagmented DNA in proximity to the capture probe for ligation to occur. The captured DNA is then treated with terminal transferase, dCTP and a uracil-friendly polymerase to add a poly(C) tail to the captured DNA, which serves as a hybridization site for a poly(G) primer to form a plurality of amplifiable nucleic acids.

As shown in FIG. 11B, these nucleic acids are prepared for sequencing, sequenced, and the sequence of all or a part of the UMI and spatial barcode, as well as the sequence of all or a part of the region of interest on the analyte is determined. The data is analyzed and a percentage or degree of methylation of the DNA fragments is spatially determined (HPCA gene methylation in this example).

Example 4: Method of Identifying Methylation Status of an Analyte

Figure 16:
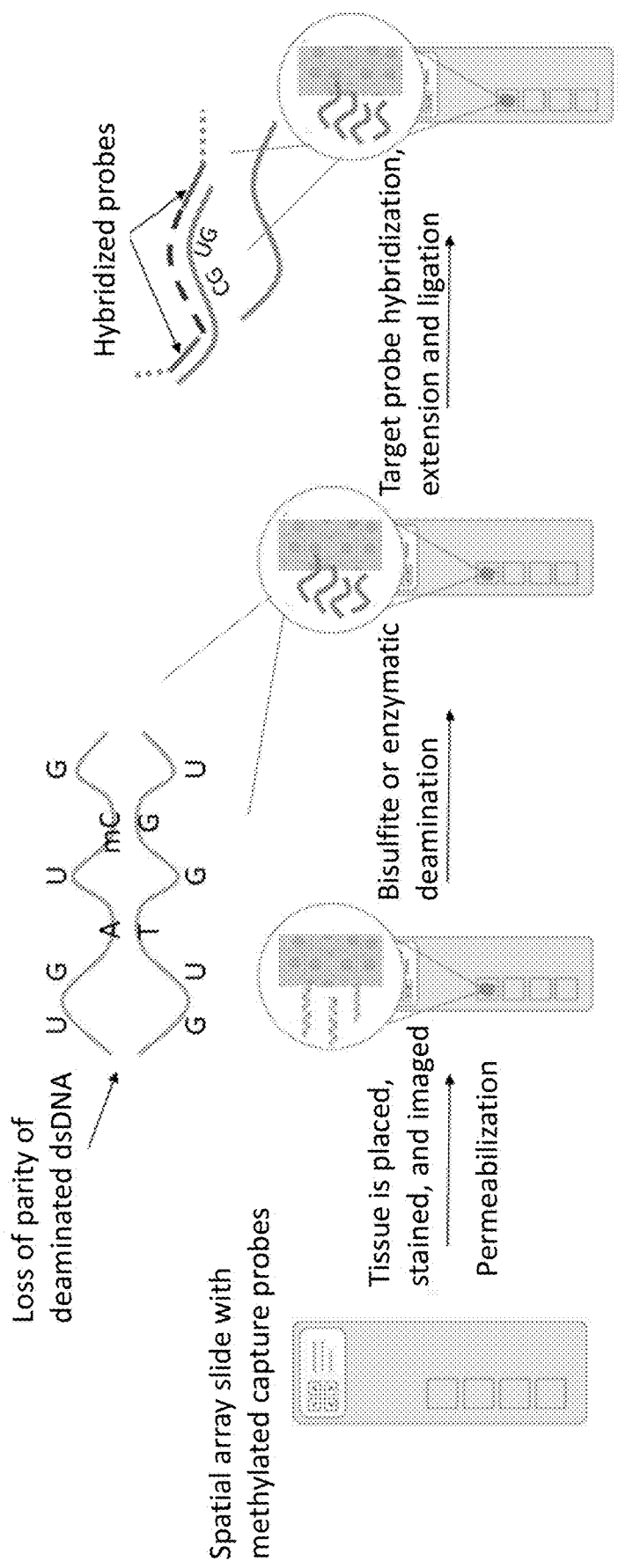
FIG. 16 shows a schematic of an example analytical workflow of generating a deaminated nucleic acid in a biological sample.

FIG. 16 is an exemplary workflow of the methods described herein.

Specifically, an array on a slide comprising a plurality of methylated capture probes (i.e., methylated cytosines) with location UMIs are provided. Because the capture probes include methylated cytosines, the capture probes are left intact in the presence of deaminating agents. As shown in FIG. 16, the sample (e.g., a tissue) is placed on a slide, stained and imaged. The tissue is permeabilized, and a bisulfite reagent or a deaminating enzyme is applied to the tissue. During the deamination, the double-stranded DNA fragments become single-stranded due to loss of parity when methylated cytosines are converted to uracils. After the bisulfite or deaminating reagent is washed away, one or more probes targeting regions of interest (such as CpG islands) on the analytes in the tissue are hybridized to the analytes in the biological sample and are extended. The probes are designed to target (e.g., hybridize to) regions that do not have CG dinucleotides. They are also designed to include overhangs that specifically hybridize to the capture domain of the capture probes on the slide surface. After hybridization of the probes to the analyte, in this example one of the probes is extended using a polymerase, creating an oligonucleotide that is complementary to the regions between the hybridized probes. The probes are ligated, creating a ligation product that includes a sequence complementary to the deaminated analyte of interest. The ligation product (through one of the probes) includes a sequence (e.g., an overhang sequence) complementary to a capture probe on the array.

Using the overhang, the ligation product binds to the capture probes on the slide surface. The capture probes are extended using the ligation product as a template. The ligation product is denatured, and using a primer sequence from the capture probe, a plurality of nucleic acids are synthesized that include the sequence of the UMI and spatial barcode, or a complement thereof, and the sequence of the region of interest on the analyte, or a complement thereof.

These nucleic acids are subsequently sequenced, and the sequence of all or a part of the UMI and spatial barcode, as well as the sequence of all or a part of the region of interest on the analyte is determined and analysis carried out to determine the % of methylated fragments per target probe in a region of interest (HPCA gene methylation in this example).

Figure 17:
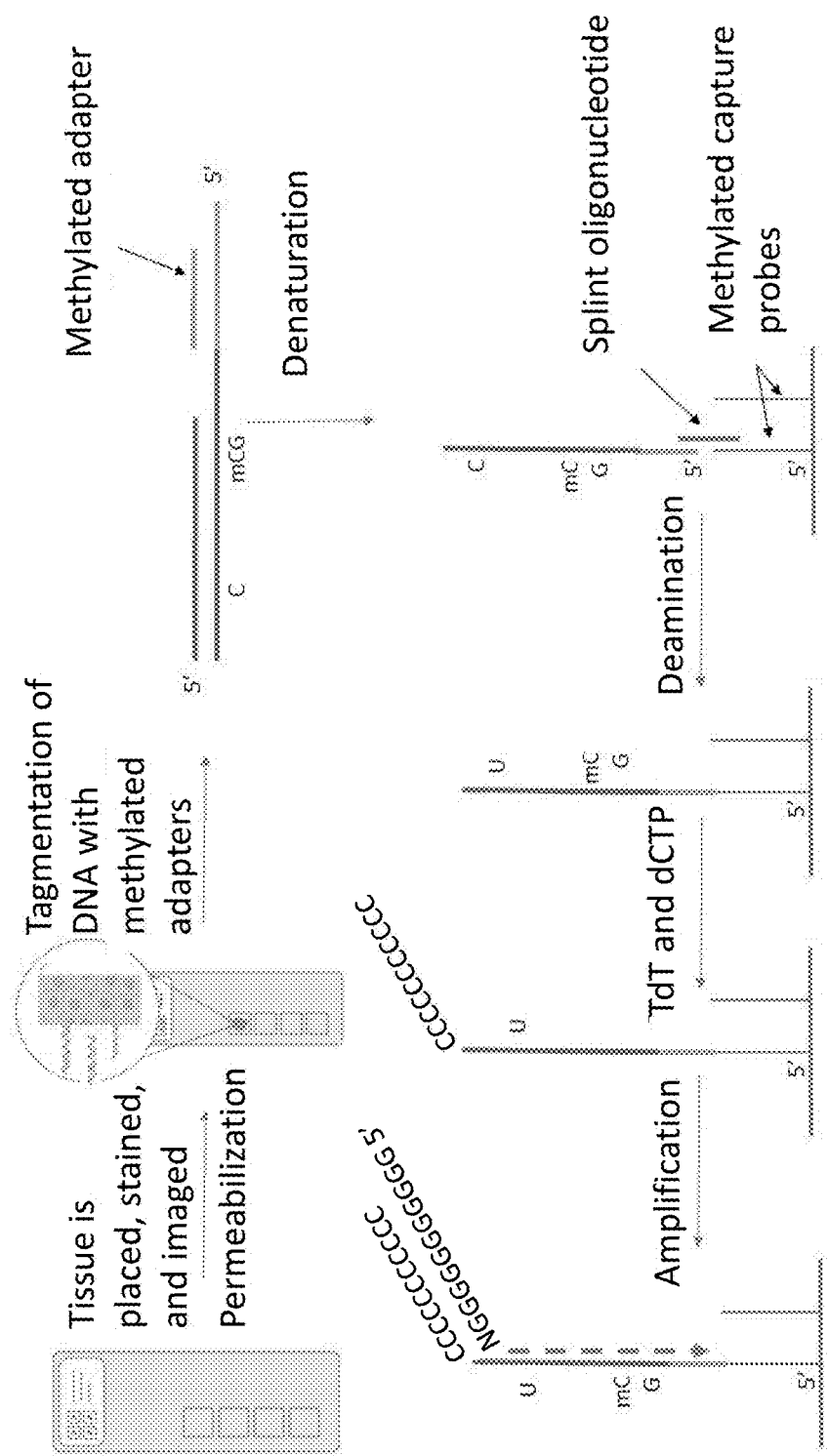
FIG. 17 shows a schematic of an example analytical workflow of generating a deaminated nucleic acid in a biological sample.

Example 5: Method of Identifying Methylation Status in an Analyte Using Tagmented Samples FIG. 17 is an exemplary workflow of the methods described herein.

Specifically, an array on a slide comprising a plurality of methylated capture probes (i.e., methylated cytosines) with locational barcodes and UMIs are provided. Because the capture probes include methylated cytosines, the capture probes are left intact in the presence of deaminating agents. As shown in FIG. 17, the sample (e.g., a tissue) is placed on a slide (optionally stained and imaged in this example). The tissue is permeabilized, and the analytes (e.g., DNA) are tagmented by a transposase (Tn5 complexed with transposons that include methylated adaptors), extended and ligated to create tagmented dsDNA. The tagmented double-stranded DNA is denatured to form a single-stranded tagmented DNA. The single-stranded tagmented DNA is ligated to the capture probes on the slide using a splint oligonucleotide to bring the ends of the tagmented DNA in proximity to the capture probe for ligation to occur. The ligation product is deaminated using a bisulfate reagent or a deamination enzyme. The captured DNA is then treated with terminal transferase, dCTP and a uracil-friendly polymerase to add a poly(C) tail to the captured DNA, which serves as a hybridization site for a poly(G) primer to form a plurality of amplifiable nucleic acids.

These nucleic acids are prepared for sequencing, sequenced, and the sequence of all or a part of the UMI and spatial barcode, as well as the sequence of all or a part of the region of interest on the analyte is determined. The data is then analyzed and a percentage or degree of methylation of the DNA fragments is determined (HPCA gene methylation in this example).

Example 6. Whole Genome Methylation Profiling Using Spatial Gene Expression Platform and in Droplets FIGS. 18A-18B show an exemplary workflow of the tagmentation methods described herein.

Specifically, DNA methylation profiling is achieved on spatial gene expression slides or droplets using transposase (e.g., Tn5, Tn7, Mu, Mariner, Sleeping Beauty, etc.) mediated tagmentation to add methylated adapters or using an enzyme tethering approach for more targeted tagmentation, e.g. by fusing a transposase to an inactive restriction enzyme like MspI (recognition site: CCGG, used in reduced representation bisulfite sequencing (RRBS) or to Dnmt1, the maintenance methyltransferase).

Figure 18A:
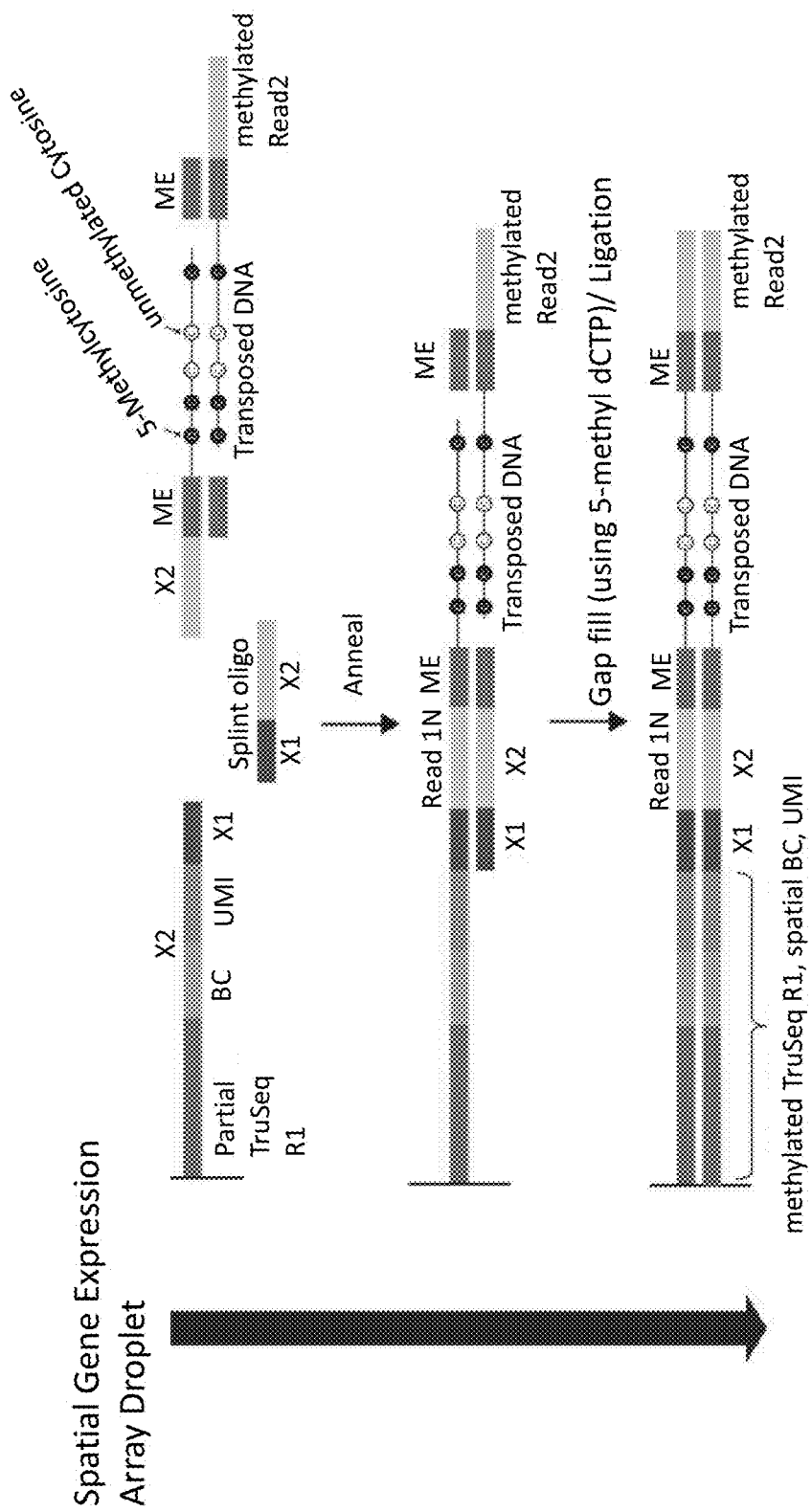
FIG. 18A shows a schematic of an example analytical workflow of tagmentation of DNA molecules in a biological sample and capture of the tagmented DNA fragments on spatial gene expression slides.
Figure 18B:
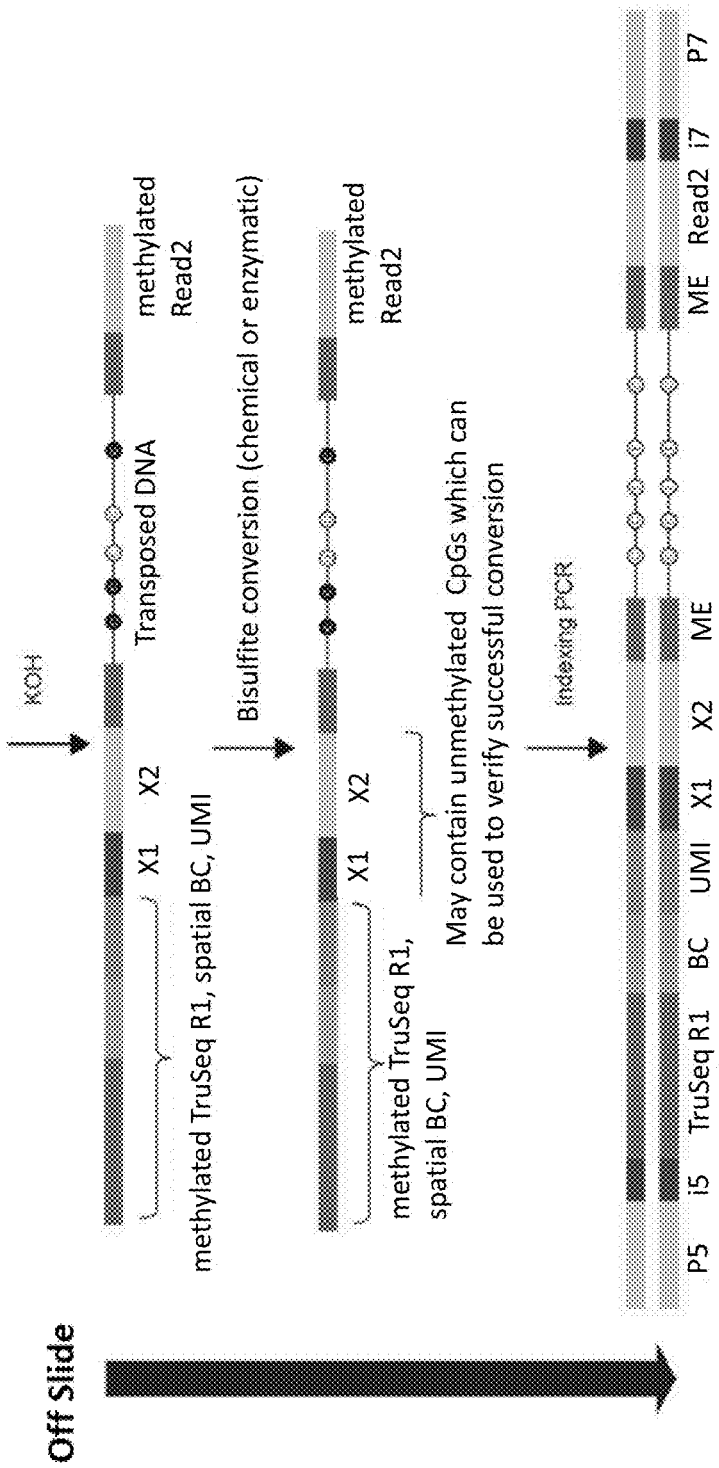
FIG. 18B shows a schematic of an example analytical workflow of generating a library for whole genome methylation profiling (e.g., whole genome bisulfite sequencing) using the captured tagmented DNA fragments from FIG. 18A.

As shown in FIG. 18A, analytes (e.g., DNA) in a biological sample are fragmented and tagged via tagmentation processes by, e.g., Tn5, MspI-Tn5 fusion, or Dnmt1-Tn5 fusion. Methylated R2 handles are added to the 3' and/or 5' ends of the DNA fragments. The biological sample (e.g., tissue sample) is permeabilized and the tagmented DNA molecules bound to an array of capture probes on a gene expression slide or a solid support in a droplet by ligating the handles (e.g., X2 or R2 handles) onto the DNA fragments and the capture probes on the slide surface or solid surface in the droplet, for example using a splint oligonucleotide.

The ligated DNA fragments are extended using a dNTP mixed that includes 5' methyl CTP and the extended DNA fragments are denatured and removed from the slides or solid support in droplets using a denaturing reagent (e.g., KOH).

The denatured DNA fragments are treated with a deamination reagent (e.g., a bisulfite reagent). The handles and barcodes on the capture probes are pre-methylated so they won't be affected by the deamination process. For targeted capture, a probe panel is used to enrich differentially methylated regions (DMRs). Commercially available probe panels such as Agilent SureSelect XT Human Methyl-Seq panel (Agilent, Santa Clara, Calif.) can be used in the method described herein.

The deaminated DNA fragments are amplified using indexing PCR with a suitable polymerase such as Takara EpiTaq HS (Takara, Mountain View, Calif.). Optionally, the amplified DNA fragments are captured and mitochondrial DNA removed before sequencing.

Example 7: Method of Identifying Methylation Status in an Analyte

Figure 19A:
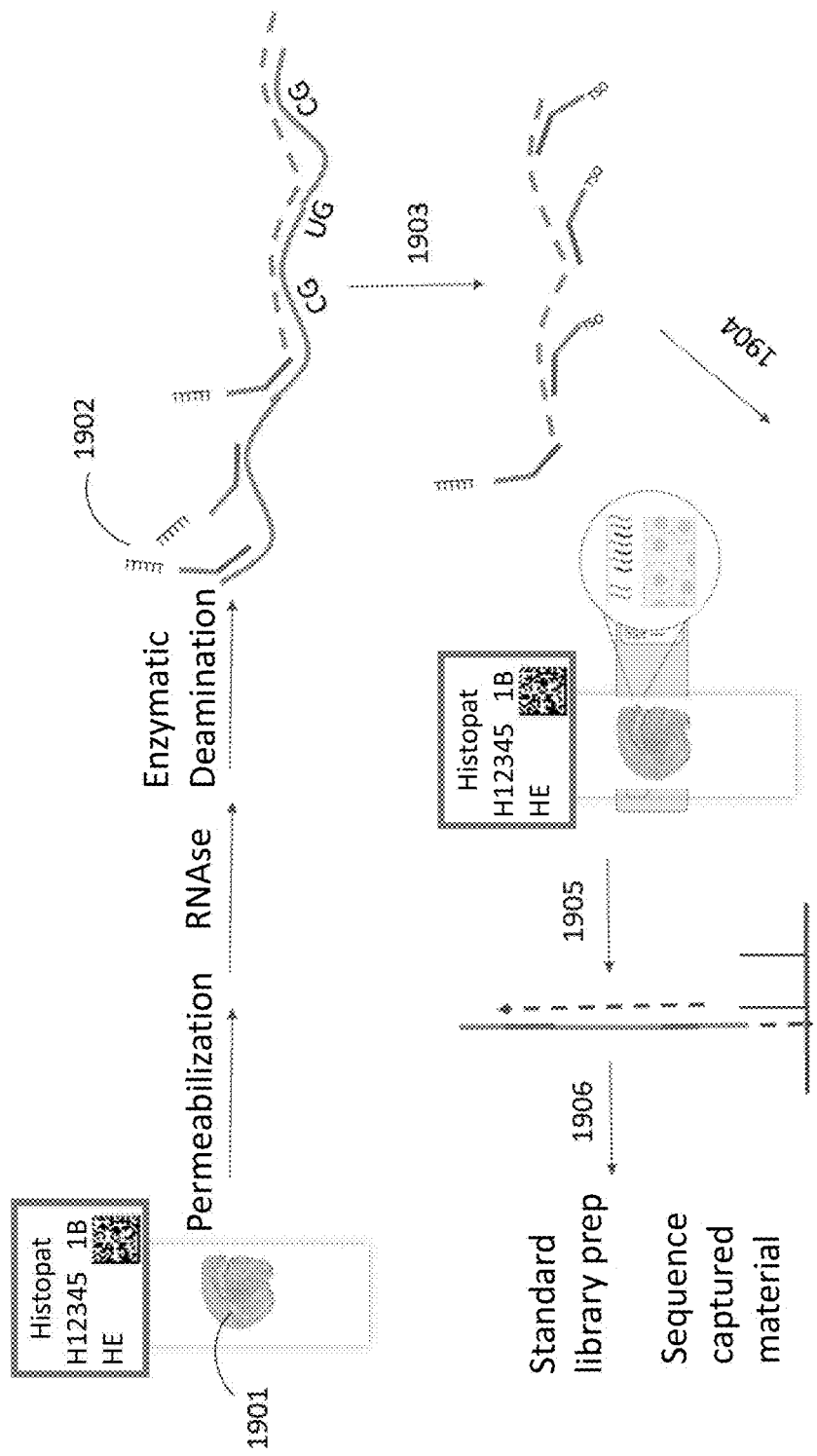
FIG. 19A shows an exemplary embodiment of spatial deamination methods disclosed herein.
Figure 19B:
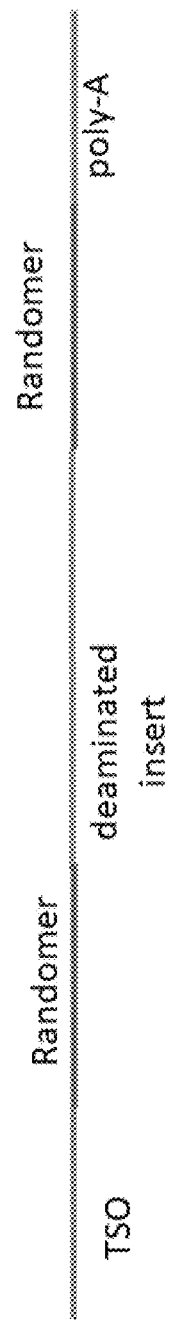
FIG. 19B shows the deaminated nucleic acid product after amplification and before capture on an array.

FIG. 19A shows an exemplary workflow used herein. In particular, a mouse brain tissue sample was sectioned and was placed on a microscopy slide. The tissue section 1901 was fixed, stained with H&E, and imaged. After destaining with HCl, the sample was permeabilized for 15 minutes at room temperature with a protease in phosphate buffer saline (PBS). The tissue section was treated with a solution comprising RNAse for 15 minutes at room temperature in order to remove any RNA that could compete with DNA to hybridize to a capture probe on an array. The sample then was washing with nuclease free water, and enzymatic deamination (New England Biolabs® Inc.). Specifically, Tet methylcytosine dioxygenase 2 (TET2) was mixed in a solution to a 1× concentration, and the sample was incubated for 1 hour at 37° C. The sample then was washed in 1×SSC. After, the sample was incubated in 20% formamide for 10 minutes at 85° C. The sample was treated with apolipoprotein B mRNA-editing enzyme, catalytic polypeptide (APOBEC) for 4 hours at 37° C. in order to convert deaminating cytosine to uracil. After a wash step with 2×SSC, the nucleic acids in the sample were amplified 1903 using a DNA polymerase and primers 1902 comprising a random hexamer (e.g., randomers) and a poly-thymine (n=30 thymine nucleotides) overhang. The amplified nucleic acids, shown in FIG. 19B and comprising a deaminated sequence, randomer sequences, a poly-A tail, and a templated switching oligo (TSO), were denatured with a solution of KOH for 5 minutes.

An array comprising captures probes having a capture domain with a poly-thymine sequence was sandwiched 1904 onto the sample. The tissue section was permeabilized and the denatured nucleic acids were captured on the array at 37° C. for 30 minutes. A DNA polymerase was used to extend 1905 the capture probe using the captured nucleic acid as a template. After, qPCR was performed; the resulting amplified products were fragmented, indexed and sequenced 1906.

Figure 20:
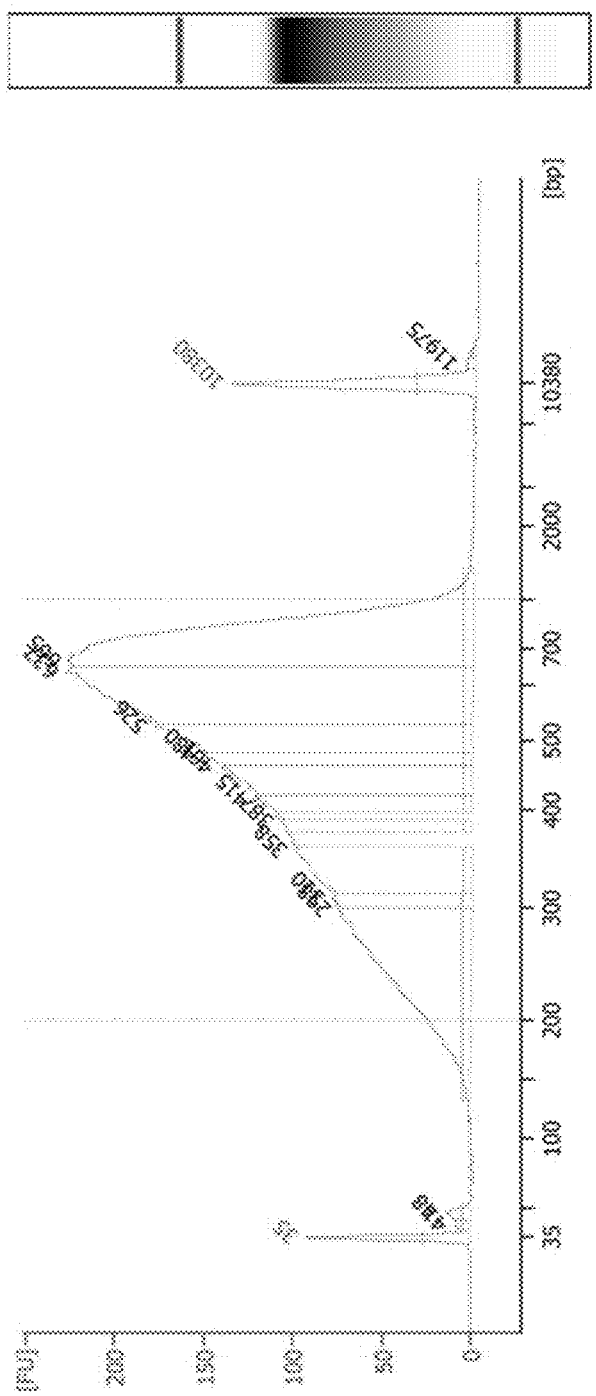
FIGS. 20 and 21 show representative electropherogram of sequenced DNA molecules after capture on an array.
Figure 21:
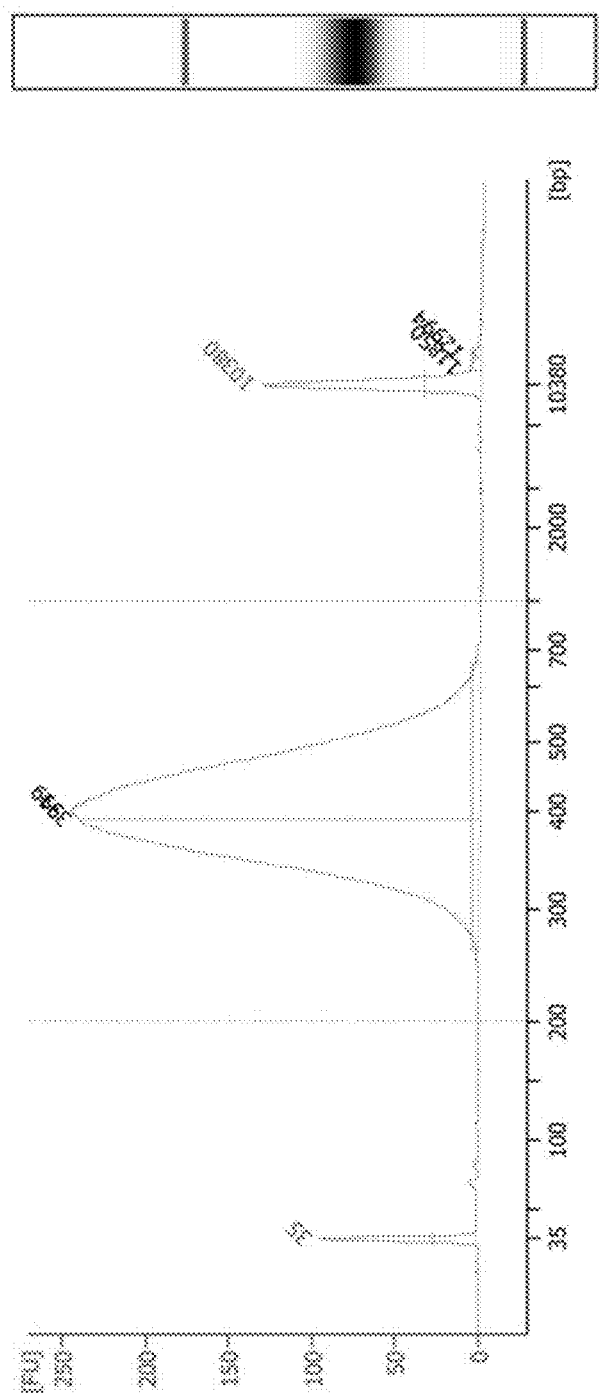
Figure 22:
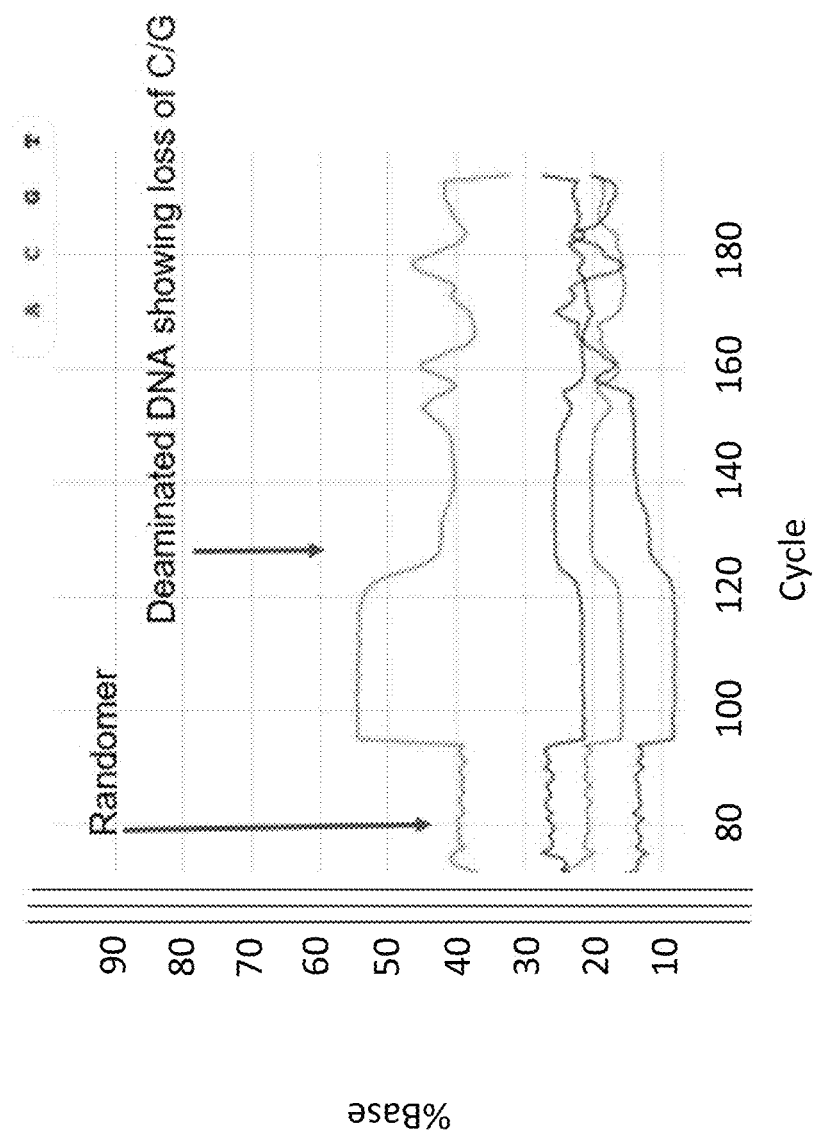
FIG. 22 shows sequencing results for the captured and deaminated target analyte with representative percentages of adenine (A), cytosine (C), guanine (G), and thymine (T)

FIGS. 20 and 21 provide summaries of electropherograms for two samples. In FIG. 20, the mouse brain tissue sample was deaminated after DNA amplification and 1× solid phase reversible immobilization (SPRI) cleanup, the elecropherogram demonstrating the range of amplification products from the randomer based amplification as expected. FIG. 21 shows an electropherogram after a 1:10 dilution of the final library, with additional SPRI clean up thereby focusing on a sequencing library of around 400 base pair fragments. The graphs in FIGS. 20 and 21 show that sequences ranging from 400-700 base pairs were obtained via sequencing. Further, as shown in FIG. 22, the sequencing data showed an increase in adenine nucleotides and a decrease in cytosine and guanine. These data demonstrate a proof of concept that a biological sample can be deaminated and nucleic acids from the biological sample can be captured on a spatial array, sequenced and analyzed. Thus, using the methods here, one can spatially examine methylation patterns in a biological sample.

What is claimed is:

1. A method for identifying methylation status of a nucleic acid in a biological sample, the method comprising:
   (a) contacting the biological sample with a substrate;
   (b) deaminating the nucleic acid in the biological sample;
   (c) contacting the deaminated nucleic acid with a plurality of probes comprising a first probe and a second probe, wherein the first probe and the second probe hybridize to the deaminated nucleic acid and wherein:
      the first probe comprises (i) a sequence complementary to a first sequence of the deaminated nucleic acid and (ii) a sequence complementary to a capture domain of a capture probe; and
      the second probe comprises a sequence complementary to a second sequence of the deaminated nucleic acid;
   (d) ligating the first probe and the second probe, thereby generating a ligation product;
   (e) hybridizing the ligation product to the capture probe; and
   (f) determining (i) the sequence of a spatial barcode of the capture probe, or the complement thereof, and (ii) all or part of the sequence of the ligation product, or a complement thereof, and using the determined sequences of (i) and (ii) to identify the methylation status of the nucleic acid in the biological sample.

2. The method of claim 1, wherein the substrate comprises an array comprising the plurality of capture probes, wherein a capture probe of the plurality of capture probes comprises (i) the spatial barcode and (ii) the capture domain.

3. The method of claim 1, further comprising, between steps (d) and (e):
   aligning the substrate with a second substrate comprising an array, such that at least a portion of the biological sample is aligned with at least a portion of the array, wherein the array comprises the plurality of capture probes and wherein a capture probe of the plurality of capture probes comprises (i) the spatial barcode and (ii) the capture domain; and
   when the biological sample is aligned with at least a portion of the array, (i) releasing the ligation product from the deaminated nucleic acid and (ii) migrating the ligation product from the biological sample to the array.

4. The method of claim 3, wherein the substrate does not comprise an array of capture probes.

5. The method of claim 1, wherein the ligating comprises enzymatic ligation or chemical ligation, and wherein the enzymatic ligation utilizes a ligase selected from a splintR ligase, a single stranded DNA ligase, or a T4 DNA ligase.

6. The method of claim 1, wherein the nucleic acid is genomic DNA.

7. The method of claim 1, wherein the biological sample is a tissue section sample.

8. The method of claim 1, wherein the biological sample is a fixed sample, a frozen sample, a fresh sample, or a fresh frozen sample.

9. The method of claim 1, wherein the deaminating comprises contacting the biological sample with a composition comprising sodium bisulfite.

10. The method of claim 1, wherein the deaminating comprises treating the biological sample with an enzyme.

11. The method of claim 10, wherein the enzyme is a cytidine deaminase or a demethylase.

12. The method of claim 1, wherein the capture probe further comprises one or more functional domains, a unique molecular identifier, a cleavage domain, or combinations thereof.

13. The method of claim 1, further comprising extending the capture probe using the ligation product as a template.

14. The method of claim 1, wherein the determining comprises sequencing (i) all or a part of the sequence of the ligation product, or a complement thereof, and (ii) the spatial barcode, or a complement thereof.

15. The method of claim 1, wherein at least one deaminated nucleotide is located (i) between the first sequence and the second sequence, (ii) in the first sequence, and/or (iii) in the second sequence.

* * * * *